United States Patent
Fuchs et al.

(10) Patent No.: US 8,426,607 B2
(45) Date of Patent: Apr. 23, 2013

(54) SUBSTITUTED AMINO-BENZIMIDAZOLES, MEDICAMENTS COMPRIMISING SAID COMPOUND, THEIR USE AND THEIR METHOD OF MANUFACTURE

(75) Inventors: Klaus Fuchs, Mittelbiberach (DE); Cornelia Dorner-Ciossek, Warthausen (DE); Sandra Handschuh, Biberach (DE); Niklas Heine, Biberach (DE); Stefan Hoerer, Biberach (DE); Klaus Klinder, Oggelshausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 25 days.

(21) Appl. No.: 12/812,476

(22) PCT Filed: Jan. 21, 2009

(86) PCT No.: PCT/EP2009/000345
§ 371 (c)(1),
(2), (4) Date: Oct. 11, 2010

(87) PCT Pub. No.: WO2009/092566
PCT Pub. Date: Jul. 30, 2009

(65) Prior Publication Data
US 2011/0288139 A1  Nov. 24, 2011

(30) Foreign Application Priority Data
Jan. 22, 2008  (EP) .................................... 08100772

(51) Int. Cl.
A61K 31/4184  (2006.01)
C07D 235/30  (2006.01)
C07D 407/12  (2006.01)

(52) U.S. Cl.
USPC ............. 548/307.4; 514/388; 548/304.7

(58) Field of Classification Search .............. 548/307.4
See application file for complete search history.

(56) References Cited

U.S. PATENT DOCUMENTS
2006/0205941 A1 * 9/2006 Bressi et al. ............... 544/209
2007/0232642 A1  10/2007 Baxter et al.

FOREIGN PATENT DOCUMENTS
WO  2004/014905 A1  2/2004
WO  2007/084728 A2  7/2007

OTHER PUBLICATIONS

Agai et al., CA 85:78096, 1976.*
Thompson et al., Current Medicinal Chemistry, Oct. 2002, 9(19), pp. 1751-1762.*
Chemical Abstract & Chemical & Pharmaceutical Bulletin (2008) vol. 56, No. 7 pp. 894-896.
International Search Report for PCT/EP2009/000345 mailed May 27, 2009.
Snow, Roger J., et al; Hit-to Lead Studies on Benzimidazole inhibitors of ITK: Discovery of a Novel Class of Kinase Inhibitors; Biorganic & Medical Chemistry Letters (2007) vol. 17 pp. 3660-3665.

* cited by examiner

Primary Examiner — Laura L. Stockton
(74) Attorney, Agent, or Firm — Michael P. Morris; Edward S. Lazer

(57) ABSTRACT

The present invention relates to substituted amino-benzimidazoles of general formula (1) wherein the groups $R^1$ to $R^{14}$ and A, are defined as in the specification and claims and the use thereof for the treatment of Alzheimer's disease (AD) and similar diseases.

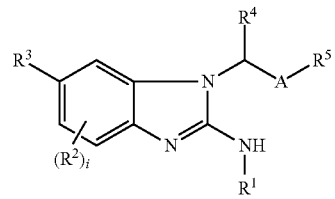

16 Claims, No Drawings

SUBSTITUTED AMINO-BENZIMIDAZOLES, MEDICAMENTS COMPRISING SAID COMPOUND, THEIR USE AND THEIR METHOD OF MANUFACTURE

This application is the national phase entry under 35 U.S.C. §371 of International Application No. PCT/EP2009/000345, filed Jan. 21, 2009, which claims priority to European Patent Applications No. 08100772.6, filed Jan. 22, 2008 which are hereby incorporated by reference in their entireties.

TECHNICAL FIELD

This invention relates to substituted amino-benzimidazoles and their use as β-secretase inhibitors, pharmaceutical compositions containing the same, and methods of using the same as agents for treatment and/or prevention of diseases and conditions in which the use of therapeutic effective amounts of compounds inhibiting β-secretase display a therapeutic benefit, e.g in Alzheimer's disease.

BACKGROUND ART

EP 652 009 A1 describes inhibitors of aspartate protease which inhibit the production of beta-amyloid peptides in cell culture and in vivo.

WO 00/69262 discloses a beta-secretase and the use thereof in assays for finding potential active substances for the treatment of AD.

WO 01/00663 discloses memapsin 2 (human beta-secretase) as well as a recombinant catalytically active enzyme. Methods of identifying inhibitors of memapsin 2 are also described.

The International patent applications WO 06/024932, WO 06/017836 and WO 06/017844 disclose substituted amino-quinazolines and their use as β-secretase inhibitors for the treatment of Alzheimer's disease.

WO 02/44156 discloses benzimidazole derivatives having TIE-2 and VEGFR-2 kinase inhibitory activity for the treatment of diseases associated with inappropriate angiogenesis, including cancer.

U.S. Pat. No. 05/065,179 discloses benzimidazole and imidazo-pyridine derivatives with high affinity for certain subtypes of melanocortin receptors being useful for treating pathological conditions in which one or more of those receptors are involved.

WO 03/041708 discloses benzimidazole and imidazo-pyridine derivatives inhibiting the Tec kinase family and therefore being useful for treating pathological conditions involving inflammation, immunological and allergic disorders.

WO 05/080380 discloses inhibitors of p38 kinase which have a benzimiadzole like structure and their use for the treatment of conditions resulting from excessive cytokine production.

WO 05/058869 discloses benzimidazole and aminobenzimidazoles having antiviral activity, by inhibiting the replication of the respiratory syncytial virus (RSV).

Surprisingly, it has been found that the compounds of the present invention inhibit beta secretase-mediated cleavage of APP, are weakly basic, are only partially protonated at physiological conditions, show high oral bioavailability.

DETAILED DESCRIPTION OF THE INVENTION

In a first aspect the present invention relates to substituted amino-benzimidazoles of general formula 1

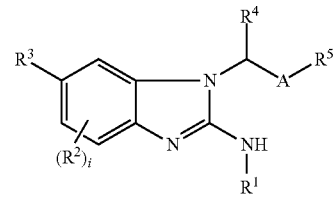

wherein
A is selected from the group GA.1 consisting of
a $C_1$-$C_3$-alkylene bridge, aryl-, heteroaryl- and heterocyclyl-,
wherein the above-mentioned members of the group GA.1 may optionally be substituted independently of one another by one or more substituents selected from the group consisting of
fluorine, chlorine, bromine, HO—, NC—, $O_2N$—, $F_3C$—, $HF_2C$—, $FH_2C$—, $F_3C$—$CH_2$—, $R^{14}$—O—$C_{1-6}$-alkyl-, $C_{1-6}$-alkyl-, $C_{1-6}$-alkyl-O—, $F_3C$—O—, $HF_2C$—O—, $FH_2C$—O—, $(R^{13})_2N$—, $(R^{13})_2N$—$C_{1-3}$-alkyl-, and $(R^{13})_2N$—CO—,
i is selected from the integers 0, 1 and 2,
$R^1$ is selected from the group GR1.1 consisting of
H—, HO—, methyl-, ethyl-, $F_3C$—, $F_3C$—$CH_2$—, $H_3C$—O—, $H_3C$—$CH_2$—O—, $H_3C$—C(O)—, and HC(O)—,
$R^2$ is selected from the group GR2.1 consisting of
fluorine, chlorine, bromine, HO—, NC—, $O_2N$—, $F_3C$—, $HF_2C$—, $FH_2C$—, $F_3C$—$CH_2$—, $F_3C$—O—, $HF_2C$—O—, $FH_2C$—O—, $C_{1-6}$-alkyl-, $C_{1-6}$-alkyl-S—, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{14}$—O—, $R^{14}$—O—$C_{1-3}$-alkyl-, $(R^{13})_2N$—, $(R^{13})_2N$—CO—, $R^{13}$—CO—$(R^{13})N$—, $(R^{13})_2N$—CO—$(R^{13})N$—, $R^{13}$—$SO_2$—$(R^{13})N$—, $(R^{13})_2N$—$SO_2$— and $R^{13}$—$SO_2$—,
wherein the above-mentioned members of the group GR2.1 may optionally be substituted independently of one another by one or more substituents selected from the group consisting of
fluorine, chlorine, bromine, HO—, NC—, $O_2N$—, $F_3C$—, $HF_2C$—, $FH_2C$—, HO—$C_{1-6}$-alkyl-, $CH_3$—O—$C_{1-6}$-alkyl-, $C_{1-6}$-alkyl-, $C_{1-6}$-alkyl-O—, $(R^{13})_2N$—, $(R^{13})_2N$—$C_{1-3}$-alkyl-, and $(R^{13})_2N$—CO—,
$R^3$ is selected from the group GR3.1 consisting of
H—, fluorine, chlorine, bromine, HO—, NC—, $F_3C$—, $HF_2C$—, $FH_2C$—, $F_3C$—$CH_2$—, $F_3C$—O—, $HF_2C$—O—, $FH_2C$—O—, $C_{1-6}$-alkyl-, $C_{1-6}$-alkyl-S—, $C_2$-$C_6$-alkenyl, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{12}$—O—, $R^{12}$—O—$C_{1-3}$-alkyl-, $R^{12}$—S—, $R^{12}$—CO—, $(R^{13})_2N$—, $(R^{13})_2N$—CO—, $R^{13}$—CO—$(R^{13})N$—, $(R^{13})_2N$—CO—$(R^{13})N$—, $R^{13}$—$SO_2$—$(R^{13})N$—, $(R^{13})_2N$—$SO_2$— and $R^{13}$—$SO_2$—,
wherein the above-mentioned members of the group GR3.1 may optionally be substituted independently of one another by one or more substituents selected from the group consisting of fluorine, chlorine, bromine, HO—, NC—, $O_2N$—, $F_3C$—, $HF_2C$—, $FH_2C$—, $F_3C$—$CH_2$—, $R^{14}$—O—, $R^{14}$—O—$C_{1-6}$-alkyl-, $C_{1-6}$-alkyl-, $(R^{13})_2N$—, $(R^{13})_2N$—$C_{1-3}$-alkyl-, and $(R^{13})_2N$—CO—, $R^4$ is selected from the group GR4.1 consisting of
H—, fluorine, NC—, $F_3C$—, $HF_2C$—, $FH_2C$—, $F_3C$—$CH_2$—, $C_{1-6}$-alkyl-, $C_2$-$C_6$-alkenyl, $C_{1-6}$-alkyl-S—, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{14}$—O—, and $R^{14}$—O—$C_{1-3}$-alkyl-, wherein the above-mentioned members of the group GR4.1 may optionally be substituted independently of one another by one or more substituents selected from the group consisting of
fluorine, chlorine, bromine, HO—, NC—, $O_2N$—, $F_3C$—, $HF_2C$—, $FH_2C$—, $F_3C$—$CH_2$—, HO—$C_{1-6}$-alkyl-, $CH_3$—O—$C_{1-6}$-alkyl-, $C_{1-6}$-alkyl-, $C_{1-6}$-alkyl-O—, $(R^{13})_2N$—, $(R^{13})_2N$—$C_{1-3}$-alkyl-, and $(R^{13})_2N$—CO—, $R^5$ is selected from the group GR5.1 consisting of
$R^6R^7N$—CO—, $R^8$—CO—$(R^9)N$—, and $R^{10}R^{11}N$—CO—$(R^9)N$—, $R^6$, $R^7$ are selected from the group GR6/11.1 consisting of $R^8$, $R^9$ H—, $F_3C$—, $HF_2C$—, $FH_2C$—, $F_3C$—$CH_2$—, $C_{1-8}$-alkyl-, $C_2$-$C_6$-alkenyl, $C_{1-6}$-alkyl-S—$R^{10}$, $R^{11}$ $C_{1-3}$-alkyl-, $C_{3-7}$-cycloalkyl-, $C_{3-7}$-cycloalkyl-$C_{1-6}$-alkyl-, $C_{6-12}$-polycycloalkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, and $R^{14}$—O—$C_{1-3}$-alkyl-, wherein, if $R^6$ and $R^7$ or $R^{10}$ and $R^{11}$ are $C_{1-6}$-alkyl groups, those two $C_{1-6}$-alkyl groups bound to the same nitrogen atom of $R^5$ may be joined together forming, together with the nitrogen atom to which they are bound, a 3 to 7 membered heterocyclic ring, and wherein one of the —$CH_2$-groups of the heterocyclic ring formed by the $R^6$ and $R^7$ or $R^{10}$ and $R^{11}$ $C_{1-6}$-alkyl groups and the nitrogen atom of $R^5$ may be replaced by —O—, —S—, N—H, —$N(C_{3-6}$-cycloalkyl)-, —$N(C_{3-6}$-cycloalkyl-$C_{1-4}$-alkyl)- or —$N(C_{1-4}$-alkyl)- and wherein the above-mentioned members of the group GR6/11.1 including the heterocyclic ring formed by the $R^6$ and $R^7$ or $R^{10}$ and $R^{11}$ $C_{1-6}$-alkyl groups and the nitrogen atom of $R^5$ may optionally be substituted independently of one another by one or more substituents selected from group GR6/11.S1 consisting of
fluorine, chlorine, bromine, HO—, NC—, $O_2N$—, $F_3C$—, $HF_2C$—, $FH_2C$—, $HO_2C$—, $C_{1-3}$-alkyl-O—C(O)—, HO—$C_{1-6}$-alkyl-, $C_{1-6}$-alkyl-, $C_{3-7}$-cycloalkyl-, $C_{1-6}$-alkyl-O—, $C_{1-6}$-alkyl-O—$C_{1-6}$-alkyl-, aryl-, $(R^{13})_2N$—, $(R^{13})_2N$—$C_{1-3}$-alkyl-, and $(R^{13})_2N$—CO— wherein the above-mentioned aryl of group GR6/11.S1 may optionally be substituted independently of one another by one or more substituents selected from group consisting of
fluorine, chlorine, bromine, NC—, $F_3C$—, $HF_2C$—, $FH_2C$—, $F_3C$—$CH_2$—, HO—$C_{1-6}$-alkyl-, $C_{1-6}$-alkyl-, and $C_{1-6}$-alkyl-O—, $R^{12}$ is selected from the group GR12.1 consisting of
$F_3C$—, $HF_2C$—, $FH_2C$—, $F_3C$—$CH_2$—, $C_{1-6}$-alkyl-, $C_{3-6}$-alkenyl-, $C_{1-6}$-alkyl-S—$C_{1-3}$-alkyl-, $C_{1-6}$-alkyl-O—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, and heteroaryl-$C_{1-6}$-alkyl-, wherein the above-mentioned members of the group GR12.1 may optionally be substituted independently of one another by one or more substituents selected from the group consisting of
fluorine, chlorine, bromine, $R^{14}$—O—, NC—, $O_2N$—, $F_3C$—, $HF_2C$—, $FH_2C$—, $F_3C$—$CH_2$—, $R^{14}$—O—$C_{1-6}$-alkyl-, $C_{1-6}$-alkyl-, $(R^{13})_2N$—, $(R^{13})_2N$—$C_{1-3}$-alkyl-, and $(R^{13})_2N$—CO—.

$R^{13}$ is selected from the group GR13.1 consisting of
H—, $F_3C$—$CH_2$—, $C_{1-6}$-alkyl-, $C_{2-6}$-alkenyl-, $C_{1-6}$-alkyl-S—$C_{1-3}$-alkyl-, $C_{1-6}$-alkyl-O—$C_{1-3}$-alkyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl-, and heteroaryl-$C_{1-3}$-alkyl-, wherein two $C_{1-6}$-alkyl groups bound to the same nitrogen atom may be joined together forming, together with the nitrogen atom to which they are bound, a 3 to 7 membered heterocyclic ring, and wherein one of the —$CH_2$-groups of the heterocyclic ring formed may be replaced by —O—, —S—, N—H, —$N(C_{3-6}$-cycloalkyl)-, —$N(C_{3-6}$-cycloalkyl-$C_{1-4}$-alkyl) or —$N(C_{1-4}$-alkyl)- and wherein the above-mentioned members of the group GR13.1 including the heterocyclic ring formed may optionally be substituted independently of one another by one or more substituents selected from the group consisting of
fluorine, chlorine, bromine, HO—, NC—, $O_2N$—, $F_3C$—, $HF_2C$—, $FH_2C$—, $F_3C$—$CH_2$—, HO—$C_{1-6}$-alkyl-, $CH_3$—O—$C_{1-6}$-alkyl-, $C_{1-6}$-alkyl-, $C_{1-6}$-alkyl-O— and $(C_{1-6}$-alkyl-$)_2N$—CO—.

$R^{14}$ is selected from the group GR14.1 consisting of
H—, $F_3C$—, $HF_2C$—, $FH_2C$—, $F_3C$—$CH_2$—, $C_{1-6}$-alkyl-, $C_{2-6}$-alkenyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl- and heteroaryl-$C_{1-3}$-alkyl-, wherein the above-mentioned members of the group GR14.1 may optionally be substituted independently of one another by one or more substituents selected from the group consisting of
fluorine, chlorine, bromine, HO—, NC—, $O_2N$—, $F_3C$—, $HF_2C$—, $FH_2C$—, $F_3C$—$CH_2$—, HO—$C_{1-6}$-alkyl-, $CH_3$—O—$C_{1-6}$-alkyl-, $C_{1-6}$-alkyl-, and $C_{1-6}$-alkyl-O— and $(R^{13})_2N$—CO—, and pharmaceutically acceptable salts thereof.

In another embodiment of the present invention

A is selected from the group GA.2 consisting of
—$CH_2$—, —$CH_2$—$CH_2$—, —$CH_2$—$CH_2$—$CH_2$—, aryl-, and heteroaryl-, wherein the above-mentioned members of the group GA.2 may optionally be substituted independently of one another by one or more substituents selected from the group consisting of
fluorine, chlorine, bromine, NC—, $F_3C$—, $HF_2C$—, $FH_2C$—, $F_3C$—$CH_2$—, $F_3C$—O—, $HF_2C$—O—, $FH_2C$—O—, HO—$C_{1-6}$-alkyl-, $C_{1-6}$-alkyl-O—$C_{1-6}$-alkyl-, $C_{1-6}$-alkyl-, and $C_{1-6}$-alkyl-O—.

In another embodiment the present invention

A is selected from the group GA.3 consisting of
—$CH_2$—$CH_2$—, —$CH_2$—$CH_2$—$CH_2$—, phenyl-, and pyridyl-, wherein the above-mentioned members of the group GA.3 may optionally be substituted independently of one another by one or more substituents selected from the group consisting of
fluorine, chlorine, bromine, NC—, $F_3C$—, $HF_2C$—, $FH_2C$—, $F_3C$—$CH_2$—, $F_3C$—O—, $HF_2C$—O—, $FH_2C$—O—, $H_3C$—, and $C_{1-6}$-alkyl-O—.

In another embodiment of the present invention
A is selected from the group GA.4 consisting of
—CH$_2$—CH$_2$—, and phenyl-,
especially

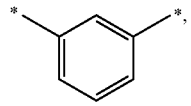

wherein the above-mentioned members of the group GA.4 may optionally be substituted independently of one another by one or more substituents selected from the group consisting of
fluorine, chlorine, CH$_3$—O—, C$_2$H$_5$—O—.

In another embodiment of the present invention
R$^1$ is selected from the group GR1.2 consisting of H—.

In another embodiment of the present invention
R$^2$ is selected from the group GR2.2 consisting of
fluorine, chlorine, bromine, NC—, F$_3$C—, HF$_2$C—, FH$_2$C—, F$_3$C—CH$_2$—, C$_{1-6}$-alkyl-, C$_{1-6}$-alkyl-S—, C$_{3-7}$-cycloalkyl-, C$_{3-7}$-cycloalkyl-C$_{1-6}$-alkyl-, and R$^{14}$—O—.

In another embodiment of the present invention
R$^2$ is selected from the group GR2.3 consisting of
fluorine, chlorine, bromine, NC—, F$_3$C—, HF$_2$C—, FH$_2$C—, F$_3$C—CH$_2$—, C$_{1-4}$-alkyl-, C$_{3-6}$-cycloalkyl-, C$_{3-6}$-cycloalkyl-C$_{1-4}$-alkyl-, aryl-O— and C$_{1-3}$-alkyl-O.

In another embodiment of the present invention
R$^2$ is selected from the group GR2.4 consisting of
CH$_3$—O—, chlorine and fluorine.

In another embodiment of the present invention
R$^3$ is selected from the group GR3.2 consisting of
fluorine, chlorine, bromine, NC—, F$_3$C—, HF$_2$C—, FH$_2$C—, F$_3$C—CH$_2$—, C$_{1-6}$-alkyl-, C$_{1-6}$-alkyl-S—, C$_{1-6}$-alkyl-S—C$_{1-3}$-alkyl-, C$_{3-7}$-cycloalkyl-, C$_{3-7}$-cycloalkyl-C$_{1-6}$-alkyl-, aryl-, aryl-C$_{1-6}$-alkyl-, heterocyclyl-, heterocyclyl-C$_{1-6}$-alkyl-, heteroaryl-, heteroaryl-C$_{1-6}$-alkyl-, R$^{12}$—O—, R$^{12}$—O—C$_{1-3}$-alkyl-, and R$^{12}$—CO—, wherein the above-mentioned members of the group GR3.2 may optionally be substituted independently of one another by one or more substituents selected from the group consisting of
fluorine, chlorine, bromine, HO—, NC—, F$_3$C—, HF$_2$C—, FH$_2$C—, F$_3$C—CH$_2$—, HO—C$_{1-6}$-alkyl-, CH$_3$—O—C$_{1-6}$-alkyl-, C$_{1-6}$-alkyl-, C$_{1-6}$-alkyl-O—, and (R$^{13}$)$_2$N—CO—.

In another embodiment of the present invention
R$^3$ is selected from the group GR3.3 consisting of
phenyl, heteroaryl-, and R$^{12}$—O—,
wherein the above-mentioned members of the group GR3.3 may optionally be substituted independently of one another by one or more substituents selected from the group consisting of
fluorine, chlorine, bromine, NC—, F$_3$C—, HF$_2$C—, FH$_2$C—, F$_3$C—CH$_2$—, C$_{1-3}$-alkyl-, CH$_3$—O—C$_{1-3}$-alkyl-, and C$_{1-3}$-alkyl-O—.

In another embodiment of the present invention
R$^3$ is selected from the group GR3.4 consisting of
phenyl, and phenyl-O—,
wherein the above-mentioned members of the group GR3.4 may optionally be substituted independently of one another by one or more substituents selected from the group consisting of
fluorine, chlorine, bromine, NC—, F$_3$C—, HF$_2$C—, FH$_2$C—, F$_3$C—CH$_2$—, C$_{1-3}$-alkyl-, CH$_3$—O—C$_{1-3}$-alkyl-, and C$_{1-3}$-alkyl-O—.

In another embodiment of the present invention
R$^4$ is selected from the group GR4.2 consisting of
H—, F$_3$C—, HF$_2$C—, FH$_2$C—, F$_3$C—CH$_2$—, C$_{1-6}$-alkyl-, C$_{1-6}$-alkyl-S—C$_{1-3}$-alkyl-, C$_{3-7}$-cycloalkyl-, C$_{3-7}$-cycloalkyl-C$_{1-3}$-alkyl-, aryl-, aryl-C$_{1-6}$-alkyl-, heterocyclyl-, heterocyclyl-C$_{1-3}$-alkyl-, heteroaryl-, heteroaryl-C$_{1-3}$-alkyl-, and R$^{14}$—O—C$_{1-3}$-alkyl-,
wherein the above-mentioned members of the group GR4.2 may optionally be substituted independently of one another by one or more substituents selected from the group consisting of
fluorine, chlorine, bromine, HO—, NC—, F$_3$C—, HF$_2$C—, FH$_2$C—, F$_3$C—CH$_2$—, HO—C$_{1-6}$-alkyl-, CH$_3$—O—C$_{1-6}$-alkyl-, C$_{1-6}$-alkyl-, and C$_{1-6}$-alkyl-O—.

In another embodiment of the present invention
R$^4$ is selected from the group GR4.3 consisting of
H—, C$_{1-6}$-alkyl-, C$_{1-4}$-alkyl-S—C$_{1-3}$-alkyl-, C$_{3-6}$-cycloalkyl-, C$_{3-6}$-cycloalkyl-C$_{1-3}$-alkyl-, aryl-, heterocyclyl-, heterocyclyl-C$_{1-3}$-alkyl-, heteroaryl-, and C$_{1-4}$-alkyl-O—C$_{1-3}$-alkyl-,
wherein the above-mentioned members of the group GR4.3 may optionally be substituted independently of one another by one or more substituents selected from the group consisting of
fluorine, chlorine, HO—, NC—, F$_3$C—, HF$_2$C—, FH$_2$C—, F$_3$C—CH$_2$—, CH$_3$—O-methyl-, C$_{1-3}$-alkyl-, and C$_{1-4}$-alkyl-O—.

In another embodiment of the present invention
R$^4$ is selected from the group GR4.4 consisting of
H—, C$_{1-6}$-alkyl-, C$_{3-6}$-cycloalkyl-, and C$_{3-6}$-cycloalkyl-C$_{1-2}$-alkyl-, C$_{1-4}$-alkyl-O—C$_{1-3}$-alkyl-,
wherein the above-mentioned members of the group GR4.4 may optionally be substituted independently of one another by one or more substituents selected from the group consisting of
fluorine.

In another embodiment of the present invention
R$^5$ is selected from the group GR5.2 consisting of
R$^6$R$^7$N—CO— and R$^8$—CO—(R$^9$)N—.

In another embodiment of the present invention
R$^5$ is selected from the group GR5.3 consisting of
R$^6$R$^7$N—CO—.

In another embodiment of the present invention
R$^6$, R$^7$ are selected from the group GR6/11.2 consisting of R$^8$, R$^9$
H—, F$_3$C—, HF$_2$C—, FH$_2$C—, F$_3$C—CH$_2$—, C$_{1-8}$-alkyl-, C$_{1-6}$-alkyl-S—C$_{1-3}$-alkyl-, C$_{3-7}$
R$^{10}$, R$^{11}$ -cycloalkyl-, C$_{3-7}$-cycloalkyl-C$_{1-6}$-alkyl-, C$_{6-12}$-polycycloalkyl-, aryl-, aryl-C$_{1-6}$-alkyl-, heterocyclyl-, heterocyclyl-C$_{1-6}$-alkyl-, heteroaryl-, heteroaryl-C$_{1-6}$-alkyl-, and R$^{14}$—O—C$_{1-3}$-alkyl-,
wherein, if R$^6$ and R$^7$ or R$^{10}$ and R$^{11}$ are C$_{1-6}$-alkyl groups, those two C$_{1-6}$-alkyl groups bound to the same nitrogen atom of R$^5$ may be joined together forming, together with the nitrogen atom to which they are bound, a 3 to 7 membered heterocyclic ring, and
wherein the above-mentioned members of the group GR6/11.2 including the heterocyclic ring formed by the R$^6$ and R$^7$ or R$^{10}$ and R$^{11}$ C$_{1-6}$-alkyl groups and the nitrogen atom of R$^5$ may optionally be substituted independently of one another by one or more substituents selected from group GR6/11.S2 consisting of
fluorine, chlorine, bromine, HO—, NC—, F$_3$C—, HF$_2$C—, FH$_2$C—, F$_3$C—CH$_2$—, F$_3$C—CH$_2$—, HO—$C_{1-6}$-alkyl-, $C_{1-6}$-alkyl-O—$C_{1-6}$-alkyl-, $C_{1-6}$-alkyl-, $C_{1-6}$-alkyl-O—, and aryl-,
  wherein the above-mentioned aryl of group GR6/11.S2 may optionally be substituted independently of one another by one or more substituents selected from group consisting of fluorine, chlorine, bromine, NC—, $F_3C$—, $HF_2C$—, $FH_2C$—, HO—$C_{1-3}$-alkyl-, $C_{1-3}$-alkyl-, and $C_{1-3}$-alkyl-O—.

In another embodiment of the present invention
$R^6$, $R^7$ are selected from the group GR6/7.3 consisting of
  H, $C_{1-8}$-alkyl-, $C_{3-6}$-cycloalkyl-, $C_{3-6}$-cycloalkyl-$C_{1-3}$-alkyl-, heterocyclyl-$C_{1-6}$-alkyl-, $C_{6-12}$-polycycloalkyl-, aryl-$C_{1-6}$-alkyl-, and $R^{14}$—O—$C_{1-3}$-alkyl-,
  wherein the above-mentioned members of the group GR6/7.3 may optionally be substituted independently of one another by one or more substituents selected from the group consisting of
  fluorine, HO—, NC—, $C_{1-3}$-alkyl-, $HO_2C$—, $C_{1-3}$-alkyl-O—C(O)—, HO—$C_{1-6}$-alkyl-, $C_{1-4}$-alkyl-O—$C_{1-3}$-alkyl-, and $C_{1-3}$-alkyl-O—

In another embodiment of the present invention
$R^6$ is selected from the group GR6.4 consisting of
  $C_{1-6}$-alkyl-, $C_{5-6}$-cycloalkyl-, heterocyclyl-$C_{1-6}$-alkyl-, and $C_{6-12}$-polycycloalkyl-,
  wherein the above-mentioned members of the group GR6.4 may optionally be substituted independently of one another by one or more substituents selected from the group consisting of
  fluorine, hydroxymethyl, methoxy-, methoxymethyl- and $H_3C$—.

In another embodiment of the present invention
$R^7$ is selected from the group GR7.4 consisting of
  $C_{1-4}$-alkyl-, cyclopropyl-, cyclopropyl-$C_{1-3}$-alkyl-
  wherein the above-mentioned members of the group GR7.4 may optionally be substituted independently of one another by one or more substituents selected from the group consisting of
  fluorine, CN—, HO—, and $H_3C$—O—.

In another embodiment of the present invention
$R^8$ is selected from the group GR8.3 consisting of
  $C_{1-6}$-alkyl-, $C_{3-6}$-cycloalkyl-, and $C_{3-6}$-cycloalkyl-$C_{1-3}$-alkyl-,
  wherein the above-mentioned members of the group GR8.3 may optionally be substituted independently of one another by one or more substituents selected from the group consisting of fluorine, HO—, NC—, phenyl- and $H_3C$—,
  wherein the above-mentioned phenyl group may optionally be substituted with one or more chlorines.

In another embodiment of the present invention
$R^8$ is selected from the group GR8.4 consisting of
  $C_{3-6}$-alkyl-, and $C_{5-6}$-cycloalkyl-,
  wherein the above-mentioned members of the group GR8.4 may optionally be substituted independently of one another by one or more substituents selected from the group consisting of
  fluorine, and $H_3C$—.

In another embodiment of the present invention
$R^9$ is selected from the group GR9.3 consisting of
  H—, $F_3C$—$CH_2$—, $C_{1-6}$-alkyl-,
  wherein the above-mentioned members of the group GR9.3 may optionally be substituted independently of one another by one or more substituents selected from the group consisting of
  fluorine.

In another embodiment of the present invention
$R^9$ is selected from the group GR9.4 consisting of
  H—.

In another embodiment of the present invention
$R^{10}$ is selected from the group GR10.3 consisting of
  H—, $C_{1-8}$-alkyl-, $C_{3-7}$-cycloalkyl-, $C_{3-7}$-cycloalkyl-$C_{1-6}$-alkyl-,
  wherein, $R^{10}$ and $R^{11}$ are $C_{1-6}$-alkyl groups, those two $C_{1-6}$-alkyl groups bound to the same nitrogen atom of $R^5$ may be joined together forming, together with the nitrogen atom to which they are bound, a 3 to 7 membered heterocyclic ring, and
  wherein the above-mentioned members of the group GR10.3 including the heterocyclic ring formed by the $R^{10}$ and $R^{11}$ $C_{1-6}$-alkyl groups and the nitrogen atom of $R^5$ may optionally be substituted independently of one another by one or more substituents selected from the group consisting of fluorine.

In another embodiment of the present invention
$R^{11}$ is selected from the group GR11.3 consisting of
  $C_{1-8}$-alkyl-, $C_{3-7}$-cycloalkyl-, $C_{3-7}$-cycloalkyl-$C_{1-6}$-alkyl-,
  wherein, $R^{10}$ and $R^{11}$ are $C_{1-6}$-alkyl groups, those two $C_{1-6}$-alkyl groups bound to the same nitrogen atom of $R^5$ may be joined together forming, together with the nitrogen atom to which they are bound, a 3 to 7 membered heterocyclic ring, and
  wherein the above-mentioned members of the group GR11.3 including the heterocyclic ring formed by the $R^{10}$ and $R^{11}$ $C_{1-6}$-alkyl groups and the nitrogen atom of $R^5$ may optionally be substituted independently of one another by one or more substituents selected from the group consisting of fluorine.

In another embodiment of the present invention
$R^{12}$ is selected from the group GR12.2 consisting of
  $F_3C$—, $HF_2C$—, $FH_2C$—, $C_{1-6}$-alkyl-, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, and heteroaryl-$C_{1-6}$-alkyl-,
  wherein the above-mentioned members of the group GR12.2 may optionally be substituted independently of one another by one or more substituents selected from the group consisting of
  fluorine, chlorine, bromine, HO—, NC—, $F_3C$—, $HF_2C$—, $FH_2C$—, $F_3C$—$CH_2$—, HO—$C_{1-3}$-alkyl-, $C_{1-4}$-alkyl-O—$C_{1-3}$-alkyl-, $C_{1-3}$-alkyl-, and $C_{1-3}$-alkyl-O—.

In another embodiment of the present invention
$R^{12}$ is selected from the group GR12.3 consisting of
  $C_{1-6}$-alkyl-, $C_{3-7}$-cycloalkyl-, $C_{3-7}$-cycloalkyl-$C_{1-6}$-alkyl-, aryl-, heterocyclyl-, and heteroaryl-
  wherein the above-mentioned members of the group GR12.3 may optionally be substituted independently of one another by one or more substituents selected from the group consisting of
  fluorine, chlorine, bromine, NC—, $F_3C$—, $HF_2C$—, $FH_2C$—, $F_3C$—$CH_2$—, $C_{1-3}$-alkyl-, and $C_{1-3}$-alkyl-O—.

In another embodiment of the present invention
$R^{12}$ is selected from the group GR12.4 consisting of
  phenyl-, wherein the above-mentioned members of the group GR12.4 may optionally be substituted independently of one another by one or more substituents selected from the group consisting of
  fluorine, chlorine, bromine, NC—, $F_3C$—, $HF_2C$—, $FH_2C$—, $F_3C$—$CH_2$—, $C_{1-3}$-alkyl-, and $C_{1-3}$-alkyl-O—.

In another embodiment of the present invention
$R^{13}$ is selected from the group GR13.2 consisting of
$H$—, $F_3C$—$CH_2$—, $C_{1-6}$-alkyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl-, and heteroaryl-$C_{1-3}$-alkyl-,
wherein two $C_{1-6}$-alkyl groups bound to the same nitrogen atom may be joined together forming, together with the nitrogen atom to which they are bound, a 3 to 7 membered heterocyclic ring, and
wherein the above-mentioned members of the group GR13.2 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, HO—$C_{1-6}$-alkyl-, $C_{1-4}$-alkyl-O—$C_{1-3}$-alkyl-, $C_{1-6}$-alkyl-, and $C_{1-6}$-alkyl-O—.

In another embodiment of the present invention
$R^{13}$ is selected from the group GR13.3 consisting of
$H$—, $F_3C$—$CH_2$—, $C_{1-6}$-alkyl-, $C_{3-7}$-cycloalkyl- and $C_{3-7}$-cycloalkyl-$C_{1-3}$-alkyl-,
wherein two $C_{1-6}$-alkyl groups bound to the same nitrogen atom may be joined together forming, together with the nitrogen atom to which they are bound, a 3 to 7 membered heterocyclic ring, and
wherein the above-mentioned members of the group GR13.3 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, HO—$C_{1-6}$-alkyl-, $C_{1-6}$-alkyl-, and $C_{1-6}$-alkyl-O—.

In another embodiment of the present invention
$R^{13}$ is selected from the group GR13.4 consisting of
$H$—, $C_{1-6}$-alkyl-,
wherein the above-mentioned members of the group GR13.4 may optionally be substituted independently of one another by one or more substituents selected from the group consisting of
fluorine.

In another embodiment of the present invention
$R^{14}$ is selected from the group GR14.2 consisting of
$H$—, $F_3C$—, $HF_2C$—, $FH_2C$—, $F_3C$—$CH_2$—, $C_{1-6}$-alkyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl- and heteroaryl-$C_{1-3}$-alkyl-,
wherein the above-mentioned members of the group GR14.2 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, $C_{1-3}$-alkyl-, and $C_{1-6}$-alkyl-O—, In another embodiment of the present invention
$R^{14}$ is selected from the group GR14.3 consisting of
$H$—, $C_{1-6}$-alkyl-, $C_{3-7}$-cycloalkyl-, $C_{3-7}$-cycloalkyl-$C_{1-3}$-alkyl-, wherein the above-mentioned members of the group GR14.3 may optionally be substituted independently of one another by one or more substituents selected from the group consisting of
fluorine, chlorine, bromine, HO—, NC—, $C_{1-3}$-alkyl-, and $C_{1-6}$-alkyl-O—, In another embodiment of the present invention
$R^{14}$ is selected from the group GR14.4 consisting of
$C_{1-6}$-alkyl-, wherein the above-mentioned members of the group GR14.4 may optionally be substituted independently of one another by one or more substituents selected from the group consisting of
fluorine, In another embodiment of the present invention i=0.

Any and each of the above definitions for A, i and $R^1$ to $R^{14}$ may be combined with each other.

In another embodiment compounds according to the invention are compounds according to formula 1,
wherein
A is selected from the group GA.4,
wherein the above-mentioned members of the group GA.4 may optionally be substituted independently of one another by one or more substituents selected from the group consisting of
fluorine, chlorine, $CH_3$—O—, $C_2H_5$—O—.
i is 0,
$R^1$ is selected from the group GR1.2,
$R^2$ is selected from the group GR2.4,
$R^3$ is selected from the group GR3.4,
wherein the above-mentioned members of the group GR3.4 may optionally be substituted independently of one another by one or more substituents selected from the group consisting of
fluorine, chlorine, bromine, NC—, $F_3C$—, $HF_2C$—, $FH_2C$—, $F_3C$—$CH_2$—, $C_{1-3}$-alkyl-, $CH_3$—O—$C_{1-3}$-alkyl-, and $C_{1-3}$-alkyl-O—,
$R^4$ is selected from the group GR4.4,
wherein the above-mentioned members of the group GR4.4 may optionally be substituted independently of one another by one or more substituents selected from the group consisting of fluorine,
$R^5$ is selected from the group GR5.2, preferably GR5.3,
$R^6$ is selected from the group GR6.4,
wherein the above-mentioned members of the group GR6.4 may optionally be substituted independently of one another by one or more substituents selected from the group consisting of
fluorine, hydroxymethyl, methoxy-, methoxymethyl- and $H_3C$—.
$R^7$ is selected from the group GR7.4,
wherein the above-mentioned members of the group GR7.4 may optionally be substituted independently of one another by one or more substituents selected from the group consisting of
fluorine, CN—, HO—, and $H_3C$—O—.
$R^8$ is selected from the group GR8.4,
wherein the above-mentioned members of the group GR8.4 may optionally be substituted independently of one another by one or more substituents selected from the group consisting of
fluorine, and $H_3C$—.
$R^9$ is selected from the group GR9.4
and pharmaceutically acceptable salts thereof.

In another embodiment compounds according to the invention are compounds according to formula 1A,

1A wherein
i, $R^2$, $R^3$, $R^4$, $R^7$, $R^{12}$, $R^{13}$ and $R^{14}$ have the meanings given hereinbefore and pharmaceutically acceptable salts thereof.

Another embodiment of the present invention are compounds of formula 1A wherein $R^2$, $R^3$, $R^4$, $R^7$, $R^{12}$, $R^{13}$ and $R^{14}$, are defined as in table 1 below and pharmaceutically acceptable salts thereof.

TABLE 1

| Group No. | $R^2$ | $R^3$ | $R^4$ | $R^7$ | $R^{12}$ | $R^{13}$ | $R^{14}$ |
|---|---|---|---|---|---|---|---|
| 1. a | GR2.3 | GR3.3 | GR4.3 | GR6/7.3 | GR12.3 | GR13.3 | GR14.3 |
| 2. a | GR2.3 | GR3.3 | GR4.3 | GR6/7.3 | GR12.4 | GR13.3 | GR14.3 |
| 3. a | GR2.3 | GR3.3 | GR4.3 | GR7.4 | GR12.3 | GR13.3 | GR14.3 |
| 4. a | GR2.3 | GR3.3 | GR4.3 | GR7.4 | GR12.4 | GR13.3 | GR14.3 |
| 5. a | GR2.3 | GR3.3 | GR4.4 | GR6/7.3 | GR12.3 | GR13.3 | GR14.3 |
| 6. a | GR2.3 | GR3.3 | GR4.4 | GR6/7.3 | GR12.4 | GR13.3 | GR14.3 |
| 7. a | GR2.3 | GR3.3 | GR4.4 | GR7.4 | GR12.3 | GR13.3 | GR14.3 |
| 8. a | GR2.3 | GR3.3 | GR4.4 | GR7.4 | GR12.4 | GR13.3 | GR14.3 |
| 9. a | GR2.3 | GR3.4 | GR4.3 | GR6/7.3 | GR12.3 | GR13.3 | GR14.3 |
| 10. a | GR2.3 | GR3.4 | GR4.3 | GR6/7.3 | GR12.4 | GR13.3 | GR14.3 |
| 11. a | GR2.3 | GR3.4 | GR4.3 | GR7.4 | GR12.3 | GR13.3 | GR14.3 |
| 12. a | GR2.3 | GR3.4 | GR4.3 | GR7.4 | GR12.4 | GR13.3 | GR14.3 |
| 13. a | GR2.3 | GR3.4 | GR4.4 | GR6/7.3 | GR12.3 | GR13.3 | GR14.3 |
| 14. a | GR2.3 | GR3.4 | GR4.4 | GR6/7.3 | GR12.4 | GR13.3 | GR14.3 |
| 15. a | GR2.3 | GR3.4 | GR4.4 | GR7.4 | GR12.3 | GR13.3 | GR14.3 |
| 16. a | GR2.3 | GR3.4 | GR4.4 | GR7.4 | GR12.4 | GR13.3 | GR14.3 |
| 17. a | GR2.4 | GR3.3 | GR4.3 | GR6/7.3 | GR12.3 | GR13.3 | GR14.3 |
| 18. a | GR2.4 | GR3.3 | GR4.3 | GR6/7.3 | GR12.4 | GR13.3 | GR14.3 |
| 19. a | GR2.4 | GR3.3 | GR4.3 | GR7.4 | GR12.3 | GR13.3 | GR14.3 |
| 20. a | GR2.4 | GR3.3 | GR4.3 | GR7.4 | GR12.4 | GR13.3 | GR14.3 |
| 21. a | GR2.4 | GR3.3 | GR4.4 | GR6/7.3 | GR12.3 | GR13.3 | GR14.3 |
| 22. a | GR2.4 | GR3.3 | GR4.4 | GR6/7.3 | GR12.4 | GR13.3 | GR14.3 |
| 23. a | GR2.4 | GR3.3 | GR4.4 | GR7.4 | GR12.3 | GR13.3 | GR14.3 |
| 24. a | GR2.4 | GR3.3 | GR4.4 | GR7.4 | GR12.4 | GR13.3 | GR14.3 |
| 25. a | GR2.4 | GR3.4 | GR4.3 | GR6/7.3 | GR12.3 | GR13.3 | GR14.3 |
| 26. a | GR2.4 | GR3.4 | GR4.3 | GR6/7.3 | GR12.4 | GR13.3 | GR14.3 |
| 27. a | GR2.4 | GR3.4 | GR4.3 | GR7.4 | GR12.3 | GR13.3 | GR14.3 |
| 28. a | GR2.4 | GR3.4 | GR4.3 | GR7.4 | GR12.4 | GR13.3 | GR14.3 |
| 29. a | GR2.4 | GR3.4 | GR4.4 | GR6/7.3 | GR12.3 | GR13.3 | GR14.3 |
| 30. a | GR2.4 | GR3.4 | GR4.4 | GR6/7.3 | GR12.4 | GR13.3 | GR14.3 |
| 31. a | GR2.4 | GR3.4 | GR4.4 | GR7.4 | GR12.3 | GR13.3 | GR14.3 |
| 32. a | GR2.4 | GR3.4 | GR4.4 | GR7.4 | GR12.4 | GR13.3 | GR14.3 |
| 33. a | GR2.3 | GR3.3 | GR4.3 | GR6/7.3 | GR12.3 | GR13.4 | GR14.3 |
| 34. a | GR2.3 | GR3.3 | GR4.3 | GR6/7.3 | GR12.4 | GR13.4 | GR14.3 |
| 35. a | GR2.3 | GR3.3 | GR4.3 | GR7.4 | GR12.3 | GR13.4 | GR14.3 |
| 36. a | GR2.3 | GR3.3 | GR4.3 | GR7.4 | GR12.4 | GR13.4 | GR14.3 |
| 37. a | GR2.3 | GR3.3 | GR4.4 | GR6/7.3 | GR12.3 | GR13.4 | GR14.3 |
| 38. a | GR2.3 | GR3.3 | GR4.4 | GR6/7.3 | GR12.4 | GR13.4 | GR14.3 |
| 39. a | GR2.3 | GR3.3 | GR4.4 | GR7.4 | GR12.3 | GR13.4 | GR14.3 |
| 40. a | GR2.3 | GR3.3 | GR4.4 | GR7.4 | GR12.4 | GR13.4 | GR14.3 |
| 41. a | GR2.3 | GR3.4 | GR4.3 | GR6/7.3 | GR12.3 | GR13.4 | GR14.3 |
| 42. a | GR2.3 | GR3.4 | GR4.3 | GR6/7.3 | GR12.4 | GR13.4 | GR14.3 |
| 43. a | GR2.3 | GR3.4 | GR4.3 | GR7.4 | GR12.3 | GR13.4 | GR14.3 |
| 44. a | GR2.3 | GR3.4 | GR4.3 | GR7.4 | GR12.4 | GR13.4 | GR14.3 |
| 45. a | GR2.3 | GR3.4 | GR4.4 | GR6/7.3 | GR12.3 | GR13.4 | GR14.3 |
| 46. a | GR2.3 | GR3.4 | GR4.4 | GR6/7.3 | GR12.4 | GR13.4 | GR14.3 |
| 47. a | GR2.3 | GR3.4 | GR4.4 | GR7.4 | GR12.3 | GR13.4 | GR14.3 |
| 48. a | GR2.3 | GR3.4 | GR4.4 | GR7.4 | GR12.4 | GR13.4 | GR14.3 |
| 49. a | GR2.4 | GR3.3 | GR4.3 | GR6/7.3 | GR12.3 | GR13.4 | GR14.3 |
| 50. a | GR2.4 | GR3.3 | GR4.3 | GR6/7.3 | GR12.4 | GR13.4 | GR14.3 |
| 51. a | GR2.4 | GR3.3 | GR4.3 | GR7.4 | GR12.3 | GR13.4 | GR14.3 |
| 52. a | GR2.4 | GR3.3 | GR4.3 | GR7.4 | GR12.4 | GR13.4 | GR14.3 |
| 53. a | GR2.4 | GR3.3 | GR4.4 | GR6/7.3 | GR12.3 | GR13.4 | GR14.3 |
| 54. a | GR2.4 | GR3.3 | GR4.4 | GR6/7.3 | GR12.4 | GR13.4 | GR14.3 |
| 55. a | GR2.4 | GR3.3 | GR4.4 | GR7.4 | GR12.3 | GR13.4 | GR14.3 |
| 56. a | GR2.4 | GR3.3 | GR4.4 | GR7.4 | GR12.4 | GR13.4 | GR14.3 |
| 57. a | GR2.4 | GR3.4 | GR4.3 | GR6/7.3 | GR12.3 | GR13.4 | GR14.3 |
| 58. a | GR2.4 | GR3.4 | GR4.3 | GR6/7.3 | GR12.4 | GR13.4 | GR14.3 |
| 59. a | GR2.4 | GR3.4 | GR4.3 | GR7.4 | GR12.3 | GR13.4 | GR14.3 |
| 60. a | GR2.4 | GR3.4 | GR4.3 | GR7.4 | GR12.4 | GR13.4 | GR14.3 |
| 61. a | GR2.4 | GR3.4 | GR4.4 | GR6/7.3 | GR12.3 | GR13.4 | GR14.3 |
| 62. a | GR2.4 | GR3.4 | GR4.4 | GR6/7.3 | GR12.4 | GR13.4 | GR14.3 |
| 63. a | GR2.4 | GR3.4 | GR4.4 | GR7.4 | GR12.3 | GR13.4 | GR14.3 |

TABLE 1-continued

| Group No. | R² | R³ | R⁴ | R⁷ | R¹² | R¹³ | R¹⁴ |
|---|---|---|---|---|---|---|---|
| 64. a | GR2.4 | GR3.4 | GR4.4 | GR7.4 | GR12.4 | GR13.4 | GR14.3 |
| 65. a | GR2.3 | GR3.3 | GR4.3 | GR6/7.3 | GR12.3 | GR13.3 | GR14.4 |
| 66. a | GR2.3 | GR3.3 | GR4.3 | GR6/7.3 | GR12.4 | GR13.3 | GR14.4 |
| 67. a | GR2.3 | GR3.3 | GR4.3 | GR7.4 | GR12.3 | GR13.3 | GR14.4 |
| 68. a | GR2.3 | GR3.3 | GR4.3 | GR7.4 | GR12.4 | GR13.3 | GR14.4 |
| 69. a | GR2.3 | GR3.3 | GR4.4 | GR6/7.3 | GR12.3 | GR13.3 | GR14.4 |
| 70. a | GR2.3 | GR3.3 | GR4.4 | GR6/7.3 | GR12.4 | GR13.3 | GR14.4 |
| 71. a | GR2.3 | GR3.3 | GR4.4 | GR7.4 | GR12.3 | GR13.3 | GR14.4 |
| 72. a | GR2.3 | GR3.3 | GR4.4 | GR7.4 | GR12.4 | GR13.3 | GR14.4 |
| 73. a | GR2.3 | GR3.4 | GR4.3 | GR6/7.3 | GR12.3 | GR13.3 | GR14.4 |
| 74. a | GR2.3 | GR3.4 | GR4.3 | GR6/7.3 | GR12.4 | GR13.3 | GR14.4 |
| 75. a | GR2.3 | GR3.4 | GR4.3 | GR7.4 | GR12.3 | GR13.3 | GR14.4 |
| 76. a | GR2.3 | GR3.4 | GR4.3 | GR7.4 | GR12.4 | GR13.3 | GR14.4 |
| 77. a | GR2.3 | GR3.4 | GR4.4 | GR6/7.3 | GR12.3 | GR13.3 | GR14.4 |
| 78. a | GR2.3 | GR3.4 | GR4.4 | GR6/7.3 | GR12.4 | GR13.3 | GR14.4 |
| 79. a | GR2.3 | GR3.4 | GR4.4 | GR7.4 | GR12.3 | GR13.3 | GR14.4 |
| 80. a | GR2.3 | GR3.4 | GR4.4 | GR7.4 | GR12.4 | GR13.3 | GR14.4 |
| 81. a | GR2.4 | GR3.3 | GR4.3 | GR6/7.3 | GR12.3 | GR13.3 | GR14.4 |
| 82. a | GR2.4 | GR3.3 | GR4.3 | GR6/7.3 | GR12.4 | GR13.3 | GR14.4 |
| 83. a | GR2.4 | GR3.3 | GR4.3 | GR7.4 | GR12.3 | GR13.3 | GR14.4 |
| 84. a | GR2.4 | GR3.3 | GR4.3 | GR7.4 | GR12.4 | GR13.3 | GR14.4 |
| 85. a | GR2.4 | GR3.3 | GR4.4 | GR6/7.3 | GR12.3 | GR13.3 | GR14.4 |
| 86. a | GR2.4 | GR3.3 | GR4.4 | GR6/7.3 | GR12.4 | GR13.3 | GR14.4 |
| 87. a | GR2.4 | GR3.3 | GR4.4 | GR7.4 | GR12.3 | GR13.3 | GR14.4 |
| 88. a | GR2.4 | GR3.3 | GR4.4 | GR7.4 | GR12.4 | GR13.3 | GR14.4 |
| 89. a | GR2.4 | GR3.4 | GR4.3 | GR6/7.3 | GR12.3 | GR13.3 | GR14.4 |
| 90. a | GR2.4 | GR3.4 | GR4.3 | GR6/7.3 | GR12.4 | GR13.3 | GR14.4 |
| 91. a | GR2.4 | GR3.4 | GR4.3 | GR7.4 | GR12.3 | GR13.3 | GR14.4 |
| 92. a | GR2.4 | GR3.4 | GR4.3 | GR7.4 | GR12.4 | GR13.3 | GR14.4 |
| 93. a | GR2.4 | GR3.4 | GR4.4 | GR6/7.3 | GR12.3 | GR13.3 | GR14.4 |
| 94. a | GR2.4 | GR3.4 | GR4.4 | GR6/7.3 | GR12.4 | GR13.3 | GR14.4 |
| 95. a | GR2.4 | GR3.4 | GR4.4 | GR7.4 | GR12.3 | GR13.3 | GR14.4 |
| 96. a | GR2.4 | GR3.4 | GR4.4 | GR7.4 | GR12.4 | GR13.3 | GR14.4 |
| 97. a | GR2.3 | GR3.3 | GR4.3 | GR6/7.3 | GR12.3 | GR13.4 | GR14.4 |
| 98. a | GR2.3 | GR3.3 | GR4.3 | GR6/7.3 | GR12.4 | GR13.4 | GR14.4 |
| 99. a | GR2.3 | GR3.3 | GR4.3 | GR7.4 | GR12.3 | GR13.4 | GR14.4 |
| 100. a | GR2.3 | GR3.3 | GR4.3 | GR7.4 | GR12.4 | GR13.4 | GR14.4 |
| 101. a | GR2.3 | GR3.3 | GR4.4 | GR6/7.3 | GR12.3 | GR13.4 | GR14.4 |
| 102. a | GR2.3 | GR3.3 | GR4.4 | GR6/7.3 | GR12.4 | GR13.4 | GR14.4 |
| 103. a | GR2.3 | GR3.3 | GR4.4 | GR7.4 | GR12.3 | GR13.4 | GR14.4 |
| 104. a | GR2.3 | GR3.3 | GR4.4 | GR7.4 | GR12.4 | GR13.4 | GR14.4 |
| 105. a | GR2.3 | GR3.4 | GR4.3 | GR6/7.3 | GR12.3 | GR13.4 | GR14.4 |
| 106. a | GR2.3 | GR3.4 | GR4.3 | GR6/7.3 | GR12.4 | GR13.4 | GR14.4 |
| 107. a | GR2.3 | GR3.4 | GR4.3 | GR7.4 | GR12.3 | GR13.4 | GR14.4 |
| 108. a | GR2.3 | GR3.4 | GR4.3 | GR7.4 | GR12.4 | GR13.4 | GR14.4 |
| 109. a | GR2.3 | GR3.4 | GR4.4 | GR6/7.3 | GR12.3 | GR13.4 | GR14.4 |
| 110. a | GR2.3 | GR3.4 | GR4.4 | GR6/7.3 | GR12.4 | GR13.4 | GR14.4 |
| 111. a | GR2.3 | GR3.4 | GR4.4 | GR7.4 | GR12.3 | GR13.4 | GR14.4 |
| 112. a | GR2.3 | GR3.4 | GR4.4 | GR7.4 | GR12.4 | GR13.4 | GR14.4 |
| 113. a | GR2.4 | GR3.3 | GR4.3 | GR6/7.3 | GR12.3 | GR13.4 | GR14.4 |
| 114. a | GR2.4 | GR3.3 | GR4.3 | GR6/7.3 | GR12.4 | GR13.4 | GR14.4 |
| 115. a | GR2.4 | GR3.3 | GR4.3 | GR7.4 | GR12.3 | GR13.4 | GR14.4 |
| 116. a | GR2.4 | GR3.3 | GR4.3 | GR7.4 | GR12.4 | GR13.4 | GR14.4 |
| 117. a | GR2.4 | GR3.3 | GR4.4 | GR6/7.3 | GR12.3 | GR13.4 | GR14.4 |
| 118. a | GR2.4 | GR3.3 | GR4.4 | GR6/7.3 | GR12.4 | GR13.4 | GR14.4 |
| 119. a | GR2.4 | GR3.3 | GR4.4 | GR7.4 | GR12.3 | GR13.4 | GR14.4 |
| 120. a | GR2.4 | GR3.3 | GR4.4 | GR7.4 | GR12.4 | GR13.4 | GR14.4 |
| 121. a | GR2.4 | GR3.4 | GR4.3 | GR6/7.3 | GR12.3 | GR13.4 | GR14.4 |
| 122. a | GR2.4 | GR3.4 | GR4.3 | GR6/7.3 | GR12.4 | GR13.4 | GR14.4 |
| 123. a | GR2.4 | GR3.4 | GR4.3 | GR7.4 | GR12.3 | GR13.4 | GR14.4 |
| 124. a | GR2.4 | GR3.4 | GR4.3 | GR7.4 | GR12.4 | GR13.4 | GR14.4 |
| 125. a | GR2.4 | GR3.4 | GR4.4 | GR6/7.3 | GR12.3 | GR13.4 | GR14.4 |
| 126. a | GR2.4 | GR3.4 | GR4.4 | GR6/7.3 | GR12.4 | GR13.4 | GR14.4 |
| 127. a | GR2.4 | GR3.4 | GR4.4 | GR7.4 | GR12.3 | GR13.4 | GR14.4 |
| 128. a | GR2.4 | GR3.4 | GR4.4 | GR7.4 | GR12.4 | GR13.4 | GR14.4 |

Another embodiment of the present invention are compounds of formula 1A wherein i=0 and $R^2$, $R^3$, $R^4$, $R^7$, $R^{12}$, $R^{13}$ and $R^{14}$, are defined as in table 1 above and pharmaceutically acceptable salts thereof.

Another embodiment of the present invention are compounds according to formula 1B,

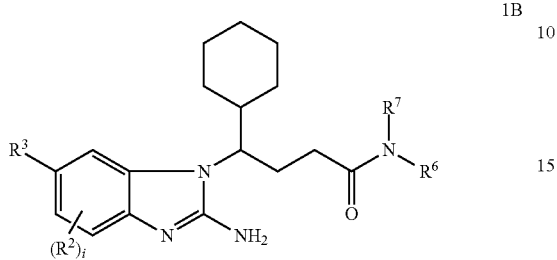

wherein
i, $R^2$, $R^3$, $R^6$, $R^7$, $R^{12}$, $R^{13}$ and $R^{14}$ have the meanings given hereinbefore and pharmaceutically acceptable salts thereof.

Another embodiment of the present invention are compounds of formula 1B wherein $R^2$, $R^3$, $R^6$, $R^7$, $R^{12}$, $R^{13}$ and $R^{14}$, are defined as in table 2 below and pharmaceutically acceptable salts thereof.

TABLE 2

| Group No. | $R^2$ | $R^3$ | $R^6$ | $R^7$ | $R^{12}$ | $R^{13}$ | $R^{14}$ |
|---|---|---|---|---|---|---|---|
| 1. b | GR2.3 | GR3.3 | GR6/7.3 | GR6/7.3 | GR12.3 | GR13.3 | GR14.3 |
| 2. b | GR2.3 | GR3.3 | GR6/7.3 | GR6/7.3 | GR12.4 | GR13.3 | GR14.3 |
| 3. b | GR2.3 | GR3.3 | GR6/7.3 | GR7.4 | GR12.3 | GR13.3 | GR14.3 |
| 4. b | GR2.3 | GR3.3 | GR6/7.3 | GR7.4 | GR12.4 | GR13.3 | GR14.3 |
| 5. b | GR2.3 | GR3.3 | GR6.4 | GR6/7.3 | GR12.3 | GR13.3 | GR14.3 |
| 6. b | GR2.3 | GR3.3 | GR6.4 | GR6/7.3 | GR12.4 | GR13.3 | GR14.3 |
| 7. b | GR2.3 | GR3.3 | GR6.4 | GR7.4 | GR12.3 | GR13.3 | GR14.3 |
| 8. b | GR2.3 | GR3.3 | GR6.4 | GR7.4 | GR12.4 | GR13.3 | GR14.3 |
| 9. b | GR2.3 | GR3.4 | GR6/7.3 | GR6/7.3 | GR12.3 | GR13.3 | GR14.3 |
| 10. b | GR2.3 | GR3.4 | GR6/7.3 | GR6/7.3 | GR12.4 | GR13.3 | GR14.3 |
| 11. b | GR2.3 | GR3.4 | GR6/7.3 | GR7.4 | GR12.3 | GR13.3 | GR14.3 |
| 12. b | GR2.3 | GR3.4 | GR6/7.3 | GR7.4 | GR12.4 | GR13.3 | GR14.3 |
| 13. b | GR2.3 | GR3.4 | GR6.4 | GR6/7.3 | GR12.3 | GR13.3 | GR14.3 |
| 14. b | GR2.3 | GR3.4 | GR6.4 | GR6/7.3 | GR12.4 | GR13.3 | GR14.3 |
| 15. b | GR2.3 | GR3.4 | GR6.4 | GR7.4 | GR12.3 | GR13.3 | GR14.3 |
| 16. b | GR2.3 | GR3.4 | GR6.4 | GR7.4 | GR12.4 | GR13.3 | GR14.3 |
| 17. b | GR2.4 | GR3.3 | GR6/7.3 | GR6/7.3 | GR12.3 | GR13.3 | GR14.3 |
| 18. b | GR2.4 | GR3.3 | GR6/7.3 | GR6/7.3 | GR12.4 | GR13.3 | GR14.3 |
| 19. b | GR2.4 | GR3.3 | GR6/7.3 | GR7.4 | GR12.3 | GR13.3 | GR14.3 |
| 20. b | GR2.4 | GR3.3 | GR6/7.3 | GR7.4 | GR12.4 | GR13.3 | GR14.3 |
| 21. b | GR2.4 | GR3.3 | GR6.4 | GR6/7.3 | GR12.3 | GR13.3 | GR14.3 |
| 22. b | GR2.4 | GR3.3 | GR6.4 | GR6/7.3 | GR12.4 | GR13.3 | GR14.3 |
| 23. b | GR2.4 | GR3.3 | GR6.4 | GR7.4 | GR12.3 | GR13.3 | GR14.3 |
| 24. b | GR2.4 | GR3.3 | GR6.4 | GR7.4 | GR12.4 | GR13.3 | GR14.3 |
| 25. b | GR2.4 | GR3.4 | GR6/7.3 | GR6/7.3 | GR12.3 | GR13.3 | GR14.3 |
| 26. b | GR2.4 | GR3.4 | GR6/7.3 | GR6/7.3 | GR12.4 | GR13.3 | GR14.3 |
| 27. b | GR2.4 | GR3.4 | GR6/7.3 | GR7.4 | GR12.3 | GR13.3 | GR14.3 |
| 28. b | GR2.4 | GR3.4 | GR6/7.3 | GR7.4 | GR12.4 | GR13.3 | GR14.3 |
| 29. b | GR2.4 | GR3.4 | GR6.4 | GR6/7.3 | GR12.3 | GR13.3 | GR14.3 |
| 30. b | GR2.4 | GR3.4 | GR6.4 | GR6/7.3 | GR12.4 | GR13.3 | GR14.3 |
| 31. b | GR2.4 | GR3.4 | GR6.4 | GR7.4 | GR12.3 | GR13.3 | GR14.3 |
| 32. b | GR2.4 | GR3.4 | GR6.4 | GR7.4 | GR12.4 | GR13.3 | GR14.3 |
| 33. b | GR2.3 | GR3.3 | GR6/7.3 | GR6/7.3 | GR12.3 | GR13.4 | GR14.3 |
| 34. b | GR2.3 | GR3.3 | GR6/7.3 | GR6/7.3 | GR12.4 | GR13.4 | GR14.3 |
| 35. b | GR2.3 | GR3.3 | GR6/7.3 | GR7.4 | GR12.3 | GR13.4 | GR14.3 |
| 36. b | GR2.3 | GR3.3 | GR6/7.3 | GR7.4 | GR12.4 | GR13.4 | GR14.3 |
| 37. b | GR2.3 | GR3.3 | GR6.4 | GR6/7.3 | GR12.3 | GR13.4 | GR14.3 |
| 38. b | GR2.3 | GR3.3 | GR6.4 | GR6/7.3 | GR12.4 | GR13.4 | GR14.3 |
| 39. b | GR2.3 | GR3.3 | GR6.4 | GR7.4 | GR12.3 | GR13.4 | GR14.3 |
| 40. b | GR2.3 | GR3.3 | GR6.4 | GR7.4 | GR12.4 | GR13.4 | GR14.3 |
| 41. b | GR2.3 | GR3.4 | GR6/7.3 | GR6/7.3 | GR12.3 | GR13.4 | GR14.3 |
| 42. b | GR2.3 | GR3.4 | GR6/7.3 | GR6/7.3 | GR12.4 | GR13.4 | GR14.3 |

TABLE 2-continued

| Group No. | R² | R³ | R⁶ | R⁷ | R¹² | R¹³ | R¹⁴ |
|---|---|---|---|---|---|---|---|
| 43. b | GR2.3 | GR3.4 | GR6/7.3 | GR7.4 | GR12.3 | GR13.4 | GR14.3 |
| 44. b | GR2.3 | GR3.4 | GR6/7.3 | GR7.4 | GR12.4 | GR13.4 | GR14.3 |
| 45. b | GR2.3 | GR3.4 | GR6.4 | GR6/7.3 | GR12.3 | GR13.4 | GR14.3 |
| 46. b | GR2.3 | GR3.4 | GR6.4 | GR6/7.3 | GR12.4 | GR13.4 | GR14.3 |
| 47. b | GR2.3 | GR3.4 | GR6.4 | GR7.4 | GR12.3 | GR13.4 | GR14.3 |
| 48. b | GR2.3 | GR3.4 | GR6.4 | GR7.4 | GR12.4 | GR13.4 | GR14.3 |
| 49. b | GR2.4 | GR3.3 | GR6/7.3 | GR6/7.3 | GR12.3 | GR13.4 | GR14.3 |
| 50. b | GR2.4 | GR3.3 | GR6/7.3 | GR6/7.3 | GR12.4 | GR13.4 | GR14.3 |
| 51. b | GR2.4 | GR3.3 | GR6/7.3 | GR7.4 | GR12.3 | GR13.4 | GR14.3 |
| 52. b | GR2.4 | GR3.3 | GR6/7.3 | GR7.4 | GR12.4 | GR13.4 | GR14.3 |
| 53. b | GR2.4 | GR3.3 | GR6.4 | GR6/7.3 | GR12.3 | GR13.4 | GR14.3 |
| 54. b | GR2.4 | GR3.3 | GR6.4 | GR6/7.3 | GR12.4 | GR13.4 | GR14.3 |
| 55. b | GR2.4 | GR3.3 | GR6.4 | GR7.4 | GR12.3 | GR13.4 | GR14.3 |
| 56. b | GR2.4 | GR3.3 | GR6.4 | GR7.4 | GR12.4 | GR13.4 | GR14.3 |
| 57. b | GR2.4 | GR3.4 | GR6/7.3 | GR6/7.3 | GR12.3 | GR13.4 | GR14.3 |
| 58. b | GR2.4 | GR3.4 | GR6/7.3 | GR6/7.3 | GR12.4 | GR13.4 | GR14.3 |
| 59. b | GR2.4 | GR3.4 | GR6/7.3 | GR7.4 | GR12.3 | GR13.4 | GR14.3 |
| 60. b | GR2.4 | GR3.4 | GR6/7.3 | GR7.4 | GR12.4 | GR13.4 | GR14.3 |
| 61. b | GR2.4 | GR3.4 | GR6.4 | GR6/7.3 | GR12.3 | GR13.4 | GR14.3 |
| 62. b | GR2.4 | GR3.4 | GR6.4 | GR6/7.3 | GR12.4 | GR13.4 | GR14.3 |
| 63. b | GR2.4 | GR3.4 | GR6.4 | GR7.4 | GR12.3 | GR13.4 | GR14.3 |
| 64. b | GR2.4 | GR3.4 | GR6.4 | GR7.4 | GR12.4 | GR13.4 | GR14.3 |
| 65. b | GR2.3 | GR3.3 | GR6/7.3 | GR6/7.3 | GR12.3 | GR13.3 | GR14.4 |
| 66. b | GR2.3 | GR3.3 | GR6/7.3 | GR6/7.3 | GR12.4 | GR13.3 | GR14.4 |
| 67. b | GR2.3 | GR3.3 | GR6/7.3 | GR7.4 | GR12.3 | GR13.3 | GR14.4 |
| 68. b | GR2.3 | GR3.3 | GR6/7.3 | GR7.4 | GR12.4 | GR13.3 | GR14.4 |
| 69. b | GR2.3 | GR3.3 | GR6.4 | GR6/7.3 | GR12.3 | GR13.3 | GR14.4 |
| 70. b | GR2.3 | GR3.3 | GR6.4 | GR6/7.3 | GR12.4 | GR13.3 | GR14.4 |
| 71. b | GR2.3 | GR3.3 | GR6.4 | GR7.4 | GR12.3 | GR13.3 | GR14.4 |
| 72. b | GR2.3 | GR3.3 | GR6.4 | GR7.4 | GR12.4 | GR13.3 | GR14.4 |
| 73. b | GR2.3 | GR3.4 | GR6/7.3 | GR6/7.3 | GR12.3 | GR13.3 | GR14.4 |
| 74. b | GR2.3 | GR3.4 | GR6/7.3 | GR6/7.3 | GR12.4 | GR13.3 | GR14.4 |
| 75. b | GR2.3 | GR3.4 | GR6/7.3 | GR7.4 | GR12.3 | GR13.3 | GR14.4 |
| 76. b | GR2.3 | GR3.4 | GR6/7.3 | GR7.4 | GR12.4 | GR13.3 | GR14.4 |
| 77. b | GR2.3 | GR3.4 | GR6.4 | GR6/7.3 | GR12.3 | GR13.3 | GR14.4 |
| 78. b | GR2.3 | GR3.4 | GR6.4 | GR6/7.3 | GR12.4 | GR13.3 | GR14.4 |
| 79. b | GR2.3 | GR3.4 | GR6.4 | GR7.4 | GR12.3 | GR13.3 | GR14.4 |
| 80. b | GR2.3 | GR3.4 | GR6.4 | GR7.4 | GR12.4 | GR13.3 | GR14.4 |
| 81. b | GR2.4 | GR3.3 | GR6/7.3 | GR6/7.3 | GR12.3 | GR13.3 | GR14.4 |
| 82. b | GR2.4 | GR3.3 | GR6/7.3 | GR6/7.3 | GR12.4 | GR13.3 | GR14.4 |
| 83. b | GR2.4 | GR3.3 | GR6/7.3 | GR7.4 | GR12.3 | GR13.3 | GR14.4 |
| 84. b | GR2.4 | GR3.3 | GR6/7.3 | GR7.4 | GR12.4 | GR13.3 | GR14.4 |
| 85. b | GR2.4 | GR3.3 | GR6.4 | GR6/7.3 | GR12.3 | GR13.3 | GR14.4 |
| 86. b | GR2.4 | GR3.3 | GR6.4 | GR6/7.3 | GR12.4 | GR13.3 | GR14.4 |
| 87. b | GR2.4 | GR3.3 | GR6.4 | GR7.4 | GR12.3 | GR13.3 | GR14.4 |
| 88. b | GR2.4 | GR3.3 | GR6.4 | GR7.4 | GR12.4 | GR13.3 | GR14.4 |
| 89. b | GR2.4 | GR3.4 | GR6/7.3 | GR6/7.3 | GR12.3 | GR13.3 | GR14.4 |
| 90. b | GR2.4 | GR3.4 | GR6/7.3 | GR6/7.3 | GR12.4 | GR13.3 | GR14.4 |
| 91. b | GR2.4 | GR3.4 | GR6/7.3 | GR7.4 | GR12.3 | GR13.3 | GR14.4 |
| 92. b | GR2.4 | GR3.4 | GR6/7.3 | GR7.4 | GR12.4 | GR13.3 | GR14.4 |
| 93. b | GR2.4 | GR3.4 | GR6.4 | GR6/7.3 | GR12.3 | GR13.3 | GR14.4 |
| 94. b | GR2.4 | GR3.4 | GR6.4 | GR6/7.3 | GR12.4 | GR13.3 | GR14.4 |
| 95. b | GR2.4 | GR3.4 | GR6.4 | GR7.4 | GR12.3 | GR13.3 | GR14.4 |
| 96. b | GR2.4 | GR3.4 | GR6.4 | GR7.4 | GR12.4 | GR13.3 | GR14.4 |
| 97. b | GR2.3 | GR3.3 | GR6/7.3 | GR6/7.3 | GR12.3 | GR13.4 | GR14.4 |
| 98. b | GR2.3 | GR3.3 | GR6/7.3 | GR6/7.3 | GR12.4 | GR13.4 | GR14.4 |
| 99. b | GR2.3 | GR3.3 | GR6/7.3 | GR7.4 | GR12.3 | GR13.4 | GR14.4 |
| 100. b | GR2.3 | GR3.3 | GR6/7.3 | GR7.4 | GR12.4 | GR13.4 | GR14.4 |
| 101. b | GR2.3 | GR3.3 | GR6.4 | GR6/7.3 | GR12.3 | GR13.4 | GR14.4 |
| 102. b | GR2.3 | GR3.3 | GR6.4 | GR6/7.3 | GR12.4 | GR13.4 | GR14.4 |
| 103. b | GR2.3 | GR3.3 | GR6.4 | GR7.4 | GR12.3 | GR13.4 | GR14.4 |
| 104. b | GR2.3 | GR3.3 | GR6.4 | GR7.4 | GR12.4 | GR13.4 | GR14.4 |
| 105. b | GR2.3 | GR3.4 | GR6/7.3 | GR6/7.3 | GR12.3 | GR13.4 | GR14.4 |
| 106. b | GR2.3 | GR3.4 | GR6/7.3 | GR6/7.3 | GR12.4 | GR13.4 | GR14.4 |
| 107. b | GR2.3 | GR3.4 | GR6/7.3 | GR7.4 | GR12.3 | GR13.4 | GR14.4 |
| 108. b | GR2.3 | GR3.4 | GR6/7.3 | GR7.4 | GR12.4 | GR13.4 | GR14.4 |
| 109. b | GR2.3 | GR3.4 | GR6.4 | GR6/7.3 | GR12.3 | GR13.4 | GR14.4 |
| 110. b | GR2.3 | GR3.4 | GR6.4 | GR6/7.3 | GR12.4 | GR13.4 | GR14.4 |
| 111. b | GR2.3 | GR3.4 | GR6.4 | GR7.4 | GR12.3 | GR13.4 | GR14.4 |
| 112. b | GR2.3 | GR3.4 | GR6.4 | GR7.4 | GR12.4 | GR13.4 | GR14.4 |
| 113. b | GR2.4 | GR3.3 | GR6/7.3 | GR6/7.3 | GR12.3 | GR13.4 | GR14.4 |
| 114. b | GR2.4 | GR3.3 | GR6/7.3 | GR6/7.3 | GR12.4 | GR13.4 | GR14.4 |
| 115. b | GR2.4 | GR3.3 | GR6/7.3 | GR7.4 | GR12.3 | GR13.4 | GR14.4 |
| 116. b | GR2.4 | GR3.3 | GR6/7.3 | GR7.4 | GR12.4 | GR13.4 | GR14.4 |
| 117. b | GR2.4 | GR3.3 | GR6.4 | GR6/7.3 | GR12.3 | GR13.4 | GR14.4 |
| 118. b | GR2.4 | GR3.3 | GR6.4 | GR6/7.3 | GR12.4 | GR13.4 | GR14.4 |
| 119. b | GR2.4 | GR3.3 | GR6.4 | GR7.4 | GR12.3 | GR13.4 | GR14.4 |

TABLE 2-continued

| Group No. | $R^2$ | $R^3$ | $R^6$ | $R^7$ | $R^{12}$ | $R^{13}$ | $R^{14}$ |
|---|---|---|---|---|---|---|---|
| 120. b | GR2.4 | GR3.3 | GR6.4 | GR7.4 | GR12.4 | GR13.4 | GR14.4 |
| 121. b | GR2.4 | GR3.4 | GR6/7.3 | GR6/7.3 | GR12.3 | GR13.4 | GR14.4 |
| 122. b | GR2.4 | GR3.4 | GR6/7.3 | GR6/7.3 | GR12.4 | GR13.4 | GR14.4 |
| 123. b | GR2.4 | GR3.4 | GR6/7.3 | GR7.4 | GR12.3 | GR13.4 | GR14.4 |
| 124. b | GR2.4 | GR3.4 | GR6/7.3 | GR7.4 | GR12.4 | GR13.4 | GR14.4 |
| 125. b | GR2.4 | GR3.4 | GR6.4 | GR6/7.3 | GR12.3 | GR13.4 | GR14.4 |
| 126. b | GR2.4 | GR3.4 | GR6.4 | GR6/7.3 | GR12.4 | GR13.4 | GR14.4 |
| 127. b | GR2.4 | GR3.4 | GR6.4 | GR7.4 | GR12.3 | GR13.4 | GR14.4 |
| 128. b | GR2.4 | GR3.4 | GR6.4 | GR7.4 | GR12.4 | GR13.4 | GR14.4 |

Another embodiment of the present invention are compounds of formula 1B wherein i=0 and $R^2$, $R^3$, $R^6$, $R^7$, $R^{12}$, $R^{13}$ and $R^{14}$, are defined as in table 2 above and pharmaceutically acceptable salts thereof.

Another embodiment of the present invention are compounds according to formula 1C,

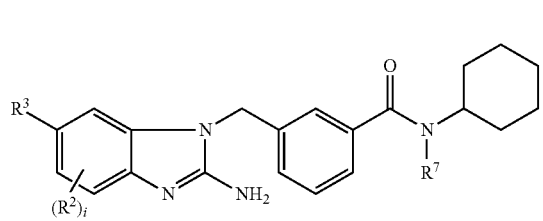

1C wherein
i, $R^2$, $R^3$, $R^7$, $R^{12}$, $R^{13}$ and $R^{14}$ have the meanings given hereinbefore and pharmaceutically acceptable salts thereof.

Another embodiment of the present invention are such compounds of formula 1c wherein $R^2$, $R^3$, $R^7$, $R^{12}$, $R^{13}$ and $R^{14}$, are defined as in table 3 below and pharmaceutically acceptable salts thereof.

TABLE 3

| Group No. | $R^2$ | $R^3$ | $R^{7b}$ | $R^{12}$ | $R^{13}$ | $R^{14}$ |
|---|---|---|---|---|---|---|
| 1. c | GR2.3 | GR3.3 | GR6/7.3 | GR12.3 | GR13.3 | GR14.3 |
| 2. c | GR2.3 | GR3.3 | GR6/7.3 | GR12.4 | GR13.3 | GR14.3 |
| 3. c | GR2.3 | GR3.3 | GR7.4 | GR12.3 | GR13.3 | GR14.3 |
| 4. c | GR2.3 | GR3.3 | GR7.4 | GR12.4 | GR13.3 | GR14.3 |
| 5. c | GR2.3 | GR3.4 | GR6/7.3 | GR12.3 | GR13.3 | GR14.3 |
| 6. c | GR2.3 | GR3.4 | GR6/7.3 | GR12.4 | GR13.3 | GR14.3 |
| 7. c | GR2.3 | GR3.4 | GR7.4 | GR12.3 | GR13.3 | GR14.3 |
| 8. c | GR2.3 | GR3.4 | GR7.4 | GR12.4 | GR13.3 | GR14.3 |
| 9. c | GR2.4 | GR3.3 | GR6/7.3 | GR12.3 | GR13.3 | GR14.3 |
| 10. c | GR2.4 | GR3.3 | GR6/7.3 | GR12.4 | GR13.3 | GR14.3 |
| 11. c | GR2.4 | GR3.3 | GR7.4 | GR12.3 | GR13.3 | GR14.3 |
| 12. c | GR2.4 | GR3.3 | GR7.4 | GR12.4 | GR13.3 | GR14.3 |
| 13. c | GR2.4 | GR3.4 | GR6/7.3 | GR12.3 | GR13.3 | GR14.3 |
| 14. c | GR2.4 | GR3.4 | GR6/7.3 | GR12.4 | GR13.3 | GR14.3 |
| 15. c | GR2.4 | GR3.4 | GR7.4 | GR12.3 | GR13.3 | GR14.3 |
| 16. c | GR2.4 | GR3.4 | GR7.4 | GR12.4 | GR13.3 | GR14.3 |
| 17. c | GR2.3 | GR3.3 | GR6/7.3 | GR12.3 | GR13.4 | GR14.3 |
| 18. c | GR2.3 | GR3.3 | GR6/7.3 | GR12.4 | GR13.4 | GR14.3 |
| 19. c | GR2.3 | GR3.3 | GR7.4 | GR12.3 | GR13.4 | GR14.3 |
| 20. c | GR2.3 | GR3.3 | GR7.4 | GR12.4 | GR13.4 | GR14.3 |
| 21. c | GR2.3 | GR3.4 | GR6/7.3 | GR12.3 | GR13.4 | GR14.3 |
| 22. c | GR2.3 | GR3.4 | GR6/7.3 | GR12.4 | GR13.4 | GR14.3 |
| 23. c | GR2.3 | GR3.4 | GR7.4 | GR12.3 | GR13.4 | GR14.3 |
| 24. c | GR2.3 | GR3.4 | GR7.4 | GR12.4 | GR13.4 | GR14.3 |
| 25. c | GR2.4 | GR3.3 | GR6/7.3 | GR12.3 | GR13.4 | GR14.3 |
| 26. c | GR2.4 | GR3.3 | GR6/7.3 | GR12.4 | GR13.4 | GR14.3 |
| 27. c | GR2.4 | GR3.3 | GR7.4 | GR12.3 | GR13.4 | GR14.3 |
| 28. c | GR2.4 | GR3.3 | GR7.4 | GR12.4 | GR13.4 | GR14.3 |
| 29. c | GR2.4 | GR3.4 | GR6/7.3 | GR12.3 | GR13.4 | GR14.3 |
| 30. c | GR2.4 | GR3.4 | GR6/7.3 | GR12.4 | GR13.4 | GR14.3 |
| 31. c | GR2.4 | GR3.4 | GR7.4 | GR12.3 | GR13.4 | GR14.3 |
| 32. c | GR2.4 | GR3.4 | GR7.4 | GR12.4 | GR13.4 | GR14.3 |
| 33. c | GR2.3 | GR3.3 | GR6/7.3 | GR12.3 | GR13.3 | GR14.4 |
| 34. c | GR2.3 | GR3.3 | GR6/7.3 | GR12.4 | GR13.3 | GR14.4 |
| 35. c | GR2.3 | GR3.3 | GR7.4 | GR12.3 | GR13.3 | GR14.4 |
| 36. c | GR2.3 | GR3.3 | GR7.4 | GR12.4 | GR13.3 | GR14.4 |
| 37. c | GR2.3 | GR3.4 | GR6/7.3 | GR12.3 | GR13.3 | GR14.4 |
| 38. c | GR2.3 | GR3.4 | GR6/7.3 | GR12.4 | GR13.3 | GR14.4 |
| 39. c | GR2.3 | GR3.4 | GR7.4 | GR12.3 | GR13.3 | GR14.4 |
| 40. c | GR2.3 | GR3.4 | GR7.4 | GR12.4 | GR13.3 | GR14.4 |
| 41. c | GR2.4 | GR3.3 | GR6/7.3 | GR12.3 | GR13.3 | GR14.4 |
| 42. c | GR2.4 | GR3.3 | GR6/7.3 | GR12.4 | GR13.3 | GR14.4 |
| 43. c | GR2.4 | GR3.3 | GR7.4 | GR12.3 | GR13.3 | GR14.4 |
| 44. c | GR2.4 | GR3.3 | GR7.4 | GR12.4 | GR13.3 | GR14.4 |
| 45. c | GR2.4 | GR3.4 | GR6/7.3 | GR12.3 | GR13.3 | GR14.4 |
| 46. c | GR2.4 | GR3.4 | GR6/7.3 | GR12.4 | GR13.3 | GR14.4 |
| 47. c | GR2.4 | GR3.4 | GR7.4 | GR12.3 | GR13.3 | GR14.4 |
| 48. c | GR2.4 | GR3.4 | GR7.4 | GR12.4 | GR13.3 | GR14.4 |
| 49. c | GR2.3 | GR3.3 | GR6/7.3 | GR12.3 | GR13.4 | GR14.4 |
| 50. c | GR2.3 | GR3.3 | GR6/7.3 | GR12.4 | GR13.4 | GR14.4 |
| 51. c | GR2.3 | GR3.3 | GR7.4 | GR12.3 | GR13.4 | GR14.4 |
| 52. c | GR2.3 | GR3.3 | GR7.4 | GR12.4 | GR13.4 | GR14.4 |
| 53. c | GR2.3 | GR3.4 | GR6/7.3 | GR12.3 | GR13.4 | GR14.4 |
| 54. c | GR2.3 | GR3.4 | GR6/7.3 | GR12.4 | GR13.4 | GR14.4 |
| 55. c | GR2.3 | GR3.4 | GR7.4 | GR12.3 | GR13.4 | GR14.4 |
| 56. c | GR2.3 | GR3.4 | GR7.4 | GR12.4 | GR13.4 | GR14.4 |
| 57. c | GR2.4 | GR3.3 | GR6/7.3 | GR12.3 | GR13.4 | GR14.4 |
| 58. c | GR2.4 | GR3.3 | GR6/7.3 | GR12.4 | GR13.4 | GR14.4 |
| 59. c | GR2.4 | GR3.3 | GR7.4 | GR12.3 | GR13.4 | GR14.4 |
| 60. c | GR2.4 | GR3.3 | GR7.4 | GR12.4 | GR13.4 | GR14.4 |
| 61. c | GR2.4 | GR3.4 | GR6/7.3 | GR12.3 | GR13.4 | GR14.4 |
| 62. c | GR2.4 | GR3.4 | GR6/7.3 | GR12.4 | GR13.4 | GR14.4 |
| 63. c | GR2.4 | GR3.4 | GR7.4 | GR12.3 | GR13.4 | GR14.4 |
| 64. c | GR2.4 | GR3.4 | GR7.4 | GR12.4 | GR13.4 | GR14.4 |

Another embodiment of the present invention are such compounds of formula 1c wherein i=0 and $R^2$, $R^3$, $R^7$, $R^{12}$, $R^{13}$ and $R^{14}$, are defined as in table 3 above and pharmaceutically acceptable salts thereof.

Another embodiment of the present invention are according to formula 1D,

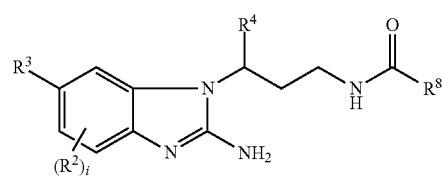

1D wherein
i, $R^2$, $R^3$, $R^4$, $R^8$, $R^{12}$, $R^{13}$ and $R^{14}$ have the meanings given hereinbefore and pharmaceutically acceptable salts thereof.

Another embodiment of the present invention are compounds of formula 1D wherein $R^2$, $R^3$, $R^4$, $R^8$, $R^{12}$, $R^{13}$ and $R^{14}$, are defined as in table 4 below and pharmaceutically acceptable salts thereof.

TABLE 4

| Group No. | $R^2$ | $R^3$ | $R^4$ | $R^8$ | $R^{12}$ | $R^{13}$ | $R^{14}$ |
|---|---|---|---|---|---|---|---|
| 1. d | GR2.3 | GR3.3 | GR4.3 | GR8.3 | GR12.3 | GR13.3 | GR14.3 |
| 2. d | GR2.3 | GR3.3 | GR4.3 | GR8.3 | GR12.4 | GR13.3 | GR14.3 |
| 3. d | GR2.3 | GR3.3 | GR4.3 | GR8.4 | GR12.3 | GR13.3 | GR14.3 |
| 4. d | GR2.3 | GR3.3 | GR4.3 | GR8.4 | GR12.4 | GR13.3 | GR14.3 |
| 5. d | GR2.3 | GR3.3 | GR4.4 | GR8.3 | GR12.3 | GR13.3 | GR14.3 |
| 6. d | GR2.3 | GR3.3 | GR4.4 | GR8.3 | GR12.4 | GR13.3 | GR14.3 |
| 7. d | GR2.3 | GR3.3 | GR4.4 | GR8.4 | GR12.3 | GR13.3 | GR14.3 |
| 8. d | GR2.3 | GR3.3 | GR4.4 | GR8.4 | GR12.4 | GR13.3 | GR14.3 |
| 9. d | GR2.3 | GR3.4 | GR4.3 | GR8.3 | GR12.3 | GR13.3 | GR14.3 |
| 10. d | GR2.3 | GR3.4 | GR4.3 | GR8.3 | GR12.4 | GR13.3 | GR14.3 |
| 11. d | GR2.3 | GR3.4 | GR4.3 | GR8.4 | GR12.3 | GR13.3 | GR14.3 |
| 12. d | GR2.3 | GR3.4 | GR4.3 | GR8.4 | GR12.4 | GR13.3 | GR14.3 |
| 13. d | GR2.3 | GR3.4 | GR4.4 | GR8.3 | GR12.3 | GR13.3 | GR14.3 |
| 14. d | GR2.3 | GR3.4 | GR4.4 | GR8.3 | GR12.4 | GR13.3 | GR14.3 |
| 15. d | GR2.3 | GR3.4 | GR4.4 | GR8.4 | GR12.3 | GR13.3 | GR14.3 |
| 16. d | GR2.3 | GR3.4 | GR4.4 | GR8.4 | GR12.4 | GR13.3 | GR14.3 |
| 17. d | GR2.4 | GR3.3 | GR4.3 | GR8.3 | GR12.3 | GR13.3 | GR14.3 |
| 18. d | GR2.4 | GR3.3 | GR4.3 | GR8.3 | GR12.4 | GR13.3 | GR14.3 |
| 19. d | GR2.4 | GR3.3 | GR4.3 | GR8.4 | GR12.3 | GR13.3 | GR14.3 |
| 20. d | GR2.4 | GR3.3 | GR4.3 | GR8.4 | GR12.4 | GR13.3 | GR14.3 |
| 21. d | GR2.4 | GR3.3 | GR4.4 | GR8.3 | GR12.3 | GR13.3 | GR14.3 |
| 22. d | GR2.4 | GR3.3 | GR4.4 | GR8.3 | GR12.4 | GR13.3 | GR14.3 |
| 23. d | GR2.4 | GR3.3 | GR4.4 | GR8.4 | GR12.3 | GR13.3 | GR14.3 |
| 24. d | GR2.4 | GR3.3 | GR4.4 | GR8.4 | GR12.4 | GR13.3 | GR14.3 |
| 25. d | GR2.4 | GR3.4 | GR4.3 | GR8.3 | GR12.3 | GR13.3 | GR14.3 |
| 26. d | GR2.4 | GR3.4 | GR4.3 | GR8.3 | GR12.4 | GR13.3 | GR14.3 |
| 27. d | GR2.4 | GR3.4 | GR4.3 | GR8.4 | GR12.3 | GR13.3 | GR14.3 |
| 28. d | GR2.4 | GR3.4 | GR4.3 | GR8.4 | GR12.4 | GR13.3 | GR14.3 |
| 29. d | GR2.4 | GR3.4 | GR4.4 | GR8.3 | GR12.3 | GR13.3 | GR14.3 |
| 30. d | GR2.4 | GR3.4 | GR4.4 | GR8.3 | GR12.4 | GR13.3 | GR14.3 |
| 31. d | GR2.4 | GR3.4 | GR4.4 | GR8.4 | GR12.3 | GR13.3 | GR14.3 |
| 32. d | GR2.4 | GR3.4 | GR4.4 | GR8.4 | GR12.4 | GR13.3 | GR14.3 |
| 33. d | GR2.3 | GR3.3 | GR4.3 | GR8.3 | GR12.3 | GR13.4 | GR14.3 |
| 34. d | GR2.3 | GR3.3 | GR4.3 | GR8.3 | GR12.4 | GR13.4 | GR14.3 |
| 35. d | GR2.3 | GR3.3 | GR4.3 | GR8.4 | GR12.3 | GR13.4 | GR14.3 |
| 36. d | GR2.3 | GR3.3 | GR4.3 | GR8.4 | GR12.4 | GR13.4 | GR14.3 |
| 37. d | GR2.3 | GR3.3 | GR4.4 | GR8.3 | GR12.3 | GR13.4 | GR14.3 |
| 38. d | GR2.3 | GR3.3 | GR4.4 | GR8.3 | GR12.4 | GR13.4 | GR14.3 |
| 39. d | GR2.3 | GR3.3 | GR4.4 | GR8.4 | GR12.3 | GR13.4 | GR14.3 |
| 40. d | GR2.3 | GR3.3 | GR4.4 | GR8.4 | GR12.4 | GR13.4 | GR14.3 |
| 41. d | GR2.3 | GR3.4 | GR4.3 | GR8.3 | GR12.3 | GR13.4 | GR14.3 |
| 42. d | GR2.3 | GR3.4 | GR4.3 | GR8.3 | GR12.4 | GR13.4 | GR14.3 |
| 43. d | GR2.3 | GR3.4 | GR4.3 | GR8.4 | GR12.3 | GR13.4 | GR14.3 |
| 44. d | GR2.3 | GR3.4 | GR4.3 | GR8.4 | GR12.4 | GR13.4 | GR14.3 |
| 45. d | GR2.3 | GR3.4 | GR4.4 | GR8.3 | GR12.3 | GR13.4 | GR14.3 |
| 46. d | GR2.3 | GR3.4 | GR4.4 | GR8.3 | GR12.4 | GR13.4 | GR14.3 |
| 47. d | GR2.3 | GR3.4 | GR4.4 | GR8.4 | GR12.3 | GR13.4 | GR14.3 |
| 48. d | GR2.3 | GR3.4 | GR4.4 | GR8.4 | GR12.4 | GR13.4 | GR14.3 |
| 49. d | GR2.4 | GR3.3 | GR4.3 | GR8.3 | GR12.3 | GR13.4 | GR14.3 |
| 50. d | GR2.4 | GR3.3 | GR4.3 | GR8.3 | GR12.4 | GR13.4 | GR14.3 |
| 51. d | GR2.4 | GR3.3 | GR4.3 | GR8.4 | GR12.3 | GR13.4 | GR14.3 |
| 52. d | GR2.4 | GR3.3 | GR4.3 | GR8.4 | GR12.4 | GR13.4 | GR14.3 |
| 53. d | GR2.4 | GR3.3 | GR4.4 | GR8.3 | GR12.3 | GR13.4 | GR14.3 |
| 54. d | GR2.4 | GR3.3 | GR4.4 | GR8.3 | GR12.4 | GR13.4 | GR14.3 |
| 55. d | GR2.4 | GR3.3 | GR4.4 | GR8.4 | GR12.3 | GR13.4 | GR14.3 |
| 56. d | GR2.4 | GR3.3 | GR4.4 | GR8.4 | GR12.4 | GR13.4 | GR14.3 |
| 57. d | GR2.4 | GR3.4 | GR4.3 | GR8.3 | GR12.3 | GR13.4 | GR14.3 |
| 58. d | GR2.4 | GR3.4 | GR4.3 | GR8.3 | GR12.4 | GR13.4 | GR14.3 |
| 59. d | GR2.4 | GR3.4 | GR4.3 | GR8.4 | GR12.3 | GR13.4 | GR14.3 |
| 60. d | GR2.4 | GR3.4 | GR4.3 | GR8.4 | GR12.4 | GR13.4 | GR14.3 |
| 61. d | GR2.4 | GR3.4 | GR4.4 | GR8.3 | GR12.3 | GR13.4 | GR14.3 |
| 62. d | GR2.4 | GR3.4 | GR4.4 | GR8.3 | GR12.4 | GR13.4 | GR14.3 |
| 63. d | GR2.4 | GR3.4 | GR4.4 | GR8.4 | GR12.3 | GR13.4 | GR14.3 |
| 64. d | GR2.4 | GR3.4 | GR4.4 | GR8.4 | GR12.4 | GR13.4 | GR14.3 |
| 65. d | GR2.3 | GR3.3 | GR4.3 | GR8.3 | GR12.3 | GR13.3 | GR14.4 |
| 66. d | GR2.3 | GR3.3 | GR4.3 | GR8.3 | GR12.4 | GR13.3 | GR14.4 |
| 67. d | GR2.3 | GR3.3 | GR4.3 | GR8.4 | GR12.3 | GR13.3 | GR14.4 |
| 68. d | GR2.3 | GR3.3 | GR4.3 | GR8.4 | GR12.4 | GR13.3 | GR14.4 |
| 69. d | GR2.3 | GR3.3 | GR4.4 | GR8.3 | GR12.3 | GR13.3 | GR14.4 |
| 70. d | GR2.3 | GR3.3 | GR4.4 | GR8.3 | GR12.4 | GR13.3 | GR14.4 |
| 71. d | GR2.3 | GR3.3 | GR4.4 | GR8.4 | GR12.3 | GR13.3 | GR14.4 |

TABLE 4-continued

| Group No. | R$^2$ | R$^3$ | R$^4$ | R$^8$ | R$^{12}$ | R$^{13}$ | R$^{14}$ |
|---|---|---|---|---|---|---|---|
| 72. d | GR2.3 | GR3.3 | GR4.4 | GR8.4 | GR12.4 | GR13.3 | GR14.4 |
| 73. d | GR2.3 | GR3.4 | GR4.3 | GR8.3 | GR12.3 | GR13.3 | GR14.4 |
| 74. d | GR2.3 | GR3.4 | GR4.3 | GR8.3 | GR12.4 | GR13.3 | GR14.4 |
| 75. d | GR2.3 | GR3.4 | GR4.3 | GR8.4 | GR12.3 | GR13.3 | GR14.4 |
| 76. d | GR2.3 | GR3.4 | GR4.3 | GR8.4 | GR12.4 | GR13.3 | GR14.4 |
| 77. d | GR2.3 | GR3.4 | GR4.4 | GR8.3 | GR12.3 | GR13.3 | GR14.4 |
| 78. d | GR2.3 | GR3.4 | GR4.4 | GR8.3 | GR12.4 | GR13.3 | GR14.4 |
| 79. d | GR2.3 | GR3.4 | GR4.4 | GR8.4 | GR12.3 | GR13.3 | GR14.4 |
| 80. d | GR2.3 | GR3.4 | GR4.4 | GR8.4 | GR12.4 | GR13.3 | GR14.4 |
| 81. d | GR2.4 | GR3.3 | GR4.3 | GR8.3 | GR12.3 | GR13.3 | GR14.4 |
| 82. d | GR2.4 | GR3.3 | GR4.3 | GR8.3 | GR12.4 | GR13.3 | GR14.4 |
| 83. d | GR2.4 | GR3.3 | GR4.3 | GR8.4 | GR12.3 | GR13.3 | GR14.4 |
| 84. d | GR2.4 | GR3.3 | GR4.3 | GR8.4 | GR12.4 | GR13.3 | GR14.4 |
| 85. d | GR2.4 | GR3.3 | GR4.4 | GR8.3 | GR12.3 | GR13.3 | GR14.4 |
| 86. d | GR2.4 | GR3.3 | GR4.4 | GR8.3 | GR12.4 | GR13.3 | GR14.4 |
| 87. d | GR2.4 | GR3.3 | GR4.4 | GR8.4 | GR12.3 | GR13.3 | GR14.4 |
| 88. d | GR2.4 | GR3.3 | GR4.4 | GR8.4 | GR12.4 | GR13.3 | GR14.4 |
| 89. d | GR2.4 | GR3.4 | GR4.3 | GR8.3 | GR12.3 | GR13.3 | GR14.4 |
| 90. d | GR2.4 | GR3.4 | GR4.3 | GR8.3 | GR12.4 | GR13.3 | GR14.4 |
| 91. d | GR2.4 | GR3.4 | GR4.3 | GR8.4 | GR12.3 | GR13.3 | GR14.4 |
| 92. d | GR2.4 | GR3.4 | GR4.3 | GR8.4 | GR12.4 | GR13.3 | GR14.4 |
| 93. d | GR2.4 | GR3.4 | GR4.4 | GR8.3 | GR12.3 | GR13.3 | GR14.4 |
| 94. d | GR2.4 | GR3.4 | GR4.4 | GR8.3 | GR12.4 | GR13.3 | GR14.4 |
| 95. d | GR2.4 | GR3.4 | GR4.4 | GR8.4 | GR12.3 | GR13.3 | GR14.4 |
| 96. d | GR2.4 | GR3.4 | GR4.4 | GR8.4 | GR12.4 | GR13.3 | GR14.4 |
| 97. d | GR2.3 | GR3.3 | GR4.3 | GR8.3 | GR12.3 | GR13.4 | GR14.4 |
| 98. d | GR2.3 | GR3.3 | GR4.3 | GR8.3 | GR12.4 | GR13.4 | GR14.4 |
| 99. d | GR2.3 | GR3.3 | GR4.3 | GR8.4 | GR12.3 | GR13.4 | GR14.4 |
| 100. d | GR2.3 | GR3.3 | GR4.3 | GR8.4 | GR12.4 | GR13.4 | GR14.4 |
| 101. d | GR2.3 | GR3.3 | GR4.4 | GR8.3 | GR12.3 | GR13.4 | GR14.4 |
| 102. d | GR2.3 | GR3.3 | GR4.4 | GR8.3 | GR12.4 | GR13.4 | GR14.4 |
| 103. d | GR2.3 | GR3.3 | GR4.4 | GR8.4 | GR12.3 | GR13.4 | GR14.4 |
| 104. d | GR2.3 | GR3.3 | GR4.4 | GR8.4 | GR12.4 | GR13.4 | GR14.4 |
| 105. d | GR2.3 | GR3.4 | GR4.3 | GR8.3 | GR12.3 | GR13.4 | GR14.4 |
| 106. d | GR2.3 | GR3.4 | GR4.3 | GR8.3 | GR12.4 | GR13.4 | GR14.4 |
| 107. d | GR2.3 | GR3.4 | GR4.3 | GR8.4 | GR12.3 | GR13.4 | GR14.4 |
| 108. d | GR2.3 | GR3.4 | GR4.3 | GR8.4 | GR12.4 | GR13.4 | GR14.4 |
| 109. d | GR2.3 | GR3.4 | GR4.4 | GR8.3 | GR12.3 | GR13.4 | GR14.4 |
| 110. d | GR2.3 | GR3.4 | GR4.4 | GR8.3 | GR12.4 | GR13.4 | GR14.4 |
| 111. d | GR2.3 | GR3.4 | GR4.4 | GR8.4 | GR12.3 | GR13.4 | GR14.4 |
| 112. d | GR2.3 | GR3.4 | GR4.4 | GR8.4 | GR12.4 | GR13.4 | GR14.4 |
| 113. d | GR2.4 | GR3.3 | GR4.3 | GR8.3 | GR12.3 | GR13.4 | GR14.4 |
| 114. d | GR2.4 | GR3.3 | GR4.3 | GR8.3 | GR12.4 | GR13.4 | GR14.4 |
| 115. d | GR2.4 | GR3.3 | GR4.3 | GR8.4 | GR12.3 | GR13.4 | GR14.4 |
| 116. d | GR2.4 | GR3.3 | GR4.3 | GR8.4 | GR12.4 | GR13.4 | GR14.4 |
| 117. d | GR2.4 | GR3.3 | GR4.4 | GR8.3 | GR12.3 | GR13.4 | GR14.4 |
| 118. d | GR2.4 | GR3.3 | GR4.4 | GR8.3 | GR12.4 | GR13.4 | GR14.4 |
| 119. d | GR2.4 | GR3.3 | GR4.4 | GR8.4 | GR12.3 | GR13.4 | GR14.4 |
| 120. d | GR2.4 | GR3.3 | GR4.4 | GR8.4 | GR12.4 | GR13.4 | GR14.4 |
| 121. d | GR2.4 | GR3.4 | GR4.3 | GR8.3 | GR12.3 | GR13.4 | GR14.4 |
| 122. d | GR2.4 | GR3.4 | GR4.3 | GR8.3 | GR12.4 | GR13.4 | GR14.4 |
| 123. d | GR2.4 | GR3.4 | GR4.3 | GR8.4 | GR12.3 | GR13.4 | GR14.4 |
| 124. d | GR2.4 | GR3.4 | GR4.3 | GR8.4 | GR12.4 | GR13.4 | GR14.4 |
| 125. d | GR2.4 | GR3.4 | GR4.4 | GR8.3 | GR12.3 | GR13.4 | GR14.4 |
| 126. d | GR2.4 | GR3.4 | GR4.4 | GR8.3 | GR12.4 | GR13.4 | GR14.4 |
| 127. d | GR2.4 | GR3.4 | GR4.4 | GR8.4 | GR12.3 | GR13.4 | GR14.4 |
| 128. d | GR2.4 | GR3.4 | GR4.4 | GR8.4 | GR12.4 | GR13.4 | GR14.4 |

Another embodiment of the present invention are compounds of formula 1D wherein i=0 and $R^2$, $R^3$, $R^4$, $R^8$, $R^{12}$, $R^{13}$ and $R^{14}$, are defined as in table 4 above and pharmaceutically acceptable salts thereof.

Another embodiment of the present invention are compounds according to formula 1E,

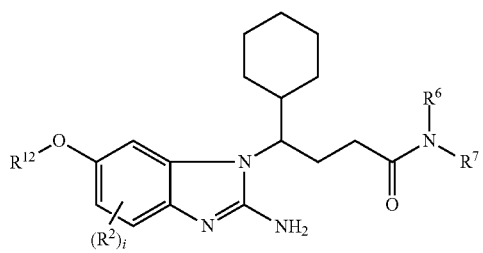

1E i, $R^2$, $R^6$, $R^7$, $R^{12}$, $R^{13}$ and $R^{14}$ have the meanings given hereinbefore and pharmaceutically acceptable salts thereof.

Another embodiment of the present invention are compounds of formula 1E wherein $R^2$, $R^6$, $R^7$, $R^{12}$, $R^{13}$ and $R^{14}$, are defined as in table 5 below and pharmaceutically acceptable salts thereof.

TABLE 5

| Group No. | $R^2$ | $R^6$ | $R^7$ | $R^{12}$ | $R^{13}$ | $R^{14}$ |
|---|---|---|---|---|---|---|
| 1. e | GR2.3 | GR6/7.3 | GR6/7.3 | GR12.3 | GR13.3 | GR14.3 |
| 2. e | GR2.3 | GR6/7.3 | GR6/7.3 | GR12.4 | GR13.3 | GR14.3 |
| 3. e | GR2.3 | GR6/7.3 | GR7.4 | GR12.3 | GR13.3 | GR14.3 |
| 4. e | GR2.3 | GR6/7.3 | GR7.4 | GR12.4 | GR13.3 | GR14.3 |
| 5. e | GR2.3 | GR6.4 | GR6/7.3 | GR12.3 | GR13.3 | GR14.3 |
| 6. e | GR2.3 | GR6.4 | GR6/7.3 | GR12.4 | GR13.3 | GR14.3 |
| 7. e | GR2.3 | GR6.4 | GR7.4 | GR12.3 | GR13.3 | GR14.3 |
| 8. e | GR2.3 | GR6.4 | GR7.4 | GR12.4 | GR13.3 | GR14.3 |
| 9. e | GR2.4 | GR6/7.3 | GR6/7.3 | GR12.3 | GR13.3 | GR14.3 |
| 10. e | GR2.4 | GR6/7.3 | GR6/7.3 | GR12.4 | GR13.3 | GR14.3 |
| 11. e | GR2.4 | GR6/7.3 | GR7.4 | GR12.3 | GR13.3 | GR14.3 |
| 12. e | GR2.4 | GR6/7.3 | GR7.4 | GR12.4 | GR13.3 | GR14.3 |
| 13. e | GR2.4 | GR6.4 | GR6/7.3 | GR12.3 | GR13.3 | GR14.3 |
| 14. e | GR2.4 | GR6.4 | GR6/7.3 | GR12.4 | GR13.3 | GR14.3 |
| 15. e | GR2.4 | GR6.4 | GR7.4 | GR12.3 | GR13.3 | GR14.3 |
| 16. e | GR2.4 | GR6.4 | GR7.4 | GR12.4 | GR13.3 | GR14.3 |
| 17. e | GR2.3 | GR6/7.3 | GR6/7.3 | GR12.3 | GR13.4 | GR14.3 |
| 18. e | GR2.3 | GR6/7.3 | GR6/7.3 | GR12.4 | GR13.4 | GR14.3 |
| 19. e | GR2.3 | GR6/7.3 | GR7.4 | GR12.3 | GR13.4 | GR14.3 |
| 20. e | GR2.3 | GR6/7.3 | GR7.4 | GR12.4 | GR13.4 | GR14.3 |
| 21. e | GR2.3 | GR6.4 | GR6/7.3 | GR12.3 | GR13.4 | GR14.3 |
| 22. e | GR2.3 | GR6.4 | GR6/7.3 | GR12.4 | GR13.4 | GR14.3 |
| 23. e | GR2.3 | GR6.4 | GR7.4 | GR12.3 | GR13.4 | GR14.3 |
| 24. e | GR2.3 | GR6.4 | GR7.4 | GR12.4 | GR13.4 | GR14.3 |
| 25. e | GR2.4 | GR6/7.3 | GR6/7.3 | GR12.3 | GR13.4 | GR14.3 |
| 26. e | GR2.4 | GR6/7.3 | GR6/7.3 | GR12.4 | GR13.4 | GR14.3 |
| 27. e | GR2.4 | GR6/7.3 | GR7.4 | GR12.3 | GR13.4 | GR14.3 |
| 28. e | GR2.4 | GR6/7.3 | GR7.4 | GR12.4 | GR13.4 | GR14.3 |
| 29. e | GR2.4 | GR6.4 | GR6/7.3 | GR12.3 | GR13.4 | GR14.3 |
| 30. e | GR2.4 | GR6.4 | GR6/7.3 | GR12.4 | GR13.4 | GR14.3 |
| 31. e | GR2.4 | GR6.4 | GR7.4 | GR12.3 | GR13.4 | GR14.3 |
| 32. e | GR2.4 | GR6.4 | GR7.4 | GR12.4 | GR13.4 | GR14.3 |
| 33. e | GR2.3 | GR6/7.3 | GR6/7.3 | GR12.3 | GR13.3 | GR14.4 |
| 34. e | GR2.3 | GR6/7.3 | GR6/7.3 | GR12.4 | GR13.3 | GR14.4 |
| 35. e | GR2.3 | GR6/7.3 | GR7.4 | GR12.3 | GR13.3 | GR14.4 |
| 36. e | GR2.3 | GR6/7.3 | GR7.4 | GR12.4 | GR13.3 | GR14.4 |
| 37. e | GR2.3 | GR6.4 | GR6/7.3 | GR12.3 | GR13.3 | GR14.4 |
| 38. e | GR2.3 | GR6.4 | GR6/7.3 | GR12.4 | GR13.3 | GR14.4 |
| 39. e | GR2.3 | GR6.4 | GR7.4 | GR12.3 | GR13.3 | GR14.4 |
| 40. e | GR2.3 | GR6.4 | GR7.4 | GR12.4 | GR13.3 | GR14.4 |
| 41. e | GR2.4 | GR6/7.3 | GR6/7.3 | GR12.3 | GR13.3 | GR14.4 |
| 42. e | GR2.4 | GR6/7.3 | GR6/7.3 | GR12.4 | GR13.3 | GR14.4 |
| 43. e | GR2.4 | GR6/7.3 | GR7.4 | GR12.3 | GR13.3 | GR14.4 |
| 44. e | GR2.4 | GR6/7.3 | GR7.4 | GR12.4 | GR13.3 | GR14.4 |
| 45. e | GR2.4 | GR6.4 | GR6/7.3 | GR12.3 | GR13.3 | GR14.4 |
| 46. e | GR2.4 | GR6.4 | GR6/7.3 | GR12.4 | GR13.3 | GR14.4 |
| 47. e | GR2.4 | GR6.4 | GR7.4 | GR12.3 | GR13.3 | GR14.4 |
| 48. e | GR2.4 | GR6.4 | GR7.4 | GR12.4 | GR13.3 | GR14.4 |
| 49. e | GR2.3 | GR6/7.3 | GR6/7.3 | GR12.3 | GR13.4 | GR14.4 |
| 50. e | GR2.3 | GR6/7.3 | GR6/7.3 | GR12.4 | GR13.4 | GR14.4 |
| 51. e | GR2.3 | GR6/7.3 | GR7.4 | GR12.3 | GR13.4 | GR14.4 |
| 52. e | GR2.3 | GR6/7.3 | GR7.4 | GR12.4 | GR13.4 | GR14.4 |
| 53. e | GR2.3 | GR6.4 | GR6/7.3 | GR12.3 | GR13.4 | GR14.4 |
| 54. e | GR2.3 | GR6.4 | GR6/7.3 | GR12.4 | GR13.4 | GR14.4 |
| 55. e | GR2.3 | GR6.4 | GR7.4 | GR12.3 | GR13.4 | GR14.4 |
| 56. e | GR2.3 | GR6.4 | GR7.4 | GR12.4 | GR13.4 | GR14.4 |
| 57. e | GR2.4 | GR6/7.3 | GR6/7.3 | GR12.3 | GR13.4 | GR14.4 |
| 58. e | GR2.4 | GR6/7.3 | GR6/7.3 | GR12.4 | GR13.4 | GR14.4 |
| 59. e | GR2.4 | GR6/7.3 | GR7.4 | GR12.3 | GR13.4 | GR14.4 |
| 60. e | GR2.4 | GR6/7.3 | GR7.4 | GR12.4 | GR13.4 | GR14.4 |
| 61. e | GR2.4 | GR6.4 | GR6/7.3 | GR12.3 | GR13.4 | GR14.4 |
| 62. e | GR2.4 | GR6.4 | GR6/7.3 | GR12.4 | GR13.4 | GR14.4 |
| 63. e | GR2.4 | GR6.4 | GR7.4 | GR12.3 | GR13.4 | GR14.4 |
| 64. e | GR2.4 | GR6.4 | GR7.4 | GR12.4 | GR13.4 | GR14.4 |

Another embodiment of the present invention are compounds of formula 1E wherein i=0 and $R^2$, $R^6$, $R^7$, $R^{12}$, $R^{13}$ and $R^{14}$, are defined as in table 5 above and pharmaceutically acceptable salts thereof.

Another embodiment of the present invention are compounds according to formula 1F,

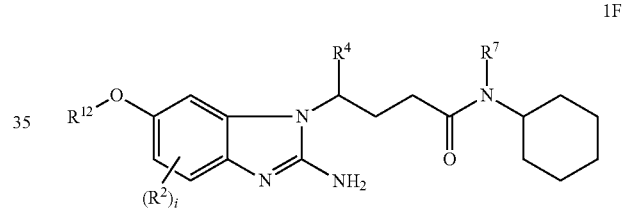

1F wherein
i, $R^2$, $R^4$, $R^7$, $R^{12}$, $R^{13}$ and $R^{14}$ have the meanings given hereinbefore and pharmaceutically acceptable salts thereof.

Another embodiment of the present invention are compounds of formula 1F wherein $R^2$, $R^4$, $R^7$, $R^{12}$, $R^{13}$ and $R^{14}$, are defined as in table 6 below and pharmaceutically acceptable salts thereof.

TABLE 6

| Group No. | $R^2$ | $R^4$ | $R^7$ | $R^{12}$ | $R^{13}$ | $R^{14}$ |
|---|---|---|---|---|---|---|
| 1. f | GR2.3 | GR4.3 | GR6/7.3 | GR12.3 | GR13.3 | GR14.3 |
| 2. f | GR2.3 | GR4.3 | GR6/7.3 | GR12.4 | GR13.3 | GR14.3 |
| 3. f | GR2.3 | GR4.3 | GR7.4 | GR12.3 | GR13.3 | GR14.3 |
| 4. f | GR2.3 | GR4.3 | GR7.4 | GR12.4 | GR13.3 | GR14.3 |
| 5. f | GR2.3 | GR4.4 | GR6/7.3 | GR12.3 | GR13.3 | GR14.3 |
| 6. f | GR2.3 | GR4.4 | GR6/7.3 | GR12.4 | GR13.3 | GR14.3 |
| 7. f | GR2.3 | GR4.4 | GR7.4 | GR12.3 | GR13.3 | GR14.3 |
| 8. f | GR2.3 | GR4.4 | GR7.4 | GR12.4 | GR13.3 | GR14.3 |
| 9. f | GR2.4 | GR4.3 | GR6/7.3 | GR12.3 | GR13.3 | GR14.3 |
| 10. f | GR2.4 | GR4.3 | GR6/7.3 | GR12.4 | GR13.3 | GR14.3 |
| 11. f | GR2.4 | GR4.3 | GR7.4 | GR12.3 | GR13.3 | GR14.3 |
| 12. f | GR2.4 | GR4.3 | GR7.4 | GR12.4 | GR13.3 | GR14.3 |
| 13. f | GR2.4 | GR4.4 | GR6/7.3 | GR12.3 | GR13.3 | GR14.3 |
| 14. f | GR2.4 | GR4.4 | GR6/7.3 | GR12.4 | GR13.3 | GR14.3 |
| 15. f | GR2.4 | GR4.4 | GR7.4 | GR12.3 | GR13.3 | GR14.3 |
| 16. f | GR2.4 | GR4.4 | GR7.4 | GR12.4 | GR13.3 | GR14.3 |
| 17. f | GR2.3 | GR4.3 | GR6/7.3 | GR12.3 | GR13.4 | GR14.3 |
| 18. f | GR2.3 | GR4.3 | GR6/7.3 | GR12.4 | GR13.4 | GR14.3 |

TABLE 6-continued

| Group No. | R² | R⁴ | R⁷ | R¹² | R¹³ | R¹⁴ |
|---|---|---|---|---|---|---|
| 19. f | GR2.3 | GR4.3 | GR7.4 | GR12.3 | GR13.4 | GR14.3 |
| 20. f | GR2.3 | GR4.3 | GR7.4 | GR12.4 | GR13.4 | GR14.3 |
| 21. f | GR2.3 | GR4.4 | GR6/7.3 | GR12.3 | GR13.4 | GR14.3 |
| 22. f | GR2.3 | GR4.4 | GR6/7.3 | GR12.4 | GR13.4 | GR14.3 |
| 23. f | GR2.3 | GR4.4 | GR7.4 | GR12.3 | GR13.4 | GR14.3 |
| 24. f | GR2.3 | GR4.4 | GR7.4 | GR12.4 | GR13.4 | GR14.3 |
| 25. f | GR2.4 | GR4.3 | GR6/7.3 | GR12.3 | GR13.4 | GR14.3 |
| 26. f | GR2.4 | GR4.3 | GR6/7.3 | GR12.4 | GR13.4 | GR14.3 |
| 27. f | GR2.4 | GR4.3 | GR7.4 | GR12.3 | GR13.4 | GR14.3 |
| 28. f | GR2.4 | GR4.3 | GR7.4 | GR12.4 | GR13.4 | GR14.3 |
| 29. f | GR2.4 | GR4.4 | GR6/7.3 | GR12.3 | GR13.4 | GR14.3 |
| 30. f | GR2.4 | GR4.4 | GR6/7.3 | GR12.4 | GR13.4 | GR14.3 |
| 31. f | GR2.4 | GR4.4 | GR7.4 | GR12.3 | GR13.4 | GR14.3 |
| 32. f | GR2.4 | GR4.4 | GR7.4 | GR12.4 | GR13.4 | GR14.3 |
| 33. f | GR2.3 | GR4.3 | GR6/7.3 | GR12.3 | GR13.3 | GR14.4 |
| 34. f | GR2.3 | GR4.3 | GR6/7.3 | GR12.4 | GR13.3 | GR14.4 |
| 35. f | GR2.3 | GR4.3 | GR7.4 | GR12.3 | GR13.3 | GR14.4 |
| 36. f | GR2.3 | GR4.3 | GR7.4 | GR12.4 | GR13.3 | GR14.4 |
| 37. f | GR2.3 | GR4.4 | GR6/7.3 | GR12.3 | GR13.3 | GR14.4 |
| 38. f | GR2.3 | GR4.4 | GR6/7.3 | GR12.4 | GR13.3 | GR14.4 |
| 39. f | GR2.3 | GR4.4 | GR7.4 | GR12.3 | GR13.3 | GR14.4 |
| 40. f | GR2.3 | GR4.4 | GR7.4 | GR12.4 | GR13.3 | GR14.4 |
| 41. f | GR2.4 | GR4.3 | GR6/7.3 | GR12.3 | GR13.3 | GR14.4 |
| 42. f | GR2.4 | GR4.3 | GR6/7.3 | GR12.4 | GR13.3 | GR14.4 |
| 43. f | GR2.4 | GR4.3 | GR7.4 | GR12.3 | GR13.3 | GR14.4 |
| 44. f | GR2.4 | GR4.3 | GR7.4 | GR12.4 | GR13.3 | GR14.4 |
| 45. f | GR2.4 | GR4.4 | GR6/7.3 | GR12.3 | GR13.3 | GR14.4 |
| 46. f | GR2.4 | GR4.4 | GR6/7.3 | GR12.4 | GR13.3 | GR14.4 |
| 47. f | GR2.4 | GR4.4 | GR7.4 | GR12.3 | GR13.3 | GR14.4 |
| 48. f | GR2.4 | GR4.4 | GR7.4 | GR12.4 | GR13.3 | GR14.4 |
| 49. f | GR2.3 | GR4.3 | GR6/7.3 | GR12.3 | GR13.4 | GR14.4 |
| 50. f | GR2.3 | GR4.3 | GR6/7.3 | GR12.4 | GR13.4 | GR14.4 |
| 51. f | GR2.3 | GR4.3 | GR7.4 | GR12.3 | GR13.4 | GR14.4 |
| 52. f | GR2.3 | GR4.3 | GR7.4 | GR12.4 | GR13.4 | GR14.4 |
| 53. f | GR2.3 | GR4.4 | GR6/7.3 | GR12.3 | GR13.4 | GR14.4 |
| 54. f | GR2.3 | GR4.4 | GR6/7.3 | GR12.4 | GR13.4 | GR14.4 |
| 55. f | GR2.3 | GR4.4 | GR7.4 | GR12.3 | GR13.4 | GR14.4 |
| 56. f | GR2.3 | GR4.4 | GR7.4 | GR12.4 | GR13.4 | GR14.4 |
| 57. f | GR2.4 | GR4.3 | GR6/7.3 | GR12.3 | GR13.4 | GR14.4 |
| 58. f | GR2.4 | GR4.3 | GR6/7.3 | GR12.4 | GR13.4 | GR14.4 |
| 59. f | GR2.4 | GR4.3 | GR7.4 | GR12.3 | GR13.4 | GR14.4 |
| 60. f | GR2.4 | GR4.3 | GR7.4 | GR12.4 | GR13.4 | GR14.4 |
| 61. f | GR2.4 | GR4.4 | GR6/7.3 | GR12.3 | GR13.4 | GR14.4 |
| 62. f | GR2.4 | GR4.4 | GR6/7.3 | GR12.4 | GR13.4 | GR14.4 |
| 63. f | GR2.4 | GR4.4 | GR7.4 | GR12.3 | GR13.4 | GR14.4 |
| 64. f | GR2.4 | GR4.4 | GR7.4 | GR12.4 | GR13.4 | GR14.4 |

Another embodiment of the present invention are compounds of formula 1F wherein i=0 and $R^2$, $R^4$, $R^7$, $R^{12}$, $R^{13}$ and $R^{14}$, are defined as in table 6 above and pharmaceutically acceptable salts thereof.

Another embodiment of the present invention are compounds according to formula 1G,

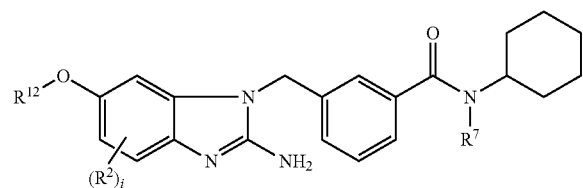

1G wherein
i, $R^2$, $R^7$, $R^{12}$, $R^{13}$ and $R^{14}$ have the meanings given hereinbefore and pharmaceutically acceptable salts thereof.

Another embodiment of the present invention are compounds of formula 1G wherein $R^2$, $R^7$, $R^{12}$, $R^{13}$ and $R^{14}$, are defined as in table 7 below and pharmaceutically acceptable salts thereof.

TABLE 7

| Group No. | R² | R⁷ | R¹² | R¹³ | R¹⁴ |
|---|---|---|---|---|---|
| 1. g | GR2.3 | GR6/7.3 | GR12.3 | GR13.3 | GR14.3 |
| 2. g | GR2.3 | GR6/7.3 | GR12.4 | GR13.3 | GR14.3 |
| 3. g | GR2.3 | GR7.4 | GR12.3 | GR13.3 | GR14.3 |
| 4. g | GR2.3 | GR7.4 | GR12.4 | GR13.3 | GR14.3 |
| 5. g | GR2.3 | GR6/7.3 | GR12.3 | GR13.3 | GR14.3 |
| 6. g | GR2.3 | GR6/7.3 | GR12.4 | GR13.3 | GR14.3 |
| 7. g | GR2.3 | GR7.4 | GR12.3 | GR13.3 | GR14.3 |
| 8. g | GR2.3 | GR7.4 | GR12.4 | GR13.3 | GR14.3 |
| 9. g | GR2.4 | GR6/7.3 | GR12.3 | GR13.3 | GR14.3 |
| 10. g | GR2.4 | GR6/7.3 | GR12.4 | GR13.3 | GR14.3 |
| 11. g | GR2.4 | GR7.4 | GR12.3 | GR13.3 | GR14.3 |
| 12. g | GR2.4 | GR7.4 | GR12.4 | GR13.3 | GR14.3 |
| 13. g | GR2.4 | GR6/7.3 | GR12.3 | GR13.3 | GR14.3 |
| 14. g | GR2.4 | GR6/7.3 | GR12.4 | GR13.3 | GR14.3 |
| 15. g | GR2.4 | GR7.4 | GR12.3 | GR13.3 | GR14.3 |
| 16. g | GR2.4 | GR7.4 | GR12.4 | GR13.3 | GR14.3 |
| 17. g | GR2.3 | GR6/7.3 | GR12.3 | GR13.4 | GR14.3 |
| 18. g | GR2.3 | GR6/7.3 | GR12.4 | GR13.4 | GR14.3 |
| 19. g | GR2.3 | GR7.4 | GR12.3 | GR13.4 | GR14.3 |
| 20. g | GR2.3 | GR7.4 | GR12.4 | GR13.4 | GR14.3 |
| 21. g | GR2.3 | GR6/7.3 | GR12.3 | GR13.4 | GR14.3 |
| 22. g | GR2.3 | GR6/7.3 | GR12.4 | GR13.4 | GR14.3 |
| 23. g | GR2.3 | GR7.4 | GR12.3 | GR13.4 | GR14.3 |
| 24. g | GR2.3 | GR7.4 | GR12.4 | GR13.4 | GR14.3 |
| 25. g | GR2.4 | GR6/7.3 | GR12.3 | GR13.4 | GR14.3 |
| 26. g | GR2.4 | GR6/7.3 | GR12.4 | GR13.4 | GR14.3 |
| 27. g | GR2.4 | GR7.4 | GR12.3 | GR13.4 | GR14.3 |
| 28. g | GR2.4 | GR7.4 | GR12.4 | GR13.4 | GR14.3 |
| 29. g | GR2.4 | GR6/7.3 | GR12.3 | GR13.4 | GR14.3 |
| 30. g | GR2.4 | GR6/7.3 | GR12.4 | GR13.4 | GR14.3 |
| 31. g | GR2.4 | GR7.4 | GR12.3 | GR13.4 | GR14.3 |
| 32. g | GR2.4 | GR7.4 | GR12.4 | GR13.4 | GR14.3 |
| 33. g | GR2.3 | GR6/7.3 | GR12.3 | GR13.3 | GR14.4 |
| 34. g | GR2.3 | GR6/7.3 | GR12.4 | GR13.3 | GR14.4 |
| 35. g | GR2.3 | GR7.4 | GR12.3 | GR13.3 | GR14.4 |
| 36. g | GR2.3 | GR7.4 | GR12.4 | GR13.3 | GR14.4 |
| 37. g | GR2.3 | GR6/7.3 | GR12.3 | GR13.3 | GR14.4 |
| 38. g | GR2.3 | GR6/7.3 | GR12.4 | GR13.3 | GR14.4 |
| 39. g | GR2.3 | GR7.4 | GR12.3 | GR13.3 | GR14.4 |
| 40. g | GR2.3 | GR7.4 | GR12.4 | GR13.3 | GR14.4 |
| 41. g | GR2.4 | GR6/7.3 | GR12.3 | GR13.3 | GR14.4 |
| 42. g | GR2.4 | GR6/7.3 | GR12.4 | GR13.3 | GR14.4 |
| 43. g | GR2.4 | GR7.4 | GR12.3 | GR13.3 | GR14.4 |
| 44. g | GR2.4 | GR7.4 | GR12.4 | GR13.3 | GR14.4 |
| 45. g | GR2.4 | GR6/7.3 | GR12.3 | GR13.3 | GR14.4 |
| 46. g | GR2.4 | GR6/7.3 | GR12.4 | GR13.3 | GR14.4 |
| 47. g | GR2.4 | GR7.4 | GR12.3 | GR13.3 | GR14.4 |
| 48. g | GR2.4 | GR7.4 | GR12.4 | GR13.3 | GR14.4 |
| 49. g | GR2.3 | GR6/7.3 | GR12.3 | GR13.4 | GR14.4 |
| 50. g | GR2.3 | GR6/7.3 | GR12.4 | GR13.4 | GR14.4 |
| 51. g | GR2.3 | GR7.4 | GR12.3 | GR13.4 | GR14.4 |
| 52. g | GR2.3 | GR7.4 | GR12.4 | GR13.4 | GR14.4 |
| 53. g | GR2.3 | GR6/7.3 | GR12.3 | GR13.4 | GR14.4 |
| 54. g | GR2.3 | GR6/7.3 | GR12.4 | GR13.4 | GR14.4 |
| 55. g | GR2.3 | GR7.4 | GR12.3 | GR13.4 | GR14.4 |
| 56. g | GR2.3 | GR7.4 | GR12.4 | GR13.4 | GR14.4 |
| 57. g | GR2.4 | GR6/7.3 | GR12.3 | GR13.4 | GR14.4 |
| 58. g | GR2.4 | GR6/7.3 | GR12.4 | GR13.4 | GR14.4 |
| 59. g | GR2.4 | GR7.4 | GR12.3 | GR13.4 | GR14.4 |
| 60. g | GR2.4 | GR7.4 | GR12.4 | GR13.4 | GR14.4 |
| 61. g | GR2.4 | GR6/7.3 | GR12.3 | GR13.4 | GR14.4 |
| 62. g | GR2.4 | GR6/7.3 | GR12.4 | GR13.4 | GR14.4 |
| 63. g | GR2.4 | GR7.4 | GR12.3 | GR13.4 | GR14.4 |
| 64. g | GR2.4 | GR7.4 | GR12.4 | GR13.4 | GR14.4 |

Another embodiment of the present invention are compounds of formula 1G wherein i=0 and $R^2$, $R^7$, $R^{12}$, $R^{13}$ and $R^{14}$, are defined as in table 7 above and pharmaceutically acceptable salts thereof.

Another embodiment of the present invention are compounds according to formula 1H,

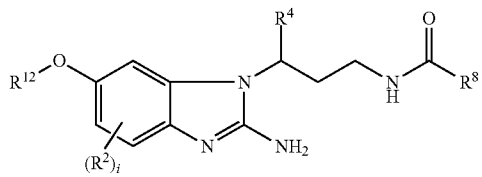

wherein
i, $R^2$, $R^4$, $R^8$, $R^{12}$, $R^{13}$ and $R^{14}$ have the meanings given hereinbefore and pharmaceutically acceptable salts thereof.

Another embodiment of the present invention are compounds of formula 1H wherein $R^2$, $R^4$, $R^8$, $R^{12}$, $R^{13}$ and $R^{14}$, are defined as in table 8 below and pharmaceutically acceptable salts thereof.

TABLE 8

| Group No. | $R^2$ | $R^4$ | $R^8$ | $R^{12}$ | $R^{13}$ | $R^{14}$ |
|---|---|---|---|---|---|---|
| 1. h | GR2.3 | GR4.3 | GR8.3 | GR12.3 | GR13.3 | GR14.3 |
| 2. h | GR2.3 | GR4.3 | GR8.3 | GR12.4 | GR13.3 | GR14.3 |
| 3. h | GR2.3 | GR4.3 | GR8.4 | GR12.3 | GR13.3 | GR14.3 |
| 4. h | GR2.3 | GR4.3 | GR8.4 | GR12.4 | GR13.3 | GR14.3 |
| 5. h | GR2.3 | GR4.4 | GR8.3 | GR12.3 | GR13.3 | GR14.3 |
| 6. h | GR2.3 | GR4.4 | GR8.3 | GR12.4 | GR13.3 | GR14.3 |
| 7. h | GR2.3 | GR4.4 | GR8.4 | GR12.3 | GR13.3 | GR14.3 |
| 8. h | GR2.3 | GR4.4 | GR8.4 | GR12.4 | GR13.3 | GR14.3 |
| 9. h | GR2.4 | GR4.3 | GR8.3 | GR12.3 | GR13.3 | GR14.3 |
| 10. h | GR2.4 | GR4.3 | GR8.3 | GR12.4 | GR13.3 | GR14.3 |
| 11. h | GR2.4 | GR4.3 | GR8.4 | GR12.3 | GR13.3 | GR14.3 |
| 12. h | GR2.4 | GR4.3 | GR8.4 | GR12.4 | GR13.3 | GR14.3 |
| 13. h | GR2.4 | GR4.4 | GR8.3 | GR12.3 | GR13.3 | GR14.3 |
| 14. h | GR2.4 | GR4.4 | GR8.3 | GR12.4 | GR13.3 | GR14.3 |
| 15. h | GR2.4 | GR4.4 | GR8.4 | GR12.3 | GR13.3 | GR14.3 |
| 16. h | GR2.4 | GR4.4 | GR8.4 | GR12.4 | GR13.3 | GR14.3 |
| 17. h | GR2.3 | GR4.3 | GR8.3 | GR12.3 | GR13.4 | GR14.3 |
| 18. h | GR2.3 | GR4.3 | GR8.3 | GR12.4 | GR13.4 | GR14.3 |
| 19. h | GR2.3 | GR4.3 | GR8.4 | GR12.3 | GR13.4 | GR14.3 |
| 20. h | GR2.3 | GR4.3 | GR8.4 | GR12.4 | GR13.4 | GR14.3 |
| 21. h | GR2.3 | GR4.4 | GR8.3 | GR12.3 | GR13.4 | GR14.3 |
| 22. h | GR2.3 | GR4.4 | GR8.3 | GR12.4 | GR13.4 | GR14.3 |
| 23. h | GR2.3 | GR4.4 | GR8.4 | GR12.3 | GR13.4 | GR14.3 |
| 24. h | GR2.3 | GR4.4 | GR8.4 | GR12.4 | GR13.4 | GR14.3 |
| 25. h | GR2.4 | GR4.3 | GR8.3 | GR12.3 | GR13.4 | GR14.3 |
| 26. h | GR2.4 | GR4.3 | GR8.3 | GR12.4 | GR13.4 | GR14.3 |
| 27. h | GR2.4 | GR4.3 | GR8.4 | GR12.3 | GR13.4 | GR14.3 |
| 28. h | GR2.4 | GR4.3 | GR8.4 | GR12.4 | GR13.4 | GR14.3 |
| 29. h | GR2.4 | GR4.4 | GR8.3 | GR12.3 | GR13.4 | GR14.3 |
| 30. h | GR2.4 | GR4.4 | GR8.3 | GR12.4 | GR13.4 | GR14.3 |
| 31. h | GR2.4 | GR4.4 | GR8.4 | GR12.3 | GR13.4 | GR14.3 |
| 32. h | GR2.4 | GR4.4 | GR8.4 | GR12.4 | GR13.4 | GR14.3 |
| 33. h | GR2.3 | GR4.3 | GR8.3 | GR12.3 | GR13.3 | GR14.4 |
| 34. h | GR2.3 | GR4.3 | GR8.3 | GR12.4 | GR13.3 | GR14.4 |
| 35. h | GR2.3 | GR4.3 | GR8.4 | GR12.3 | GR13.3 | GR14.4 |
| 36. h | GR2.3 | GR4.3 | GR8.4 | GR12.4 | GR13.3 | GR14.4 |
| 37. h | GR2.3 | GR4.4 | GR8.3 | GR12.3 | GR13.3 | GR14.4 |
| 38. h | GR2.3 | GR4.4 | GR8.3 | GR12.4 | GR13.3 | GR14.4 |
| 39. h | GR2.3 | GR4.4 | GR8.4 | GR12.3 | GR13.3 | GR14.4 |
| 40. h | GR2.3 | GR4.4 | GR8.4 | GR12.4 | GR13.3 | GR14.4 |
| 41. h | GR2.4 | GR4.3 | GR8.3 | GR12.3 | GR13.3 | GR14.4 |
| 42. h | GR2.4 | GR4.3 | GR8.3 | GR12.4 | GR13.3 | GR14.4 |
| 43. h | GR2.4 | GR4.3 | GR8.4 | GR12.3 | GR13.3 | GR14.4 |
| 44. h | GR2.4 | GR4.3 | GR8.4 | GR12.4 | GR13.3 | GR14.4 |
| 45. h | GR2.4 | GR4.4 | GR8.3 | GR12.3 | GR13.3 | GR14.4 |
| 46. h | GR2.4 | GR4.4 | GR8.3 | GR12.4 | GR13.3 | GR14.4 |
| 47. h | GR2.4 | GR4.4 | GR8.4 | GR12.3 | GR13.3 | GR14.4 |
| 48. h | GR2.4 | GR4.4 | GR8.4 | GR12.4 | GR13.3 | GR14.4 |
| 49. h | GR2.3 | GR4.3 | GR8.3 | GR12.3 | GR13.4 | GR14.4 |
| 50. h | GR2.3 | GR4.3 | GR8.3 | GR12.4 | GR13.4 | GR14.4 |
| 51. h | GR2.3 | GR4.3 | GR8.4 | GR12.3 | GR13.4 | GR14.4 |
| 52. h | GR2.3 | GR4.3 | GR8.4 | GR12.4 | GR13.4 | GR14.4 |
| 53. h | GR2.3 | GR4.4 | GR8.3 | GR12.3 | GR13.4 | GR14.4 |
| 54. h | GR2.3 | GR4.4 | GR8.3 | GR12.4 | GR13.4 | GR14.4 |
| 55. h | GR2.3 | GR4.4 | GR8.4 | GR12.3 | GR13.4 | GR14.4 |
| 56. h | GR2.3 | GR4.4 | GR8.4 | GR12.4 | GR13.4 | GR14.4 |
| 57. h | GR2.4 | GR4.3 | GR8.3 | GR12.3 | GR13.4 | GR14.4 |
| 58. h | GR2.4 | GR4.3 | GR8.3 | GR12.4 | GR13.4 | GR14.4 |
| 59. h | GR2.4 | GR4.3 | GR8.4 | GR12.3 | GR13.4 | GR14.4 |
| 60. h | GR2.4 | GR4.3 | GR8.4 | GR12.4 | GR13.4 | GR14.4 |
| 61. h | GR2.4 | GR4.4 | GR8.3 | GR12.3 | GR13.4 | GR14.4 |
| 62. h | GR2.4 | GR4.4 | GR8.3 | GR12.4 | GR13.4 | GR14.4 |
| 63. h | GR2.4 | GR4.4 | GR8.4 | GR12.3 | GR13.4 | GR14.4 |
| 64. h | GR2.4 | GR4.4 | GR8.4 | GR12.4 | GR13.4 | GR14.4 |

Another embodiment of the present invention are compounds of formula 1H wherein i=0 and $R^2$, $R^4$, $R^8$, $R^{12}$, $R^{13}$ and $R^{14}$, are defined as in table 8 above and pharmaceutically acceptable salts thereof.

Another embodiment of the present invention are compounds according to formula 1I,

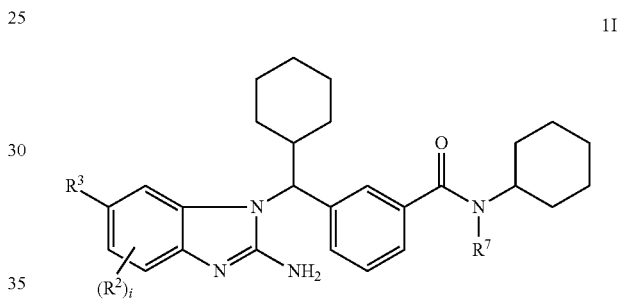

wherein
$R^2$, $R^3$, $R^7$, $R^{12}$, $R^{13}$ and $R^{14}$ have the meanings given hereinbefore and pharmaceutically acceptable salts thereof.

Another embodiment of the present invention are such compounds of formula 1I wherein $R^2$, $R^3$, $R^7$, $R^{12}$, $R^{13}$ and $R^{14}$, are defined as in table 3 below and pharmaceutically acceptable salts thereof.

TABLE 9

| Group No. | $R^2$ | $R^3$ | $R^{7b}$ | $R^{12}$ | $R^{13}$ | $R^{14}$ |
|---|---|---|---|---|---|---|
| 1. i | GR2.3 | GR3.3 | GR6/7.3 | GR12.3 | GR13.3 | GR14.3 |
| 2. i | GR2.3 | GR3.3 | GR6/7.3 | GR12.4 | GR13.3 | GR14.3 |
| 3. i | GR2.3 | GR3.3 | GR7.4 | GR12.3 | GR13.3 | GR14.3 |
| 4. i | GR2.3 | GR3.3 | GR7.4 | GR12.4 | GR13.3 | GR14.3 |
| 5. i | GR2.3 | GR3.4 | GR6/7.3 | GR12.3 | GR13.3 | GR14.3 |
| 6. i | GR2.3 | GR3.4 | GR6/7.3 | GR12.4 | GR13.3 | GR14.3 |
| 7. i | GR2.3 | GR3.4 | GR7.4 | GR12.3 | GR13.3 | GR14.3 |
| 8. i | GR2.3 | GR3.4 | GR7.4 | GR12.4 | GR13.3 | GR14.3 |
| 9. i | GR2.4 | GR3.3 | GR6/7.3 | GR12.3 | GR13.3 | GR14.3 |
| 10. i | GR2.4 | GR3.3 | GR6/7.3 | GR12.4 | GR13.3 | GR14.3 |
| 11. i | GR2.4 | GR3.3 | GR7.4 | GR12.3 | GR13.3 | GR14.3 |
| 12. i | GR2.4 | GR3.3 | GR7.4 | GR12.4 | GR13.3 | GR14.3 |
| 13. i | GR2.4 | GR3.4 | GR6/7.3 | GR12.3 | GR13.3 | GR14.3 |
| 14. i | GR2.4 | GR3.4 | GR6/7.3 | GR12.4 | GR13.3 | GR14.3 |
| 15. i | GR2.4 | GR3.4 | GR7.4 | GR12.3 | GR13.3 | GR14.3 |
| 16. i | GR2.4 | GR3.4 | GR7.4 | GR12.4 | GR13.3 | GR14.3 |
| 17. i | GR2.3 | GR3.3 | GR6/7.3 | GR12.3 | GR13.4 | GR14.3 |
| 18. i | GR2.3 | GR3.3 | GR6/7.3 | GR12.4 | GR13.4 | GR14.3 |
| 19. i | GR2.3 | GR3.3 | GR7.4 | GR12.3 | GR13.4 | GR14.3 |
| 20. i | GR2.3 | GR3.3 | GR7.4 | GR12.4 | GR13.4 | GR14.3 |
| 21. i | GR2.3 | GR3.4 | GR6/7.3 | GR12.3 | GR13.4 | GR14.3 |

TABLE 9-continued

| Group No. | $R^2$ | $R^3$ | $R^{7b}$ | $R^{12}$ | $R^{13}$ | $R^{14}$ |
|---|---|---|---|---|---|---|
| 22. i | GR2.3 | GR3.4 | GR6/7.3 | GR12.4 | GR13.4 | GR14.3 |
| 23. i | GR2.3 | GR3.4 | GR7.4 | GR12.3 | GR13.4 | GR14.3 |
| 24. i | GR2.3 | GR3.4 | GR7.4 | GR12.4 | GR13.4 | GR14.3 |
| 25. i | GR2.4 | GR3.3 | GR6/7.3 | GR12.3 | GR13.4 | GR14.3 |
| 26. i | GR2.4 | GR3.3 | GR6/7.3 | GR12.4 | GR13.4 | GR14.3 |
| 27. i | GR2.4 | GR3.3 | GR7.4 | GR12.3 | GR13.4 | GR14.3 |
| 28. i | GR2.4 | GR3.3 | GR7.4 | GR12.4 | GR13.4 | GR14.3 |
| 29. i | GR2.4 | GR3.4 | GR6/7.3 | GR12.3 | GR13.4 | GR14.3 |
| 30. i | GR2.4 | GR3.4 | GR6/7.3 | GR12.4 | GR13.4 | GR14.3 |
| 31. i | GR2.4 | GR3.4 | GR7.4 | GR12.3 | GR13.4 | GR14.3 |
| 32. i | GR2.4 | GR3.4 | GR7.4 | GR12.4 | GR13.4 | GR14.3 |
| 33. i | GR2.3 | GR3.3 | GR6/7.3 | GR12.3 | GR13.3 | GR14.4 |
| 34. i | GR2.3 | GR3.3 | GR6/7.3 | GR12.4 | GR13.3 | GR14.4 |
| 35. i | GR2.3 | GR3.3 | GR7.4 | GR12.3 | GR13.3 | GR14.4 |
| 36. i | GR2.3 | GR3.3 | GR7.4 | GR12.4 | GR13.3 | GR14.4 |
| 37. i | GR2.3 | GR3.4 | GR6/7.3 | GR12.3 | GR13.3 | GR14.4 |
| 38. i | GR2.3 | GR3.4 | GR6/7.3 | GR12.4 | GR13.3 | GR14.4 |
| 39. i | GR2.3 | GR3.4 | GR7.4 | GR12.3 | GR13.3 | GR14.4 |
| 40. i | GR2.3 | GR3.4 | GR7.4 | GR12.4 | GR13.3 | GR14.4 |
| 41. i | GR2.4 | GR3.3 | GR6/7.3 | GR12.3 | GR13.3 | GR14.4 |
| 42. i | GR2.4 | GR3.3 | GR6/7.3 | GR12.4 | GR13.3 | GR14.4 |
| 43. i | GR2.4 | GR3.3 | GR7.4 | GR12.3 | GR13.3 | GR14.4 |
| 44. i | GR2.4 | GR3.3 | GR7.4 | GR12.4 | GR13.3 | GR14.4 |
| 45. i | GR2.4 | GR3.4 | GR6/7.3 | GR12.3 | GR13.3 | GR14.4 |
| 46. i | GR2.4 | GR3.4 | GR6/7.3 | GR12.4 | GR13.3 | GR14.4 |
| 47. i | GR2.4 | GR3.4 | GR7.4 | GR12.3 | GR13.3 | GR14.4 |
| 48. i | GR2.4 | GR3.4 | GR7.4 | GR12.4 | GR13.3 | GR14.4 |
| 49. i | GR2.3 | GR3.3 | GR6/7.3 | GR12.3 | GR13.4 | GR14.4 |
| 50. i | GR2.3 | GR3.3 | GR6/7.3 | GR12.4 | GR13.4 | GR14.4 |
| 51. i | GR2.3 | GR3.3 | GR7.4 | GR12.3 | GR13.4 | GR14.4 |
| 52. i | GR2.3 | GR3.3 | GR7.4 | GR12.4 | GR13.4 | GR14.4 |
| 53. i | GR2.3 | GR3.4 | GR6/7.3 | GR12.3 | GR13.4 | GR14.4 |
| 54. i | GR2.3 | GR3.4 | GR6/7.3 | GR12.4 | GR13.4 | GR14.4 |
| 55. i | GR2.3 | GR3.4 | GR7.4 | GR12.3 | GR13.4 | GR14.4 |
| 56. i | GR2.3 | GR3.4 | GR7.4 | GR12.4 | GR13.4 | GR14.4 |
| 57. i | GR2.4 | GR3.3 | GR6/7.3 | GR12.3 | GR13.4 | GR14.4 |
| 58. i | GR2.4 | GR3.3 | GR6/7.3 | GR12.4 | GR13.4 | GR14.4 |
| 59. i | GR2.4 | GR3.3 | GR7.4 | GR12.3 | GR13.4 | GR14.4 |
| 60. i | GR2.4 | GR3.3 | GR7.4 | GR12.4 | GR13.4 | GR14.4 |
| 61. i | GR2.4 | GR3.4 | GR6/7.3 | GR12.3 | GR13.4 | GR14.4 |
| 62. i | GR2.4 | GR3.4 | GR6/7.3 | GR12.4 | GR13.4 | GR14.4 |
| 63. i | GR2.4 | GR3.4 | GR7.4 | GR12.3 | GR13.4 | GR14.4 |
| 64. i | GR2.4 | GR3.4 | GR7.4 | GR12.4 | GR13.4 | GR14.4 |

Another embodiment of the present invention are such compounds of formula 1I wherein i=0 and $R^2$, $R^3$, $R^7$, $R^{12}$, $R^{13}$ and $R^{14}$, are defined as in table 9 above and pharmaceutically acceptable salts thereof.

Another embodiment of the present invention are compounds according to formula 1J,

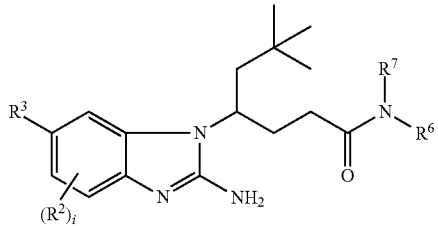

1J wherein
i, $R^2$, $R^3$, $R^6$, $R^7$, $R^{12}$, $R^{13}$ and $R^{14}$ have the meanings given hereinbefore and pharmaceutically acceptable salts thereof.

Another embodiment of the present invention are compounds of formula 1J wherein $R^2$, $R^3$, $R^6$, $R^7$, $R^{12}$, $R^{13}$ and $R^{14}$, are defined as in table 10 below and pharmaceutically acceptable salts thereof.

TABLE 10

| Group No. | $R^2$ | $R^3$ | $R^6$ | $R^7$ | $R^{12}$ | $R^{13}$ | $R^{14}$ |
|---|---|---|---|---|---|---|---|
| 1. j | GR2.3 | GR3.3 | GR6/7.3 | GR6/7.3 | GR12.3 | GR13.3 | GR14.3 |
| 2. j | GR2.3 | GR3.3 | GR6/7.3 | GR6/7.3 | GR12.4 | GR13.3 | GR14.3 |
| 3. j | GR2.3 | GR3.3 | GR6/7.3 | GR7.4 | GR12.3 | GR13.3 | GR14.3 |
| 4. j | GR2.3 | GR3.3 | GR6/7.3 | GR7.4 | GR12.4 | GR13.3 | GR14.3 |
| 5. j | GR2.3 | GR3.3 | GR6.4 | GR6/7.3 | GR12.3 | GR13.3 | GR14.3 |
| 6. j | GR2.3 | GR3.3 | GR6.4 | GR6/7.3 | GR12.4 | GR13.3 | GR14.3 |
| 7. j | GR2.3 | GR3.3 | GR6.4 | GR7.4 | GR12.3 | GR13.3 | GR14.3 |
| 8. j | GR2.3 | GR3.3 | GR6.4 | GR7.4 | GR12.4 | GR13.3 | GR14.3 |
| 9. j | GR2.3 | GR3.4 | GR6/7.3 | GR6/7.3 | GR12.3 | GR13.3 | GR14.3 |
| 10. j | GR2.3 | GR3.4 | GR6/7.3 | GR6/7.3 | GR12.4 | GR13.3 | GR14.3 |
| 11. j | GR2.3 | GR3.4 | GR6/7.3 | GR7.4 | GR12.3 | GR13.3 | GR14.3 |
| 12. j | GR2.3 | GR3.4 | GR6/7.3 | GR7.4 | GR12.4 | GR13.3 | GR14.3 |
| 13. j | GR2.3 | GR3.4 | GR6.4 | GR6/7.3 | GR12.3 | GR13.3 | GR14.3 |
| 14. j | GR2.3 | GR3.4 | GR6.4 | GR6/7.3 | GR12.4 | GR13.3 | GR14.3 |
| 15. j | GR2.3 | GR3.4 | GR6.4 | GR7.4 | GR12.3 | GR13.3 | GR14.3 |
| 16. j | GR2.3 | GR3.4 | GR6.4 | GR7.4 | GR12.4 | GR13.3 | GR14.3 |
| 17. j | GR2.4 | GR3.3 | GR6/7.3 | GR6/7.3 | GR12.3 | GR13.3 | GR14.3 |
| 18. j | GR2.4 | GR3.3 | GR6/7.3 | GR6/7.3 | GR12.4 | GR13.3 | GR14.3 |
| 19. j | GR2.4 | GR3.3 | GR6/7.3 | GR7.4 | GR12.3 | GR13.3 | GR14.3 |
| 20. j | GR2.4 | GR3.3 | GR6/7.3 | GR7.4 | GR12.4 | GR13.3 | GR14.3 |
| 21. j | GR2.4 | GR3.3 | GR6.4 | GR6/7.3 | GR12.3 | GR13.3 | GR14.3 |
| 22. j | GR2.4 | GR3.3 | GR6.4 | GR6/7.3 | GR12.4 | GR13.3 | GR14.3 |
| 23. j | GR2.4 | GR3.3 | GR6.4 | GR7.4 | GR12.3 | GR13.3 | GR14.3 |
| 24. j | GR2.4 | GR3.3 | GR6.4 | GR7.4 | GR12.4 | GR13.3 | GR14.3 |
| 25. j | GR2.4 | GR3.4 | GR6/7.3 | GR6/7.3 | GR12.3 | GR13.3 | GR14.3 |
| 26. j | GR2.4 | GR3.4 | GR6/7.3 | GR6/7.3 | GR12.4 | GR13.3 | GR14.3 |
| 27. j | GR2.4 | GR3.4 | GR6/7.3 | GR7.4 | GR12.3 | GR13.3 | GR14.3 |
| 28. j | GR2.4 | GR3.4 | GR6/7.3 | GR7.4 | GR12.4 | GR13.3 | GR14.3 |
| 29. j | GR2.4 | GR3.4 | GR6.4 | GR6/7.3 | GR12.3 | GR13.3 | GR14.3 |
| 30. j | GR2.4 | GR3.4 | GR6.4 | GR6/7.3 | GR12.4 | GR13.3 | GR14.3 |
| 31. j | GR2.4 | GR3.4 | GR6.4 | GR7.4 | GR12.3 | GR13.3 | GR14.3 |

TABLE 10-continued

| Group No. | R² | R³ | R⁶ | R⁷ | R¹² | R¹³ | R¹⁴ |
|---|---|---|---|---|---|---|---|
| 32.j | GR2.4 | GR3.4 | GR6.4 | GR7.4 | GR12.4 | GR13.3 | GR14.3 |
| 33.j | GR2.3 | GR3.3 | GR6/7.3 | GR6/7.3 | GR12.3 | GR13.4 | GR14.3 |
| 34.j | GR2.3 | GR3.3 | GR6/7.3 | GR6/7.3 | GR12.4 | GR13.4 | GR14.3 |
| 35.j | GR2.3 | GR3.3 | GR6/7.3 | GR7.4 | GR12.3 | GR13.4 | GR14.3 |
| 36.j | GR2.3 | GR3.3 | GR6/7.3 | GR7.4 | GR12.4 | GR13.4 | GR14.3 |
| 37.j | GR2.3 | GR3.3 | GR6.4 | GR6/7.3 | GR12.3 | GR13.4 | GR14.3 |
| 38.j | GR2.3 | GR3.3 | GR6.4 | GR6/7.3 | GR12.4 | GR13.4 | GR14.3 |
| 39.j | GR2.3 | GR3.3 | GR6.4 | GR7.4 | GR12.3 | GR13.4 | GR14.3 |
| 40.j | GR2.3 | GR3.3 | GR6.4 | GR7.4 | GR12.4 | GR13.4 | GR14.3 |
| 41.j | GR2.3 | GR3.4 | GR6/7.3 | GR6/7.3 | GR12.3 | GR13.4 | GR14.3 |
| 42.j | GR2.3 | GR3.4 | GR6/7.3 | GR6/7.3 | GR12.4 | GR13.4 | GR14.3 |
| 43.j | GR2.3 | GR3.4 | GR6/7.3 | GR7.4 | GR12.3 | GR13.4 | GR14.3 |
| 44.j | GR2.3 | GR3.4 | GR6/7.3 | GR7.4 | GR12.4 | GR13.4 | GR14.3 |
| 45.j | GR2.3 | GR3.4 | GR6.4 | GR6/7.3 | GR12.3 | GR13.4 | GR14.3 |
| 46.j | GR2.3 | GR3.4 | GR6.4 | GR6/7.3 | GR12.4 | GR13.4 | GR14.3 |
| 47.j | GR2.3 | GR3.4 | GR6.4 | GR7.4 | GR12.3 | GR13.4 | GR14.3 |
| 48.j | GR2.3 | GR3.4 | GR6.4 | GR7.4 | GR12.4 | GR13.4 | GR14.3 |
| 49.j | GR2.4 | GR3.3 | GR6/7.3 | GR6/7.3 | GR12.3 | GR13.4 | GR14.3 |
| 50.j | GR2.4 | GR3.3 | GR6/7.3 | GR6/7.3 | GR12.4 | GR13.4 | GR14.3 |
| 51.j | GR2.4 | GR3.3 | GR6/7.3 | GR7.4 | GR12.3 | GR13.4 | GR14.3 |
| 52.j | GR2.4 | GR3.3 | GR6/7.3 | GR7.4 | GR12.4 | GR13.4 | GR14.3 |
| 53.j | GR2.4 | GR3.3 | GR6.4 | GR6/7.3 | GR12.3 | GR13.4 | GR14.3 |
| 54.j | GR2.4 | GR3.3 | GR6.4 | GR6/7.3 | GR12.4 | GR13.4 | GR14.3 |
| 55.j | GR2.4 | GR3.3 | GR6.4 | GR7.4 | GR12.3 | GR13.4 | GR14.3 |
| 56.j | GR2.4 | GR3.3 | GR6.4 | GR7.4 | GR12.4 | GR13.4 | GR14.3 |
| 57.j | GR2.4 | GR3.4 | GR6/7.3 | GR6/7.3 | GR12.3 | GR13.4 | GR14.3 |
| 58.j | GR2.4 | GR3.4 | GR6/7.3 | GR6/7.3 | GR12.4 | GR13.4 | GR14.3 |
| 59.j | GR2.4 | GR3.4 | GR6/7.3 | GR7.4 | GR12.3 | GR13.4 | GR14.3 |
| 60.j | GR2.4 | GR3.4 | GR6/7.3 | GR7.4 | GR12.4 | GR13.4 | GR14.3 |
| 61.j | GR2.4 | GR3.4 | GR6.4 | GR6/7.3 | GR12.3 | GR13.4 | GR14.3 |
| 62.j | GR2.4 | GR3.4 | GR6.4 | GR6/7.3 | GR12.4 | GR13.4 | GR14.3 |
| 63.j | GR2.4 | GR3.4 | GR6.4 | GR7.4 | GR12.3 | GR13.4 | GR14.3 |
| 64.j | GR2.4 | GR3.4 | GR6.4 | GR7.4 | GR12.4 | GR13.4 | GR14.3 |
| 65.j | GR2.3 | GR3.3 | GR6/7.3 | GR6/7.3 | GR12.3 | GR13.3 | GR14.4 |
| 66.j | GR2.3 | GR3.3 | GR6/7.3 | GR6/7.3 | GR12.4 | GR13.3 | GR14.4 |
| 67.j | GR2.3 | GR3.3 | GR6/7.3 | GR7.4 | GR12.3 | GR13.3 | GR14.4 |
| 68.j | GR2.3 | GR3.3 | GR6/7.3 | GR7.4 | GR12.4 | GR13.3 | GR14.4 |
| 69.j | GR2.3 | GR3.3 | GR6.4 | GR6/7.3 | GR12.3 | GR13.3 | GR14.4 |
| 70.j | GR2.3 | GR3.3 | GR6.4 | GR6/7.3 | GR12.4 | GR13.3 | GR14.4 |
| 71.j | GR2.3 | GR3.3 | GR6.4 | GR7.4 | GR12.3 | GR13.3 | GR14.4 |
| 72.j | GR2.3 | GR3.3 | GR6.4 | GR7.4 | GR12.4 | GR13.3 | GR14.4 |
| 73.j | GR2.3 | GR3.4 | GR6/7.3 | GR6/7.3 | GR12.3 | GR13.3 | GR14.4 |
| 74.j | GR2.3 | GR3.4 | GR6/7.3 | GR6/7.3 | GR12.4 | GR13.3 | GR14.4 |
| 75.j | GR2.3 | GR3.4 | GR6/7.3 | GR7.4 | GR12.3 | GR13.3 | GR14.4 |
| 76.j | GR2.3 | GR3.4 | GR6/7.3 | GR7.4 | GR12.4 | GR13.3 | GR14.4 |
| 77.j | GR2.3 | GR3.4 | GR6.4 | GR6/7.3 | GR12.3 | GR13.3 | GR14.4 |
| 78.j | GR2.3 | GR3.4 | GR6.4 | GR6/7.3 | GR12.4 | GR13.3 | GR14.4 |
| 79.j | GR2.3 | GR3.4 | GR6.4 | GR7.4 | GR12.3 | GR13.3 | GR14.4 |
| 80.j | GR2.3 | GR3.4 | GR6.4 | GR7.4 | GR12.4 | GR13.3 | GR14.4 |
| 81.j | GR2.4 | GR3.3 | GR6/7.3 | GR6/7.3 | GR12.3 | GR13.3 | GR14.4 |
| 82.j | GR2.4 | GR3.3 | GR6/7.3 | GR6/7.3 | GR12.4 | GR13.3 | GR14.4 |
| 83.j | GR2.4 | GR3.3 | GR6/7.3 | GR7.4 | GR12.3 | GR13.3 | GR14.4 |
| 84.j | GR2.4 | GR3.3 | GR6/7.3 | GR7.4 | GR12.4 | GR13.3 | GR14.4 |
| 85.j | GR2.4 | GR3.3 | GR6.4 | GR6/7.3 | GR12.3 | GR13.3 | GR14.4 |
| 86.j | GR2.4 | GR3.3 | GR6.4 | GR6/7.3 | GR12.4 | GR13.3 | GR14.4 |
| 87.j | GR2.4 | GR3.3 | GR6.4 | GR7.4 | GR12.3 | GR13.3 | GR14.4 |
| 88.j | GR2.4 | GR3.3 | GR6.4 | GR7.4 | GR12.4 | GR13.3 | GR14.4 |
| 89.j | GR2.4 | GR3.4 | GR6/7.3 | GR6/7.3 | GR12.3 | GR13.3 | GR14.4 |
| 90.j | GR2.4 | GR3.4 | GR6/7.3 | GR6/7.3 | GR12.4 | GR13.3 | GR14.4 |
| 91.j | GR2.4 | GR3.4 | GR6/7.3 | GR7.4 | GR12.3 | GR13.4 | GR14.4 |
| 92.j | GR2.4 | GR3.4 | GR6/7.3 | GR7.4 | GR12.4 | GR13.3 | GR14.4 |
| 93.j | GR2.4 | GR3.4 | GR6.4 | GR6/7.3 | GR12.3 | GR13.3 | GR14.4 |
| 94.j | GR2.4 | GR3.4 | GR6.4 | GR6/7.3 | GR12.4 | GR13.3 | GR14.4 |
| 95.j | GR2.4 | GR3.4 | GR6.4 | GR7.4 | GR12.3 | GR13.3 | GR14.4 |
| 96.j | GR2.4 | GR3.4 | GR6.4 | GR7.4 | GR12.4 | GR13.3 | GR14.4 |
| 97.j | GR2.3 | GR3.3 | GR6/7.3 | GR6/7.3 | GR12.3 | GR13.4 | GR14.4 |
| 98.j | GR2.3 | GR3.3 | GR6/7.3 | GR6/7.3 | GR12.4 | GR13.4 | GR14.4 |
| 99.j | GR2.3 | GR3.3 | GR6/7.3 | GR7.4 | GR12.3 | GR13.4 | GR14.4 |
| 100.j | GR2.3 | GR3.3 | GR6/7.3 | GR7.4 | GR12.4 | GR13.4 | GR14.4 |
| 101.j | GR2.3 | GR3.3 | GR6.4 | GR6/7.3 | GR12.3 | GR13.4 | GR14.4 |
| 102.j | GR2.3 | GR3.3 | GR6.4 | GR6/7.3 | GR12.4 | GR13.4 | GR14.4 |
| 103.j | GR2.3 | GR3.3 | GR6.4 | GR7.4 | GR12.3 | GR13.4 | GR14.4 |
| 104.j | GR2.3 | GR3.3 | GR6.4 | GR7.4 | GR12.4 | GR13.4 | GR14.4 |
| 105.j | GR2.3 | GR3.4 | GR6/7.3 | GR6/7.3 | GR12.3 | GR13.4 | GR14.4 |
| 106.j | GR2.3 | GR3.4 | GR6/7.3 | GR6/7.3 | GR12.4 | GR13.4 | GR14.4 |
| 107.j | GR2.3 | GR3.4 | GR6/7.3 | GR7.4 | GR12.3 | GR13.4 | GR14.4 |
| 108.j | GR2.3 | GR3.4 | GR6/7.3 | GR7.4 | GR12.4 | GR13.4 | GR14.4 |

TABLE 10-continued

| Group No. | R² | R³ | R⁶ | R⁷ | R¹² | R¹³ | R¹⁴ |
|---|---|---|---|---|---|---|---|
| 109. j | GR2.3 | GR3.4 | GR6.4 | GR6/7.3 | GR12.3 | GR13.4 | GR14.4 |
| 110. j | GR2.3 | GR3.4 | GR6.4 | GR6/7.3 | GR12.4 | GR13.4 | GR14.4 |
| 111. j | GR2.3 | GR3.4 | GR6.4 | GR7.4 | GR12.3 | GR13.4 | GR14.4 |
| 112. j | GR2.3 | GR3.4 | GR6.4 | GR7.4 | GR12.4 | GR13.4 | GR14.4 |
| 113. j | GR2.4 | GR3.3 | GR6/7.3 | GR6/7.3 | GR12.3 | GR13.4 | GR14.4 |
| 114. j | GR2.4 | GR3.3 | GR6/7.3 | GR6/7.3 | GR12.4 | GR13.4 | GR14.4 |
| 115. j | GR2.4 | GR3.3 | GR6/7.3 | GR7.4 | GR12.3 | GR13.4 | GR14.4 |
| 116. j | GR2.4 | GR3.3 | GR6/7.3 | GR7.4 | GR12.4 | GR13.4 | GR14.4 |
| 117. j | GR2.4 | GR3.3 | GR6.4 | GR6/7.3 | GR12.3 | GR13.4 | GR14.4 |
| 118. j | GR2.4 | GR3.3 | GR6.4 | GR6/7.3 | GR12.4 | GR13.4 | GR14.4 |
| 119. j | GR2.4 | GR3.3 | GR6.4 | GR7.4 | GR12.3 | GR13.4 | GR14.4 |
| 120. j | GR2.4 | GR3.3 | GR6.4 | GR7.4 | GR12.4 | GR13.4 | GR14.4 |
| 121. j | GR2.4 | GR3.4 | GR6/7.3 | GR6/7.3 | GR12.3 | GR13.4 | GR14.4 |
| 122. j | GR2.4 | GR3.4 | GR6/7.3 | GR6/7.3 | GR12.4 | GR13.4 | GR14.4 |
| 123. j | GR2.4 | GR3.4 | GR6/7.3 | GR7.4 | GR12.3 | GR13.4 | GR14.4 |
| 124. j | GR2.4 | GR3.4 | GR6/7.3 | GR7.4 | GR12.4 | GR13.4 | GR14.4 |
| 125. j | GR2.4 | GR3.4 | GR6.4 | GR6/7.3 | GR12.3 | GR13.4 | GR14.4 |
| 126. j | GR2.4 | GR3.4 | GR6.4 | GR6/7.3 | GR12.4 | GR13.4 | GR14.4 |
| 127. j | GR2.4 | GR3.4 | GR6.4 | GR7.4 | GR12.3 | GR13.4 | GR14.4 |
| 128. j | GR2.4 | GR3.4 | GR6.4 | GR7.4 | GR12.4 | GR13.4 | GR14.4 |

Another embodiment of the present invention are compounds of formula 1J wherein i=0 and $R^2$, $R^3$, $R^6$, $R^7$, $R^{12}$, $R^{13}$ and $R^{14}$, are defined as in table 10 above and pharmaceutically acceptable salts thereof.

Another embodiment of the present invention are compounds according to the following table:

TABLE 9

| No. | Compound | See Example No. |
|---|---|---|
| (1) | | 13 |
| (2) | | 30 |
| (3) | | 42 |

TABLE 9-continued

| No. | Compound | See Example No. |
|---|---|---|
| (4) | | 1 |
| (5) | | 33 |
| (6) | | 43 |
| (7) | | 25 |
| (8) | | 34 |
| (9) | | 7 |

TABLE 9-continued

| No. | Compound | See Example No. |
|---|---|---|
| (10) | | 19 |
| (11) | | 8 |
| (12) | | 44 |
| (13) | | 26 |
| (14) | | 52 |
| (15) | | 31 |
| (16) | | 9 |

TABLE 9-continued
| No. | Compound | See Example No. |
|---|---|---|
| (17) | 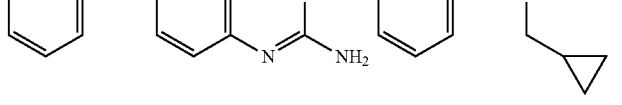 | 29 |
| (18) | 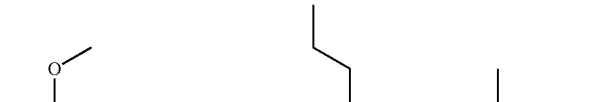 | 2 |
| (19) | 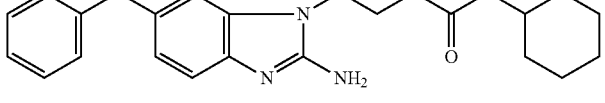 | 10 |
| (20) |  | 5 |
| (21) | 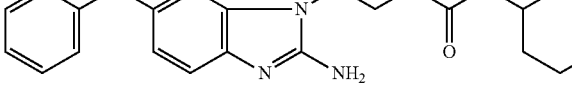 | 11 |
| (22) | 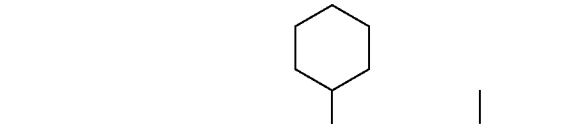 | 53 |
| (23) | 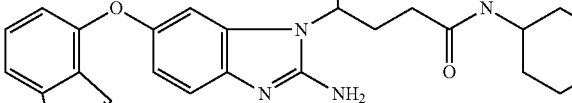 | 12 |

TABLE 9-continued
| No. | Compound | See Example No. |
|---|---|---|
| (24) | 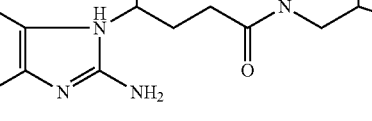 | 22 |
| (25) | 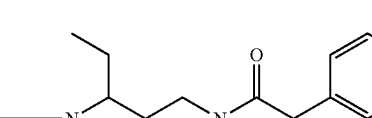 | 51 |
| (26) | 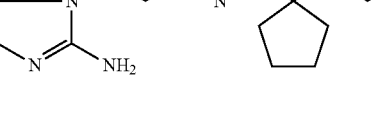 | 21 |
| (27) | 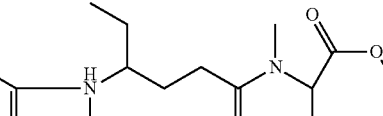 | 50 |
| (28) | 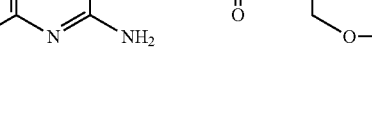 | 15 |
| (29) | 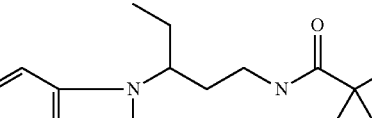 | 28 |
| (30) | 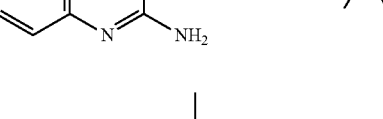 | 27 |

TABLE 9-continued

| No. | Compound | See Example No. |
|---|---|---|
| (31) | (structure) | 55 |
| (32) | (structure) | 54 |
| (33) | (structure) | 18 |
| (34) | (structure) | 37 |
| (35) | (structure) | 45 |
| (36) | (structure) | 36 |
| (37) | (structure) | 38 |
| (38) | (structure) | 46 |

TABLE 9-continued

| No. | Compound | See Example No. |
|---|---|---|
| (39) | | 6 |
| (40) | | 20 |
| (41) | | 16 |
| (42) | | 41 |
| (43) | | 39 |
| (44) | | 35 |
| (45) | | 23 |

TABLE 9-continued

| No. | Compound | See Example No. |
|---|---|---|
| (46) | | 49 |
| (47) | | 42 |
| (48) | | 48 |
| (49) | | 3 |
| (50) | | 17 |
| (51) | | 14 |
| (52) | | 4 |

TABLE 9-continued

| No. | Compound | See Example No. |
|---|---|---|
| (53) | | 24 |
| (54) | | 40 |
| (55) | | 47 |

The compounds herein described may have asymmetric centres. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, —$C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

In general, all tautomeric forms and isomeric forms and mixtures, whether individual geometric isomers or optical isomers or racemic or non-racemic mixtures of isomers, of a chemical structure or compound is intended, unless the specific stereochemistry or isomeric form is specifically indicated in the compound name or structure.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like. (also see Pharmaceutical salts, Birge, S. M. et al., J. Pharm. Sci., (1977), 66, 1-19). As the compounds of the present invention may have both, acid as well as basic groups, those compounds may therefore be present as internal salts too.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remingto which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

The term halogen denotes an atom selected from among F, Cl, Br and I.

The term $C_{1-n}$-alkyl, wherein n may have a value from 1 to 10, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl etc.

The term $C_{2-n}$-alkenyl, wherein n has a value of 3 to 6, denotes a branched or unbranched hydrocarbon group with 2 to n C atoms and a C=C double bond. Examples of such groups include ethenyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc.

The term $C_{1-n}$-alkoxy or $C_{1-n}$-alkyloxy denotes a $C_{1-n}$-alkyl-O group, wherein $C_{1-n}$-alkyl is defined as above. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{3-n}$-cycloalkyl denotes a saturated monocyclic group with 3 to n C atoms. Examples of such groups include cyclopropyl, cyclobutyl, cyclopentyl, cyclohexyl, cycloheptyl etc.

The term $C_{3-n}$-polycycloalkyl denotes saturated or unsaturated bridged polycyclic bi-, tri-, tetra-, penta- or hexacycloalcanes with 6 to n C atoms. Examples of such groups include bicyclo[2.2.0]hexa-2,5-dienyl, tricyclo[3.1.0.0$^{2,6}$] hex-3-enyl, tricyclo[1.1.0.0$^{2,4}$]butanyl, tricyclo[3.3.1.1$^{3,7}$] decanyl, tetracyclo[2.2.0.0$^{2,6}$.0$^{3,5}$]hexanyl, pentacyclo [4.2.0.0$^{2,5}$.0$^{3,8}$.0$^{4,7}$]octanyl, 2,6,6-trimethylbicyclo[3.1.1] heptanyl etc.

The term $C_{3-n}$-cycloalkyloxy denotes a $C_{3-n}$-cycloalkyl-O group wherein $C_{3-n}$-cycloalkyl is defined as above. Examples of such groups include cyclopropyloxy, cyclobutyloxy, cyclopentyloxy, cyclohexyloxy, cycloheptyloxy etc.

The term $C_{3-n}$-cycloalkyl-$C_{1-n}$-alkoxy denotes a $C_{3-n}$-cycloalkyl group wherein $C_{3-n}$-cycloalkyl is defined as above and which is linked to a $C_{1-n}$-alkoxy group through a carbon atom of the $C_{1-n}$-alkoxy group. Examples of such groups include cyclopropylmethyloxy, cyclobutylethyloxy, cyclopentylmethyloxy, cyclohexylmethyloxy, cyclohexylethyloxy etc.

The term $C_{3-n}$-cycloalkenyl denotes a $C_{3-n}$-cycloalkyl group which is defined as above and additionally has at least one C=C double bond, but is not aromatic by nature.

The term heterocyclyl used in this application denotes a saturated five-, six- or seven-membered ring system or a 5-12 membered bicyclic ring system which includes one, two, three or four heteroatoms, selected from N, O and/or S, such as for example a morpholinyl, piperidinyl, piperazinyl, thiomorpholinyl, oxathianyl, dithianyl, dioxanyl, pyrrolidinyl, tetrahydrofuranyl, dioxolanyl, oxathiolanyl, imidazolidinyl, tetrahydropyranyl, pyrrolinyl, tetrahydrothienyl, oxazolidinyl, homopiperazinyl, homopiperidinyl, homomorpholinyl, homothiomorpholinyl, azetidinyl, 1,3-diazacyclohexanyl or pyrazolidinyl group.

The term aryl used in this application denotes a phenyl, biphenyl, indanyl, indenyl, 1,2,3,4-tetrahydronaphthyl or naphthyl group.

The term heteroaryl used in this application denotes a heterocyclic, mono- or bicyclic aromatic ring system which includes in addition to at least one C atom one or more heteroatoms selected from N, O and/or S, wherein the term heteroaryl also includes the partially hydrogenated heterocyclic, aromatic ring systems. Examples of such groups are pyrrolyl, furanyl, thienyl, pyridyl-N-oxide, thiazolyl, imidazolyl, oxazolyl, triazinyl, triazolyl, 1,2,4-oxadiazoyl, 1,3,4-oxadiazoyl, 1,2,5-oxadiazoyl, isothiazolyl, isoxazolyl, 1,2,4-thiadiazolyl, 1,3,4-thiadiazolyl, 1,2,5-thiadiazolyl, pyrazolyl, pyrimidyl, pyridazinyl, pyrazinyl, tetrazolyl, pyridyl, indolyl, isoindoyl, indolizinyl, imidazopyridinyl, imidazo[1,2-a]pyridinyl, pyrrolopyrimidinyl, purinyl, pyridopyrimidinyl, pteridinyl, pyrimidopyrimidinyl, benzofuranyl, benzothienyl, quinolinyl, isoquinolinyl, quinazolinyl, quinoxalinyl, cinnolinyl, phthalazinyl, isobenzofuranyl, isobenzothienyl, thieno[3,2-b]thiophenyl, thieno[3,2-b]pyrrolyl, thieno[2,3-d]imidazolyl, naphthyridinyl, indazolyl, pyrrolopyridinyl, oxazolopyridinyl, benzimidazolyl, benzoxazolyl, benzisoxazolyl, benzothiazolyl, benzoisothiazolyl, benzoxadiazolyl, benzothiadiazolyl, 1,3-benzodioxolyl, 2,3- dihydrobenzofuranyl, 1,3-dihydroisobenzofuranyl, 2,3-dihydrobenzo[1,4]dioxinyl, 3,4-dihydrobenzo[1,4]oxazinyl, benzo[1,4]-oxazinyl, 2,3-dihydroindolyl, 2,3-dihydroisoindolyl, 1,2,3,4-tetrahydroquinolinyl, 1,2,3,4-tetrahydroisoquinolinyl, 2-oxo-2,3-dihydrobenzimidazolyl, 2-oxo-2,3-dihydroindolyl, pyrazolo[1,5-a]pyridinyl, pyrazolo[1,5-a]pyrimidinyl, chromanyl, chromenyl, chromonyl, isochromenyl, isochromanyl, dihydroquinolin-4-onyl, dihydroquinolin-2-onyl, quinolin-4-onyl, isoquinolin-2-onyl, imidazo[1,2-a]pyrazinyl, 1-oxoindanyl, benzoxazol-2-onyl, imidazo[4,5-d]thiazolyl or 6,7-dihydropyrrolizinyl groups.

Preferred heteroaryl groups are furanyl, thienyl, thiazolyl, imidazolyl, isoxazolyl, pyrazolyl, pyridyl, indolyl, benzofuranyl, 1,3-benzodioxolyl, 2,3-dihydrobenzofuranyl and 2,3-dihydrobenzo[1,4]dioxinyl.

The definition pyrazole includes the isomers 1H-, 3H- and 4H-pyrazole. Preferably pyrazolyl denotes 1H-pyrazolyl.

The definition imidazole includes the isomers 1H-, 2H- and 4H-imidazole. A preferred definition of imidazolyl is 1H-imidazolyl.

The definition triazole includes the isomers 1H-, 3H- and 4H-[1,2,4]-triazole as well as 1H-, 2H- and 4H-[1,2,3]-triazole. The definition triazolyl therefore includes 1H-[1,2,4]-triazol-1-, -3- and -5-yl, 3H-[1,2,4]-triazol-3- and -5-yl, 4H[1,2,4]-triazol-3-, -4- and -5-yl, 1H-[1,2,3]-triazol-1-, -4- and -5-yl, 2H[1,2,3]-triazol-2-, -4- and -5-yl as well as 4H-[1,2,3]-triazol-4- and -5-yl.

The term tetrazole includes the isomers 1H-, 2H- and 5H-tetrazole. The definition tetrazolyl therefore includes 1H-tetrazol-1- and -5-yl, 2H-tetrazol-2- and -5-yl and 5H-tetrazol-5-yl.

The definition indole includes the isomers 1H- and 3H-indole. The term indolyl preferably denotes 1H-indol-1-yl.

The term isoindole includes the isomers 1H- and 2H-isoindole.

In general, the bond to one of the above-mentioned heterocyclic or heteroaromatic groups may be effected via a C atom or optionally an N atom.

The style of writing used in which in the group

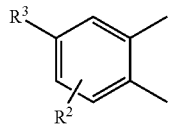

a bond of a substituent $R^2$ is shown towards the centre of the phenyl group denotes, unless stated otherwise, that the substituent $R^2$ may be bound to every free position of the phenyl group carrying an H atom.

The groups and substituents described hereinbefore may be mono- or polysubstituted by fluorine in the manner described. Preferred fluorinated alkyl groups are fluoromethyl, difluoromethyl and trifluoromethyl. Preferred fluorinated alkoxy groups are fluoromethoxy, difluoromethoxy and trifluoromethoxy. Preferred fluorinated alkylsulphinyl and alkylsulphonyl groups are trifluoromethylsulphinyl and trifluoromethylsulphonyl.

The compounds of the instant application are useful for manufacturing a medicament for the prevention and/or treatment of diseases and/or conditions wherein the inhibition of the cleavage of APP (Amyloid Precursor Protein) mediated by β-secretase is of therapeutic benefit.

Preferred is the manufacturing of a medicament for the prevention and/or treatment of Alzheimer's disease (AD) and other diseases which are associated with the abnormal processing of APP or aggregation of Abeta peptide, as well as diseases which can be treated or prevented by the inhibition of β-secretase, particularly AD.

Further preferred is the manufacturing of a medicament for the prevention and/or treatment of e.g. MCI ("mild cognitive impairment"), trisomy 21 (Down's syndrome), cerebral amyloid angiopathy, degenerative dementias, hereditary cerebral haemorrhage with amyloidosis, Dutch type (HCHWA-D), Alzheimer's dementia with Lewy bodies, trauma, stroke, pancreatitis, Inclusion Body Myositis (IBM), and other peripheral amyloidoses, diabetes and arteriosclerosis, most preferably AD.

Other features and advantages of the present invention will become apparent from the following more detailed Examples which illustrate, by way of example, the principles of the invention.

Preparation

The compounds according to the invention may be obtained using the methods of synthesis known in principle from starting compounds known to the skilled man (cf. for example: Houben Weyl—Methods of Organic Chemistry, Vol. E22, Synthesis of Peptides and Peptidomimetics, M. Goodman, A. Felix, L. Moroder, C. Toniolo Eds., Georg Thieme Verlag Stuttgart, New York). The skilled man knowing the structure of the compounds according to the invention will be able to synthesise them from known starting materials without any further information. Thus, the compounds may be obtained by the methods of preparation described hereinafter.

Amines 1 and amines 2 which are intermediates for the synthesis of compounds of formula 1 can be prepared as described in WO 06-017836, WO 07-050612 and E. Baxter et al., J. Med. Chem. 2007, 50(18), 4261-4264.

Scheme A illustrates as an example the preparation of amines 1, which are intermediates for the synthesis of compounds of formula 1.

A known Boc-protected amino-aldehyde or an amino-aldehyde which can be obtained according to literature procedures or in analogy to literature procedures is elongated by a Wittig reaction or Wittig-Horner-Emmons reaction using a suitable base preferably sodium hydride. The obtained olefin is catalytically hydrogenated and the ester subsequently saponified. The resulting acid is coupled with an amine bearing R6 and R7 under standard coupling conditions, e.g. using TBTU or EDC. After this the N-protection group is removed, e.g. the Boc-protection group is cleaved off under acidic conditions, to yield the amine 1.

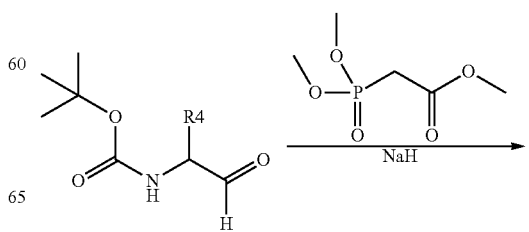

Scheme A

-continued

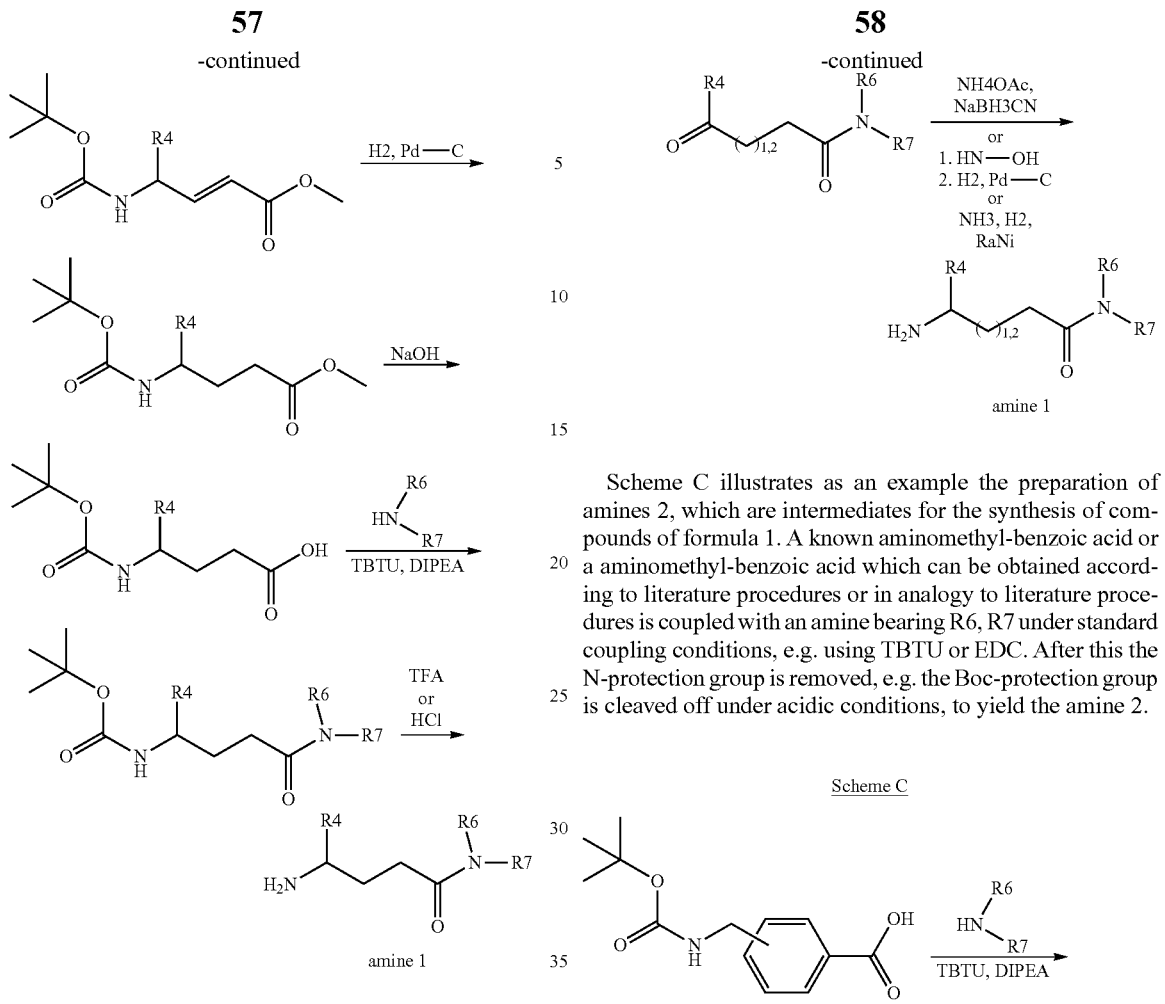

amine 1

Scheme B illustrates as a further example the preparation of amines 1, which are intermediates for the synthesis of compounds of formula 1. Succinic acid anhydride or glutaric acid anhydride is reacted with a Grignard reagent bearing R4. The resulting acid is coupled with an amine bearing R6, R7 under standard coupling conditions, e.g. using TBTU or EDC. After this the carbonyl group is converted to the amine via a reductive amination, e.g. using sodium cyano borohydride or sodium triacetoxy-borohydride together with ammonium acetate or by using ammonia/hydrogen together with a suitable catalyst e.g. Raney-Nickel, to yield the amine 2. As an alternative the last step can be carried out in a two step fashion, e.g. the carbonyl is reacted with hydroxylamine to yield the oxime which is then reduced to the amine 1 by catalytic hydrogenation using e.g. palladium on carbon as a catalyst.

Scheme B

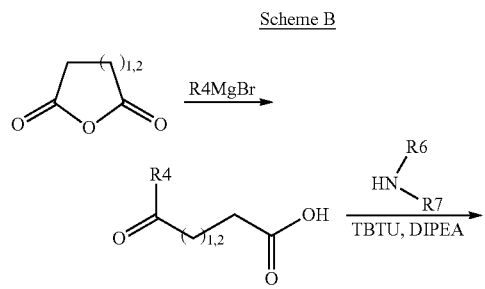

Scheme C illustrates as an example the preparation of amines 2, which are intermediates for the synthesis of compounds of formula 1. A known aminomethyl-benzoic acid or a aminomethyl-benzoic acid which can be obtained according to literature procedures or in analogy to literature procedures is coupled with an amine bearing R6, R7 under standard coupling conditions, e.g. using TBTU or EDC. After this the N-protection group is removed, e.g. the Boc-protection group is cleaved off under acidic conditions, to yield the amine 2.

Scheme D illustrates as an example the preparation of compounds of formula 1. An optionally substituted 2,4-difluoro-1-nitro-benzene 1 is reacted with amine 1 or amine 2 in the presence of a suitable base, preferably triethylamine or potassium-carbonate. The resulting 5-fluoro-2-nitro-phenylamine is reacted with R12-OH in the presence of a base. In case of R12-OH being a phenol potassium-carbonate is preferred. Subsequently the nitro group is reduced, preferably by hydrogen in the presence of a catalyst preferably palladium on carbon or Raney-Nickel. In the final step the compounds of formula 1 are obtained by cyclisation with bromocyane.

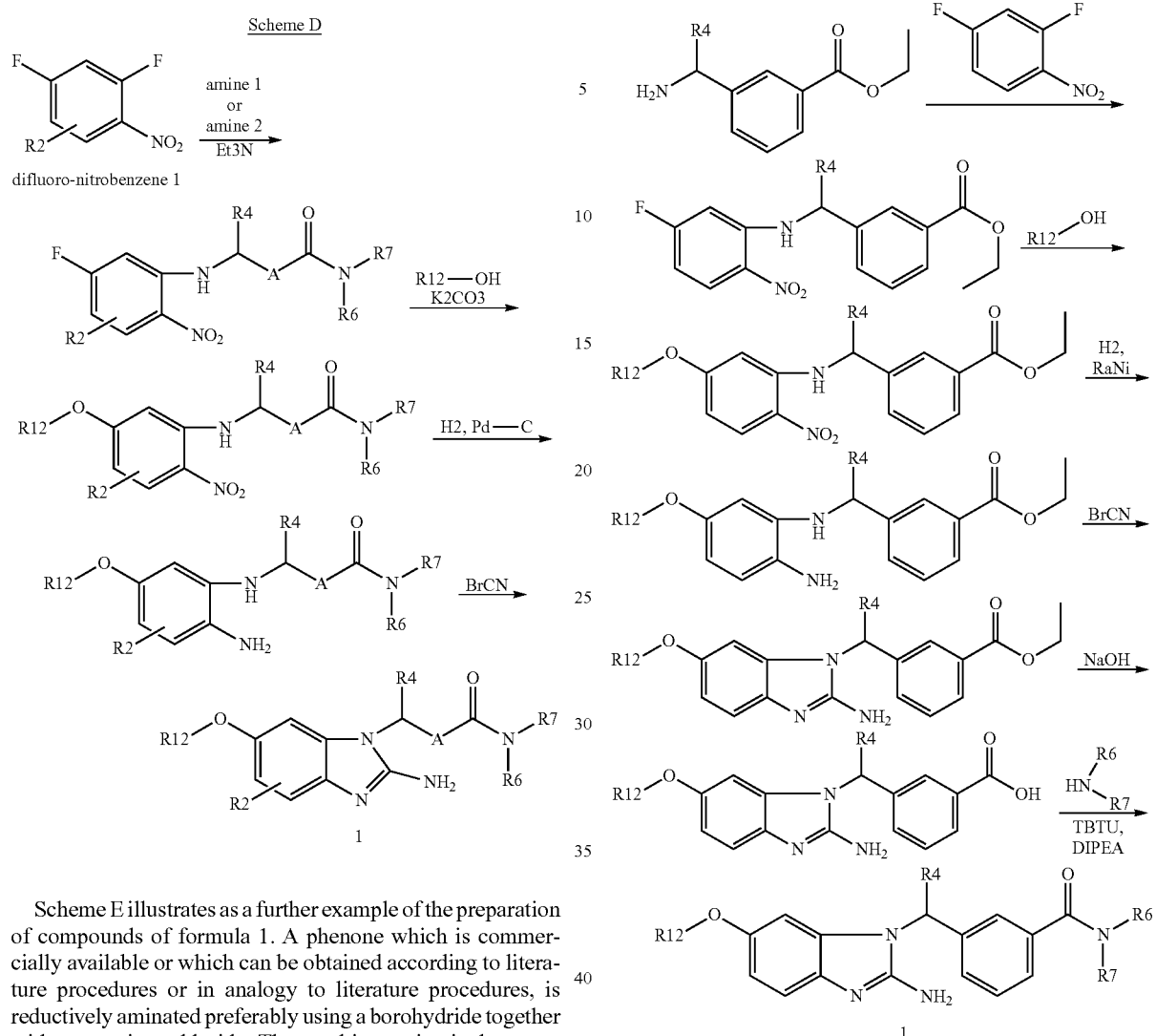

Scheme E illustrates as a further example of the preparation of compounds of formula 1. A phenone which is commercially available or which can be obtained according to literature procedures or in analogy to literature procedures, is reductively aminated preferably using a borohydride together with ammonium-chloride. The resulting amine is then condensed with 2,4-difluoronitro-benzene in the presence of a suitable base, preferably potassium-carbonate. The resulting 5-fluoro-2-nitro-phenylamine is reacted with R12-OH in the presence of a base. In case of R12-OH being a phenol potassium-carbonate is preferred. Subsequently the nitro group is reduced, preferably by hydrogen in the presence of a catalyst preferably palladium on carbon or Raney-Nickel. In the next step the diamine is cyclised with bromocyane to the amino-benzimidazole. After this the ester is hydrolyzed to the corresponding acid. The acid is then coupled with an amine bearing the substituents R6 and R7 under standard coupling conditions, e.g. using TBTU or EDC, to yield the final product of formula 1.

Scheme E

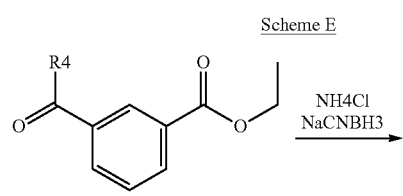

Scheme F illustrates as a further example of the preparation of compounds of formula 1. An optionally substituted 2,4-difluoro-1-nitro-benzene is reacted with an amino-alcohol which is commercially available or which can be obtained according to literature procedures or in analogy to literature procedures in the presence of a suitable base, preferably triethylamine. The resulting 5-fluoro-2-nitro-phenylamino-alcohol is then reacted with R12-OH in the presence of a base. In case of R12-OH being a phenol potassium-carbonate is preferred. The resulting phenylamino-alcohol is then oxidized to the corresponding aldehyde with a suitable oxidising reagent, preferably using the Dess-Martin periodinane reagent. The aldehyde is then elongated to the unsaturated ester by a Wittig reaction or Wittig-Horner-Emmons reaction using a suitable base preferably sodium hydride. In a hydrogenation reaction using a suitable catalyst, preferably palladium on carbon, the olefin and the nitro group are reduced. In the next step the diamine is cyclised with bromocyane to the amino-benzimidazole. After this the ester is hydrolysed to the corresponding acid. The acid is then coupled with an amine bearing the substituents R6 and R6 under standard coupling conditions, e.g. using TBTU or EDC, to yield the final product of formula 1.

Scheme F

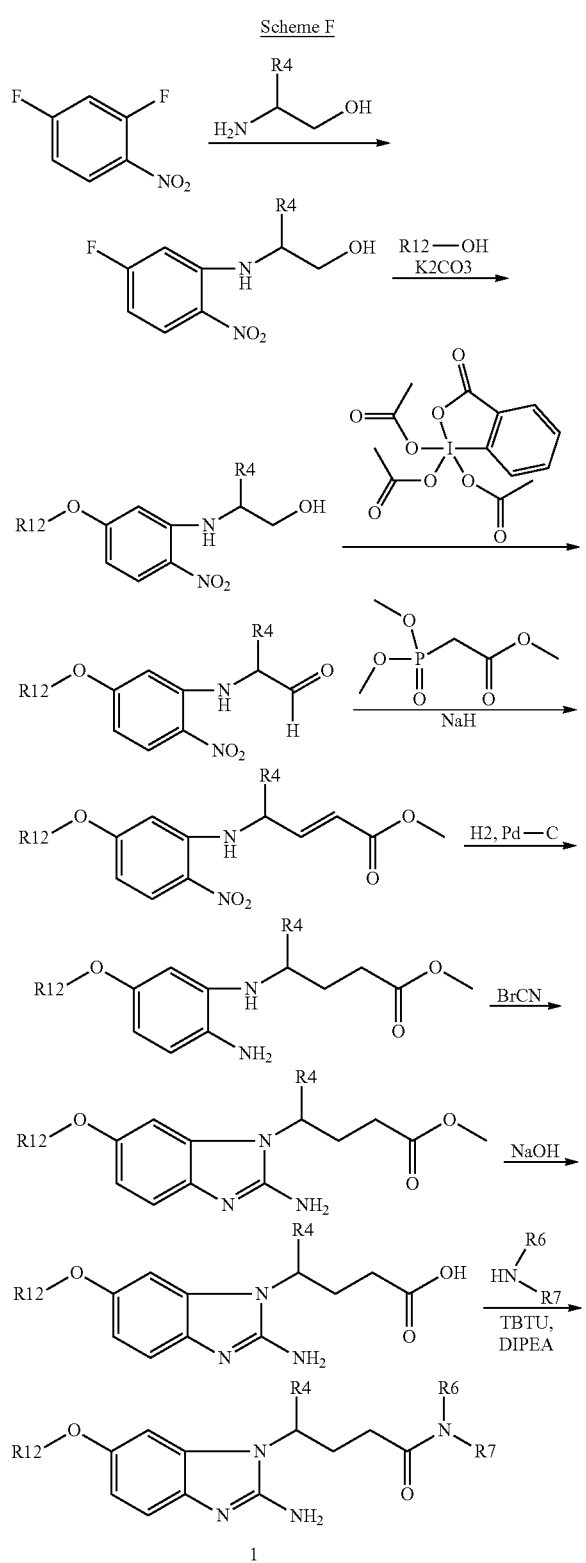

Scheme G illustrates as an example the preparation of ethers, which are intermediates for the synthesis of compounds of formula 1. This procedure is preferably used when R12-OH is an aliphatic alcohol. A 2,4-difluoro-1-nitro-benzene is reacted with amine 1 or amine 2 in the presence of a suitable base, preferably triethylamine. The resulting 5-fluoro-2-nitro-phenylamine is reacted with 2-methanesulfonyl-ethanol in the presence of sodiumhydride following a literature procedure (J. F. Rogers et al., Tetrahedron Letters, 2002, 43, 3585-3587.) to yield the nitro-phenol. The phenol is then reacted with R12-OH in the presence of a strong base, preferably sodiumhydride. The resulting ethers are then further processed to the compounds of formula 1 as in scheme D.

Scheme G

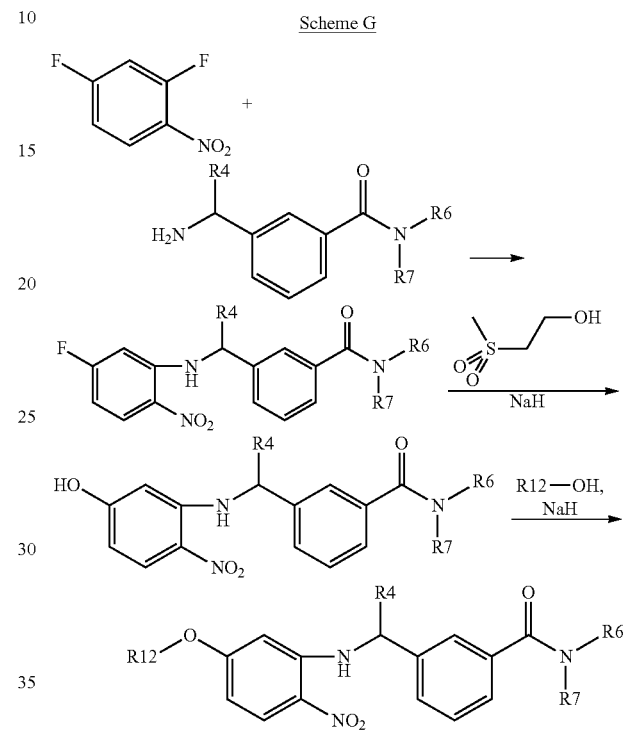

Scheme H illustrates as an example the preparation of N-methyl-amines, which are intermediates for the synthesis of compounds of formula 1. Thus, a primary amine is boc-protected e.g. by $Boc_2O$ in the presence of a base. The resulting carbamate is reduced to the N-methylamine e.g. by lithium aluminiumhydride.

Scheme H

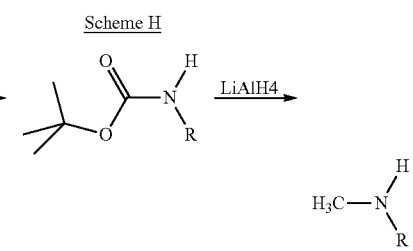

EXAMPLES

In the description of the examples the following abbreviations are used:

| | |
|---|---|
| Boc | tert.-Butoxycarbonyl |
| DIPEA | N-ethyl-diisopropylamine |
| DCM | dichloromethane |
| DMF | dimethylformamide |

-continued

| | |
|---|---|
| d | days |
| ESI-MS | electro-spray ionization mass spectrometry |
| h | hours |
| HPLC | high performance liquid chromatography |
| HPLC-MS | high performance liquid chromatography with mass detection |
| min | minutes |
| MPLC | medium pressure liquid chromatography |
| NMP | N-methylpyrrolidone |
| Rf | retention factor |
| RT | retention time |
| TBTU | O-(benzotriazol-1-yl)-N,N,N',N'-tetramethyluronium tetrafluoroborate |
| TFA | trifluoroacetic acid |
| THF | tetrahydrofuran |
| tlc | thin layer chromatography |

The HPLC-data are obtained under the following conditions:

Method 1s:

| instrument | | column | |
|---|---|---|---|
| Waters Alliance 2695 | | Varian Microsorb 100 C18 | |
| PDA Detector 2996 | | particle Size 3 μm | |
| Waters Micromass ZQ | | length 30 mm | |
| | | internal diameter 4.6 mm | |

| gradient time [min] | % water + 0.13% TFA | % acetonitrile | flux [ml/min.] |
|---|---|---|---|
| 0 | 95 | 5 | 3.5 |
| 0.18 | 95 | 5 | 3.5 |
| 2 | 2 | 98 | 3.5 |
| 2.2 | 2 | 98 | 3.5 |
| 2.3 | 95 | 5 | 3.5 |
| 2.5 | 95 | 5 | 3.5 |
| 2.6 | 95 | 5 | 0.5 |
| 6.5 | 95 | 5 | 1.00 |

Method Chromolith:

| instrument | | Column | |
|---|---|---|---|
| Waters Alliance 2695 | | Merck, Darmstadt | |
| PDA Detector 2996 | | Chromolith Performance | |
| Waters Micromass ZQ | | RP18e | |
| | | length 100 mm | |
| | | internal diameter 3 mm | |

| gradient time [min] | % water + 0.13% TFA | % acetonitrile | flux [ml/min.] |
|---|---|---|---|
| 0 | 95 | 5 | 3.5 |
| 0.2 | 95 | 5 | 3.5 |
| 1.6 | 2 | 98 | 3.5 |
| 1.9 | 2 | 98 | 3.5 |
| 2 | 95 | 5 | 3.5 |
| 2.2 | 95 | 5 | 3.5 |
| 2.3 | 95 | 5 | 0.1 |

The crude compounds are purified by the following HPLC-methods:

Method 1: Gilson, UV-VIS detector, column: Microsorb C18, 8 μm, 50×160 mm, gradient: ($H_2O$, 0.15% TFA)/acetonitrile=90:10 to acetonitrile=100%.

Method 2: Gilson, UV-VIS detector, column: Microsorb C18, 8 μm, 21.4×250 mm, gradient: ($H_2O$, 0.15% TFA)/acetonitrile=90:10 to acetonitrile=100%.

Method 3: Waters, UV-VIS detector, column: X-bridge, 5 μm, 50×160 mm, gradient: ($H_2O$, 0.18% $NH_3$)/acetonitrile=90:10 to acetonitrile=100%.

Microwave heating was done using Biotage Initiator Sixty (Biotage AB, Uppsala, Sweden).

Example 1A

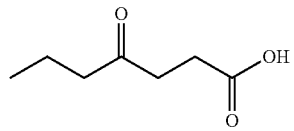

A mixture of 30 g (300 mmol) succinic acid anhydride and 5.83 g (30 mmol) of copper-(I)-iodide is cooled to −20° C. and a Grignard reagent prepared from 49.3 g (401 mmol) 1-bromo-propane and 8.74 g (360 mmol) magnesium turnings in 200 ml diethylether is added. The mixture is allowed to warm to room temperature and is stirred for 14 h. 250 ml 1 M hydrochloric acid is added and the mixture is stirred for 30 min. The precipitate is removed and the solution is extracted with DCM. The combined organic phases are dried and evaporated. The product is obtained as a yellow oil that becomes a solid slowly. It is used as such in the next step.

yield: 26 g (29%)

Example 1B

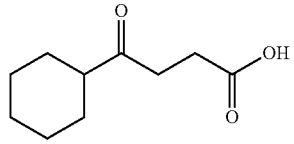 [SMILES: O=C(O)CCC(=O)C1CCCCC1]

A mixture of 60 g (600 mmol) succinic acid anhydride and 11.7 g (60 mmol) of copper-(I)-iodide is cooled to −20° C. and a Grignard reagent prepared from 90 ml (719 mmol) cyclohexyl-bromide and 17.5 g (720 mmol) magnesium turnings in 400 ml diethylether is added. The mixture is allowed to warm to room temperature and is stirred for 14 h. 250 ml 1 M hydrochloric acid are added and the mixture is stirred for 30 min. The precipitate is removed and the solution is extracted with DCM. The combined organic phases are dried and evaporated. The product is obtained as a yellow oil that becomes a solid slowly. It is used as such in the next step.

yield: 73 g (66%)

LC-MS (Method 1s): RT=1.29 min

MS (ESI pos): m/z=185 $(M+H)^+$

Example 2A

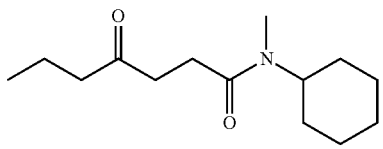 [SMILES: CCCC(=O)CCC(=O)N(C)C1CCCCC1]

To a solution of 25 g (173 mmol) 1A in 150 ml THF are added 81.2 g (96%, 243 mmol) TBTU and 90.2 ml (98%, 520 mmol) DIPEA. The mixture is stirred for 1.5 h and 32.7 ml (260 mmol) N-methyl-cyclohexylamine is added. The mixture is stirred for 14 h and evaporated. The residue is dissolved in DCM, washed with 0.1 M hydrochloric acid and water, dried and evaporated. The mixture is dissolved in acetonitrile/water/TFA (50:50:0.1) and then purified by preparative HPLC (method 1).

yield: 9.50 g (23%)
LC-MS (Method 1s): RT=1.42 min
MS (ESI pos): m/z=240 (M+H)+

Example 2B

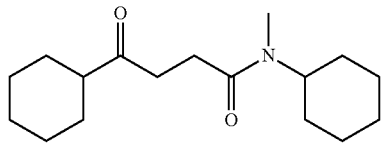 [SMILES: CN(C(=O)CCC(=O)C1CCCCC1)C1CCCCC1]

To a solution of 35 g (190 mmol) 1B in 250 ml THF are added 89.0 g (96%, 266 mmol) TBTU and 98.9 ml (98%, 570 mmol) DIPEA. The mixture is stirred for 1.5 h and 35.8 ml (260 mmol) N-methyl-cyclohexylamine is added. The mixture is stirred for 14 h and evaporated. The residue is dissolved in DCM, washed with 0.1 M hydrochloric acid and water, dried and evaporated. The mixture is dissolved in acetonitrile/water/TFA (50:50:0.1) and then purified by preparative HPLC (method 1).

yield: 13.5 g (25%)
LC-MS (Method 1s): RT=1.66 min
MS (ESI pos): m/z=280 (M+H)+

Example 3A

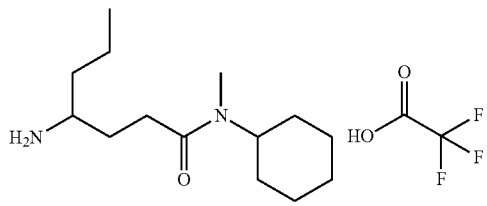

2.00 g (8.36 mmol) 2A are hydrogenated with 20 ml of a saturated solution of ammonia in methanol over 750 mg Raney-Nickel for 24 h. The mixture is filtered, evaporated and purified by preparative HPLC (method 1). The product is obtained as TFA salt.

yield: 1.98 g (67%)
LC-MS (Method 1s): RT=1.10 min
MS (ESI pos): m/z=241 (M+H)+

Example 3B

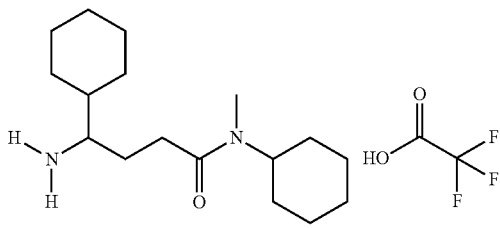

To a solution of 5.00 g (17.9 mmol) 2B in 10 ml methanol are added 14.2 g (215 mmol) sodium cyanoborohydride, 22.1 g (286 mmol) ammonium acetate and 12.4 ml (214 mmol) acetic acid. The mixture is stirred at room temperature for 14 h. The mixture is filtered, evaporated and purified by preparative HPLC (method 1). The product is obtained as TFA salt.

yield: 1.48 g (28%)
LC-MS (Method 1s): RT=1.26 min
MS (ESI pos): m/z=281 (M+H)+

Example 3C

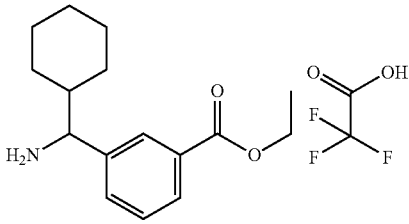

To a solution of 9.00 g (34.6 mmol) 3-cyclohexanecarbonyl-benzoic acid ethyl ester (Rieke Metals, Inc., 1001 Kingbird Road, Lincoln, Nebr. 68521, USA) in 100 ml methanol are added 11.0 g (175 mmol) sodium cyanoborohydride and 17.0 g (220 mmol) ammonium acetate. The mixture is stirred at room temperature for 14 d. The mixture is adjusted to pH 1 with 4M HCl (caution: HCN evolution. HCN is toxic). After 12 h at room temperature methanol is evaporated under reduced pressure. The remaining aqueous mixture is adjusted to pH 7 using sodium hydrogencarbonate and extracted with DCM. The organic layer is separated, dried and the solvent is evaporated under reduced pressure. The product obtained is purified by preparative HPLC (method 1). The product is obtained as TFA salt.

yield: 7.67 g (59%)
LC-MS (Method 1s): RT=1.26 min
MS (ESI pos): m/z=262 (M+H)+

Example 4A

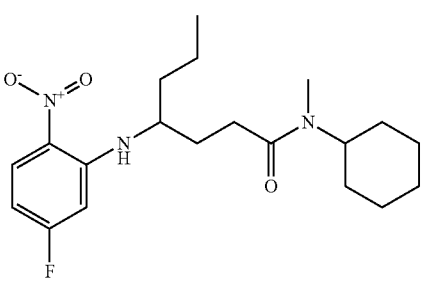 [SMILES: CCCC(CCC(=O)N(C)C1CCCCC1)Nc1cc(F)ccc1[N+](=O)[O-]]

1.50 g (6.24 mmol) 3A are stirred together with 993 mg (6.24 mmol) 2,4-difluoro-nitrobenzene and 21 ml triethylamine in 10 ml DMF for 36 h. The mixture is evaporated and the residue purified by preparative HPLC (method 1).

yield: 1.30 g (55%)
LC-MS (Method 1s): RT=1.90 min
MS (ESI pos): m/z=380 (M+H)+

Example 4B

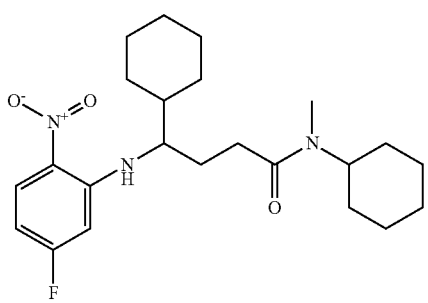 [SMILES: CN(C(=O)CCC(Nc1cc(F)ccc1[N+](=O)[O-])C1CCCCC1)C1CCCCC1]

695 mg (2.48 mmol) 3B are stirred together with 394 mg (2.48 mmol) 2,4-difluoro-nitrobenzene and 8.2 ml triethylamine in 5 ml DMF for 14 h. The mixture is evaporated and the residue purified by preparative HPLC (method 1).
yield: 362 mg (35%)
LC-MS (Method 1s): RT=2.11 min
MS (ESI pos): m/z=420 (M+H)⁺

Example 5A

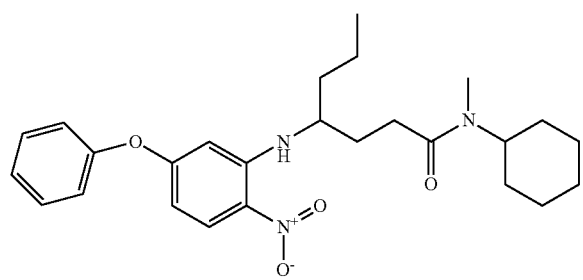 [SMILES: CCCC(CCC(=O)N(C)C1CCCCC1)Nc1cc(Oc2ccccc2)ccc1[N+](=O)[O-]]

A mixture of 375 mg (0.99 mmol) 4A, 93 mg (0.99 mmol) phenol and 171 mg (1.23 mmol) potassium-carbonate in 5 ml DMF is stirred at 120° C. for 14 h. The mixture is evaporated and the residue is dissolved in DCM. The DCM-phase is washed with water, the organic layer separated, dried and evaporated. The product is used as such in the next step.
yield: 447 mg (100%)
LC-MS (Method 1s): RT=2.07 min
MS (ESI pos): m/z=454 (M+H)⁺

Example 5B

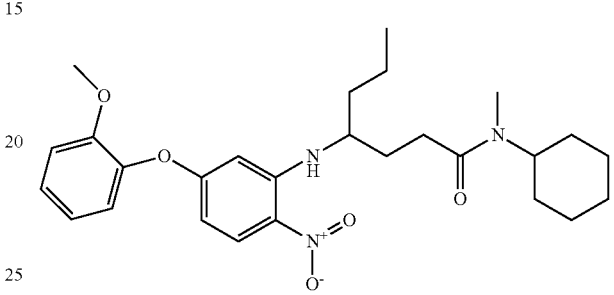

A mixture of 150 mg (0.40 mmol) 4A, 59 mg (0.47 mmol) 2-methoxy-phenol and 655 mg (4.74 mmol) potassium-carbonate in 3 ml DMF is stirred at 120° C. for 14 h. The mixture is evaporated and the residue is dissolved in DCM. The DCM-phase is washed with water, the organic layer separated, dried and evaporated. The product is used as such in the next step.
yield: 181 mg (94%)
LC-MS (Method 1s): RT=1.99 min
MS (ESI pos): m/z=484 (M+H)⁺

The following products are synthesized in analogy to the preparation of example 5A, using 4A and the corresponding phenol as starting materials:

| example | structure | phenol | yield | RT (LC-MS; Method 1s) | MS(ESI pos, m/z) |
|---|---|---|---|---|---|
| 5C | 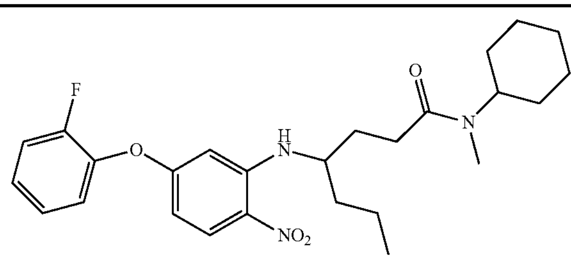 | 2-Fluoro-phenol | 115 mg (100%) | 2.05 min | 472 (M + H)⁺ |
| 5D | 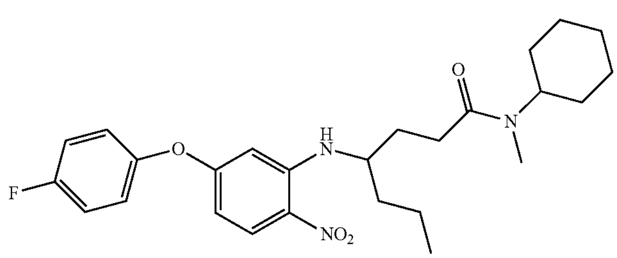 [SMILES: CCCC(CCC(=O)N(C)C1CCCCC1)Nc1cc(Oc2ccc(F)cc2)ccc1[N+](=O)[O-]] | 4-Fluoro-phenol | 125 mg (100%) | 2.14 min | |

| example | structure | phenol | yield | RT (LC-MS; Method 1s) | MS(ESI pos, m/z) |
|---|---|---|---|---|---|
| 5E | 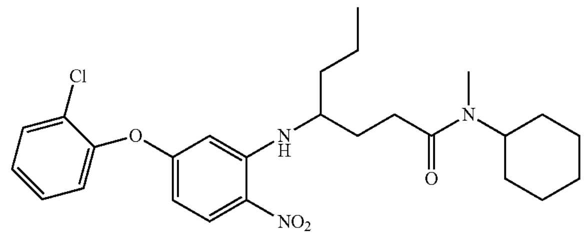 [SMILES: CCCC(CCC(=O)N(C)C1CCCCC1)Nc1cc(Oc2ccccc2Cl)ccc1[N+](=O)[O-]] | 2-Chloro-phenol | 120 mg (100%) | 2.11 min | 488/490 (Cl) (M + H)+ |

The following products are synthesized in analogy to the preparation of example 5A, using 4B and the corresponding phenol as starting materials:

| example | structure | phenol | yield | RT (LC-MS; Method) | MS(ESI pos, m/z) |
|---|---|---|---|---|---|
| 5F | 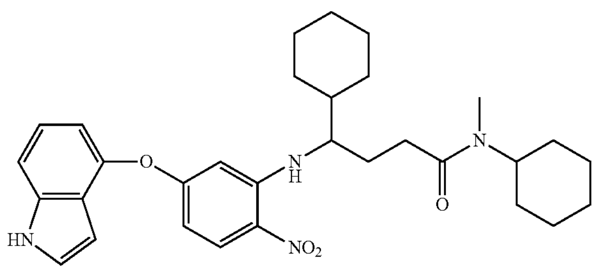 [SMILES: CN(C(=O)CCC(Nc1cc(Oc2cccc3[nH]ccc23)ccc1[N+](=O)[O-])C1CCCCC1)C1CCCCC1] | 4-hydroxy-indole | 75 mg (66%) | 1.90 min (chromolith) | 531 (M + H)+ |

Example 6A

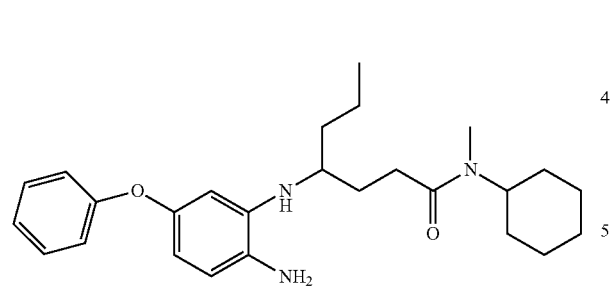

Example 6B

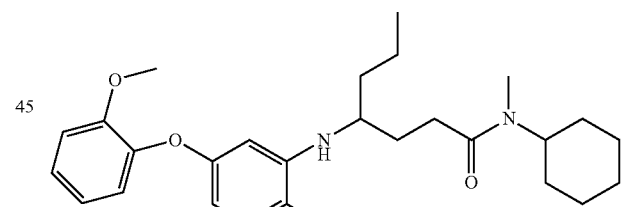

447 mg (0.98 mmol) 5A are hydrogenated in 10 ml methanol over 250 mg palladium on activated carbon (10%) for 18 h. The mixture is filtered and the solvent evaporated. The product is used as such in the next step.

yield: 417 mg (100%)

LC-MS (Method 1s): RT=1.57 min

MS (ESI pos): m/z=424 (M+H)+

151 mg (0.37 mmol) 5B are hydrogenated in 10 ml methanol over 100 mg palladium on activated carbon (10%) for 14 h. The mixture is filtered and the solvent evaporated. The product is used as such in the next step.

yield: 170 mg (100%)

LC-MS (Method 1s): RT=1.54 min

MS (ESI pos): m/z=454 (M+H)+

The following products are synthesized in analogy to the preparation of example 6A, using the corresponding nitrobenzenes as starting materials:

| example | structure | nitro-benzene | yield | RT (LC-MS; Method 1s) | MS(ESI pos, m/z) |
|---|---|---|---|---|---|
| 6C | 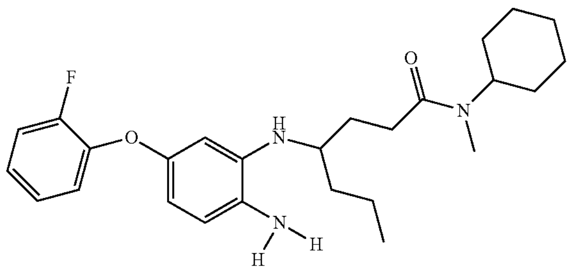 [SMILES: CCCC(CCC(=O)N(C)C1CCCCC1)Nc1cc(Oc2ccccc2F)ccc1N] | 5C | 110 mg (100%) | 1.67 min | |
| 6D | 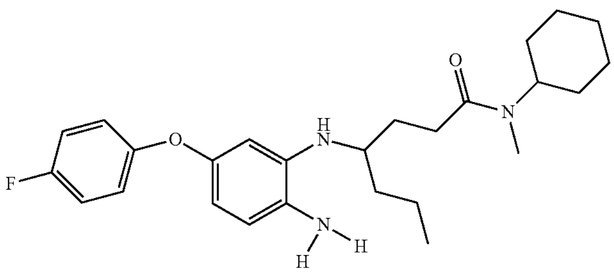 [SMILES: CCCC(CCC(=O)N(C)C1CCCCC1)Nc1cc(Oc2ccc(F)cc2)ccc1N] | 5D | 125 mg (100%) | 1.69 | |
| 6E | 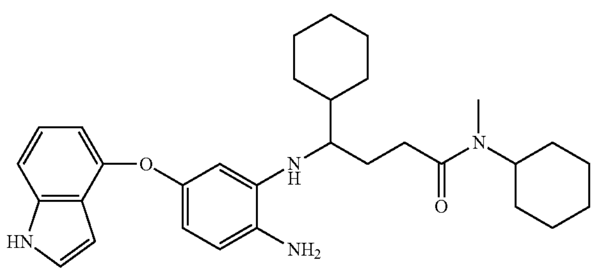 | 5F | 107 mg (100%) | 1.58 min | 503 |

Example 6F

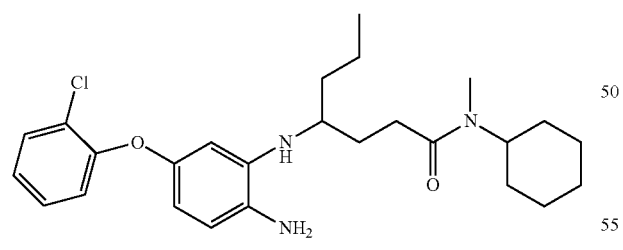

120 mg (0.25 mmol) 5E are stirred together with 555 mg (2.46 mmol) tin-(II)-chloride-dihydrate in 5 ml ethanol. After a few minutes a white precipitate is formed an 5 ml DMF is added. The mixture is warmed to 80° C. for 14 h. The mixture is filtered, the solvent evaporated and the residue treated with ethanol. The precipitate is removed and the solution evaporated. The product is used as such in the next step.

yield: 120 mg (100%)

LC-MS (Method 1s): RT=1.59 min

Example 7A

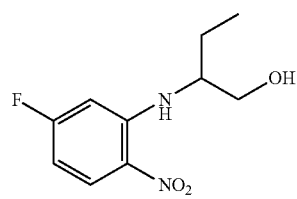 [SMILES: CCC(CO)Nc1cc(F)ccc1[N+](=O)[O-]]

7.03 ml (98%, 62.8 mmol) 2,4-difluoro-nitrobenzene and 5.60 g (62.8 mmol) 2-amino-1-butanol are stirred together with 22 ml (157 mmol) triethylamine in 30 ml DMF at 50° C. for 14 h. The mixture is used as such in the next step.

LC-MS (Method 1s): RT=1.46 min

MS (ESI pos): m/z=229 (M+H)$^+$

Example 7B

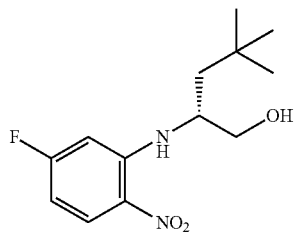 [SMILES: CC(C)(C)C[C@H](CO)Nc1cc(F)ccc1[N+](=O)[O-]]

2.75 g (17.3 mmol) 2,4-difluoro-nitrobenzene and 2.75 g 26A (17.3 mmol) are stirred together with 6 ml (43 mmol) triethylamine in 20 ml 1,4-dioxane at room temperature for 28 h. The solvent is removed and the product is purified by preparative HPLC (method 1). The fractions containing the product are combined and the solvent is evaporated to yield the product.
LC-MS (Method 1s): RT=1.64 min
MS (ESI pos): m/z=269 (M+H)$^+$

Example 8A

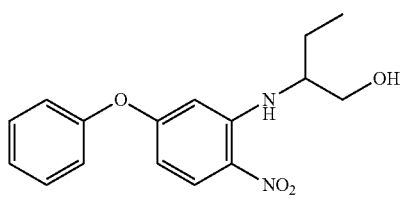 [SMILES: CCC(CO)Nc1cc(Oc2ccccc2)ccc1[N+](=O)[O-]]

To the mixture of example 7A 5.91 g (62.8 mmol) phenol and 9.55 g (69.1 mmol) potassium-carbonate are added. The mixture is stirred at 100° C. for 3 d. The mixture is filtered and the solution concentrated. The product is purified by preparative HPLC (method 1). The fractions containing the product are combined and the solvent removed to yield the product as a red oil.
yield: 11.0 g (58% for 2 steps)
LC-MS (Method 1s): RT=1.65 min
MS (ESI pos): m/z=303 (M+H)$^+$

Example 8B

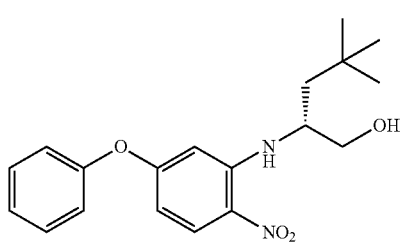 [SMILES: CC(C)(C)C[C@H](CO)Nc1cc(Oc2ccccc2)ccc1[N+](=O)[O-]]

To 2.10 g (7.77 mmol) 7B and 1.10 g (11.7 mmol) phenol dissolved in 5 ml DMF 1.18 g (8.55 mmol) potassium-carbonate are added. The mixture is stirred at room temperature 34 h. The mixture is filtered and the solution concentrated. The product is purified by preparative HPLC (method 1). The fractions containing the product are combined and the solvent removed to yield the product.
yield: 1.9 g (71%)
LC-MS (Method 1s): RT=1.86 min
MS (ESI pos): m/z=345 (M+H)$^+$

Example 9A

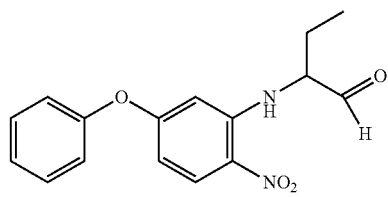 [SMILES: CCC(C=O)Nc1cc(Oc2ccccc2)ccc1[N+](=O)[O-]]

To a solution of 11.9 g (39.4 mmol) 8A in 100 ml DCM 18.5 g (97%, 42.3 mmol) Dess-Martin periodinane is added at 0° C. The mixture is stirred for 14 h after which saturated sodium thiosulphate and saturated sodium hydrogencarbonate solutions are added. After stirring for 10 min the organic layer is separated and the solvent is evaporated. The product is used as such in the next step.
yield: 11.2 g (95%)
LC-MS (Method 1s): RT=1.65 min
MS (ESI pos): m/z=301 (M+H)$^+$

Example 9B

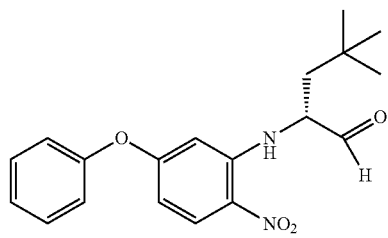 [SMILES: CC(C)(C)C[C@H](C=O)Nc1cc(Oc2ccccc2)ccc1[N+](=O)[O-]]

To a solution of 1.90 g (5.52 mmol) 8B in 10 ml DCM 2.57 g (6.07 mmol) Dess-Martin periodinane is added at room temperature. The mixture is stirred for 14 h after which saturated sodium thiosulphate and saturated sodium hydrogencarbonate solutions are added. After stirring for 10 min the organic layer is separated and the solvent is evaporated. The product is used as such in the next step.
yield: 2.2 g (100%)
MS (ESI pos): m/z=343 (M+H)$^+$

Example 10A

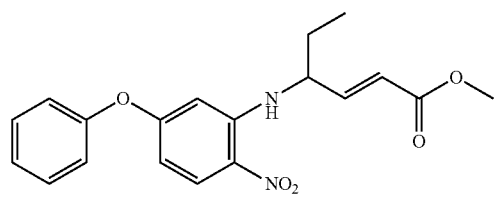 [SMILES: CCC(/C=C/C(=O)OC)Nc1cc(Oc2ccccc2)ccc1[N+](=O)[O-]]

100 ml THF are added under an atmosphere of nitrogen to 1.80 g (45 mmol) of sodium hydride (60% suspension in mineral oil). The mixture is cooled to 0° C. and a solution of 6.18 ml (98%, 37.4 mmol) trimethyl-phosphonoacetate in 20 ml THF is added. After this 150 ml of THF are added and the mixture is stirred for 10 min. A solution of 11.2 g (37.4 mmol) 9A in 30 ml THF is added slowly at 0° C. The mixture is allowed to warm to room temperature and is stirred for 14 h. 20 ml of water are added slowly and the THF is removed. To the residue ethyl acetate is added, the mixture is washed with water, dried and the solvent evaporated. The residue is purified by Flash-chromatography (silica gel, cyclohexane/ethyl acetate 8:2) to yield the product as a mixture of E and Z isomers.
yield: 7.13 g (54%)
LC-MS (Method 1s): RT=1.75 min
MS (ESI pos): m/z=357 (M+H)$^+$ Example 10B

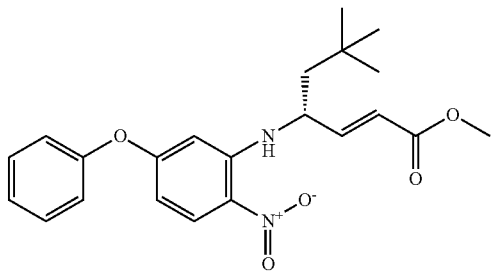 [SMILES: COC(=O)/C=C/[C@@H](CC(C)(C)C)Nc1cc(Oc2ccccc2)ccc1[N+](=O)[O-]]

10 ml THF are added under an atmosphere of nitrogen to 280 mg (7.01 mmol) of sodium hydride (60% suspension in mineral oil). The mixture is cooled to 0° C. and a solution of 0.97 ml (98%, 5.84 mmol) trimethyl-phosphonoacetate in 5 ml THF is added. The mixture is stirred for 10 min a 0° C. A solution of 2.00 g (5.84 mmol) 9B in 5 ml THF is added slowly at 0° C. The mixture is allowed to warm to room temperature and is stirred for 14 h. 20 ml of water are added slowly and the THF is removed. To the residue ethyl acetate is added, the mixture is washed with water, dried and the solvent evaporated. The product is used as such in the next step.
yield: 1.90 g (82%)
LC-MS (Method 1s): RT=2.06 min
MS (ESI pos): m/z=399 (M+H)$^+$ Example 11A

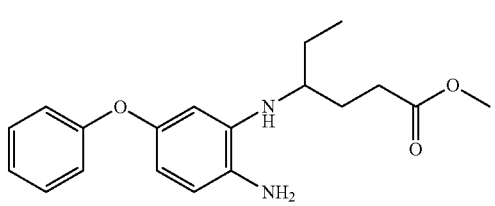 [SMILES: CCC(CCC(=O)OC)Nc1cc(Oc2ccccc2)ccc1N]

3.50 g (9.82 mmol) of 10A dissolved in 50 ml methanol are hydrogenated at room temperature and a pressure of 50 psi for 17 h over 500 mg palladium on activated carbon (10%). The mixture is filtered and the solvent evaporated. Purification by Flash-chromatography (silica gel, cyclohexane/ethyl acetate 9:1) gives the product as a dark oil.
yield: 7.13 g (54%)
LC-MS (Method 1s): RT=1.42 min
MS (ESI pos): m/z=329 (M+H)$^+$ Example 11B

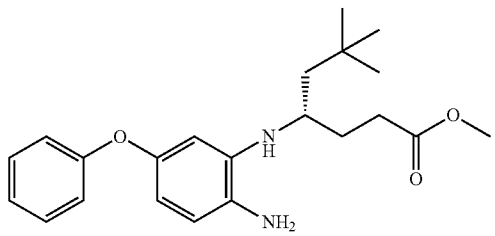 [SMILES: COC(=O)CC[C@@H](CC(C)(C)C)Nc1cc(Oc2ccccc2)ccc1N]

2.00 g (5.02 mmol) of 10B dissolved in 10 ml methanol are hydrogenated at room temperature and a pressure of 54 psi for 3 h over 100 mg palladium on activated carbon (10%). The mixture is filtered and the solvent evaporated.
yield: 2.00 g (100%)
LC-MS (Method 1s): RT=1.53 min
MS (ESI pos): m/z=371 (M+H)$^+$ Example 12A

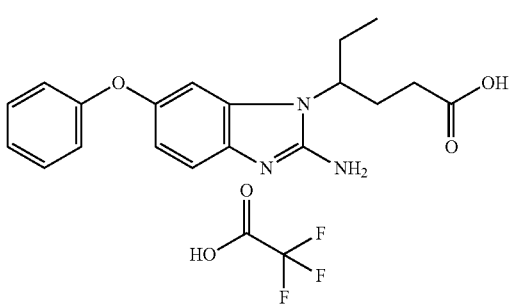

To a solution of 2.80 g (8.53 mmol) 11A in 20 ml ethanol 2.85 ml (8.55 mmol) of a 3 M solution of bromocyane in DCM and 500 µl of water is added. The mixture is stirred at room temperature for 3 h. After this 20 ml 4 M sodium hydroxide solution is added and the mixture is stirred for 2 h at room temperature. The ethanol is removed and the residue diluted with 150 ml of water and the mixture slowly acidified with 1 M hydrochloric acid. The mixture is extracted with DCM, the combined organic fractions are dried and the solvent evaporated. The residue is purified by preparative HPLC (method 1). Fractions containing the product are combined and lyophilized to yield the product as a TFA salt.
yield: 1.76 g (46%)
LC-MS (Method 1s): RT=1.22 min
MS (ESI pos): m/z=339 M$^+$, 340 (M+H)$^+$ Example 12B

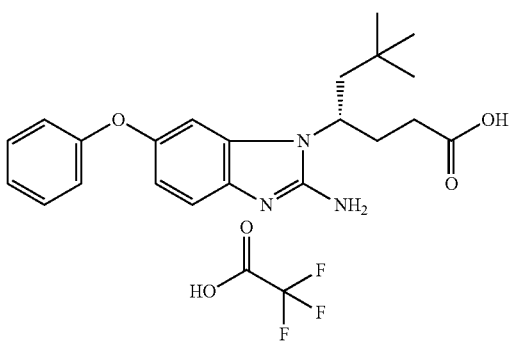

To a solution of 2.00 g (5.40 mmol) 11B in 5 ml ethanol 552 mg (5.40 mmol) bromocyane is added. The mixture is stirred at room temperature for 14 h. After this 3.5 ml 4 M sodium hydroxide solution is added and the mixture is stirred for 14 h at room temperature. The ethanol is removed and the residue diluted with 100 ml of water and the mixture slowly acidified with 1 M hydrochloric acid. The mixture is extracted with DCM, the combined organic fractions are dried and the solvent evaporated. The residue is purified by preparative HPLC (method 1). Fractions containing the product are combined and lyophilized to yield the product.

yield: 1.40 g (68%)
LC-MS (Method 1s): RT=1.39 min
MS (ESI pos): m/z=382 (M+H)$^+$ Example 12C

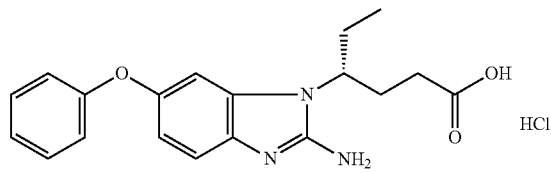 [SMILES: CC[C@H](CCC(=O)O)n1c(N)nc2ccc(Oc3ccccc3)cc21 ; Cl]

Example 12C is synthesized in analogy to example 12B. Instead of the amine 26A in example 7B (R)-2-amino-1-butanol is used. The product is treated with water/DCM and the mixture acidified with 4 M hydrochloric acid. The organic phase is separated and the aqueous phase extracted several times with DCM. The combined organic phases are dried, filtered and evaporated to yield the product as the hydrochloric acid salt.

yield: 3.71 g (70%)
LC-MS (Method 1s): RT=1.26 min
MS (ESI pos): m/z=340 (M+H)$^+$ Example 13A

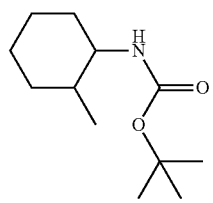

To a solution of 2.50 g (21.7 mmol) 2-methyl-cyclohexylamine in 30 ml THF 5.36 g (23.5 mmol) di-tert.-butyl-dicarbonate is added and the mixture is stirred 14 h at room temperature. The THF is removed and the residue dissolved in DCM and washed with water. The organic phase is dried and evaporated to yield the product as a solid.

yield: 5.00 g (100%)
tlc: Rf (silica gel, DCM/methanol=95:5)=0.82
MS (ESI pos): m/z=214 (M+H)$^+$ Example 13B

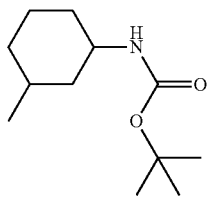

To a solution of 2.00 g (13.4 mmol) 3-methyl-cyclohexylamine-hydrochloride in 30 ml THF 3.31 g (14.7 mmol) di-tert.-butyl-dicarbonate and 2.10 ml (15.0 mmol) triethylamine is added and the mixture is stirred 14 h at room temperature. After this the mixture is heated to 65° C. for 3 h. The THF is removed and the residue dissolved in DCM and washed with water. The organic phase is dried and evaporated to yield the product as a yellow oil.

yield: 3.24 g (100%)
tlc: Rf (silica gel, DCM/methanol=95:5)=0.81
MS (ESI pos): m/z=214 (M+H)$^+$ The following products are synthesized in analogy to the preparation of example 13A, using the corresponding amine as starting materials:

| example | structure | amine | yield | Rf | MS(ESI pos, m/z) |
|---|---|---|---|---|---|
| 13C | 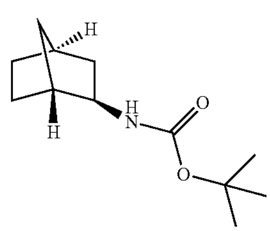 | exo-2-amino-norbornane | 4.32 g (100%) | Rf (silica gel, DCM/methanol = 95:5) = 0.90 | 212 (M + H)$^+$ |

Example 14A

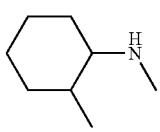

4.11 g (108 mmol) lithiumaluminium-hydride is suspended in 40 ml THF. At 0° C. a solution of 5.02 g (21.7 mmol) 13A in 40 ml THF is added dropwise. The mixture is heated to reflux for 1.5 h and then stirred at room temperature for 14 h. 80 ml THF are added and while cooling with a ice-water bath 25 ml of a saturated sodium sulphate solution is added. The mixture is stirred 20 min at room temperature. The mixture is filtered over a pad of Celite and the solution evaporated.

yield: 1.14 g (41%)
MS (ESI pos): m/z=128 (M+H)$^+$

Example 14B

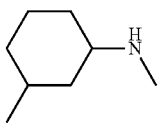

14B is prepared in analogy to 14A. Instead of 13A 13B is used.

yield: 0.75 g (42%)
LC-MS (Method 1s): RT=0.82 min
MS (ESI pos): m/z=128 (M+H)$^+$ The following products are synthesized in analogy to the preparation of example 14A, using the corresponding Boc-amine as starting materials:

| example | structure | amine | yield | RT (LC-MS; Method 1s) | MS(ESI pos, m/z) |
|---|---|---|---|---|---|
| 14C | 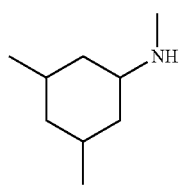 | 13C | 4.32 g (59%) | 0.66 min | 126 (M + H)$^+$ |

Example 15A

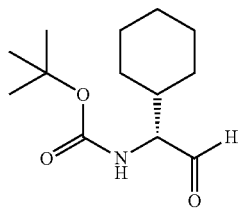 [SMILES: CC(C)(C)OC(=O)N[C@@H](C=O)C1CCCCC1]

1.00 g (7.40 mmol) N-methyl-3,5-dimethylaniline in 20 ml 1 N hydrochloric acid are hydrogenated at room temperature and 5 bar for 9 h over 300 mg platinum oxide. The mixture is filtered and the solvent evaporated to yield the product as a white solid.

yield: 1.36 g (100%)
LC-MS (Method 1s): RT=0.99 min
MS (ESI pos): m/z=142 (M+H)$^+$

Example 16A

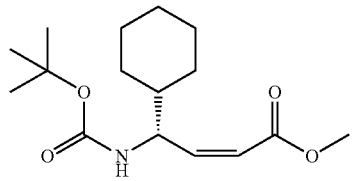 [SMILES: COC(=O)/C=C\[C@H](NC(=O)OC(C)(C)C)C1CCCCC1]

To a solution of 1.87 g (97%, 4.40 mmol) Dess-Martin periodinane in 20 ml DMF is added at 15° C. a solution of 1.00 g (4.11 mmol) N-Boc-D-cyclohexylglycinol in 20 ml DCM. The mixture is stirred for 2 h at 10 to 15° C. after which 20 ml of saturated sodium thiosulphate and 20 ml of saturated sodium hydrogencarbonate solutions are added. The mixture is stirred until the evolution of gas has ended. The organic layer is separated and the solvent is evaporated. The product is used as such in the next step.

yield: 1.13 g (100%)
LC-MS (Method 1s): RT=1.59 min
MS (ESI pos): m/z=242 (M+H)$^+$

Example 17A 15 ml THF are added under an atmosphere of nitrogen to 220 mg (5.50 mmol) of sodium hydride (60% suspension in mineral oil). The mixture is cooled to 4° C. and a solution of 0.81 ml (5.00 mmol) trimethyl-phosphonoacetate in 10 ml THF is added. The mixture is stirred 1 h at 5° C. After this a solution of 990 mg (4.10 mmol) 16A in 15 ml THF is added slowly at 0° C. The mixture is allowed to warm to room temperature and stirred for 2 h. 20 ml of water are added slowly and the THF is removed. To the residue ethyl acetate is added, the mixture is washed with water, dried and the solvent evaporated. The product is used as such in the next step.

yield: 1.50 g (100%)
LC-MS (Method 1s): RT=1.72 min
MS (ESI pos): m/z=298 (M+H)$^+$

Example 18A

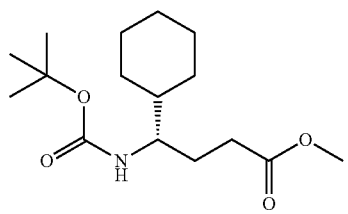 [SMILES: COC(=O)CC[C@H](NC(=O)OC(C)(C)C)C1CCCCC1]

1.22 g (4.09 mmol) 17A are hydrogenated in 50 ml methanol over 500 mg Raney-Nickel for 24 h. The mixture is filtered, evaporated and the product is used as such in the next step.
yield: 1.28 g (100%)
LC-MS (Method 1s): RT=1.70 min
MS (ESI pos): m/z=299 (M+H)$^+$

Example 19A

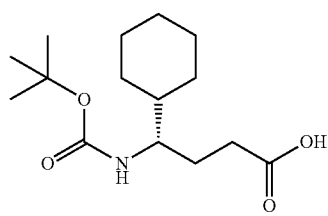 [SMILES: CC(C)(C)OC(=O)N[C@@H](CCC(=O)O)C1CCCCC1]

1.20 g (4.01 mmol) 18A are dissolved in 50 ml methanol and 2 ml of a 4 N sodium hydroxide solution is added. The mixture is stirred at 40° C. for 14 h. The pH is adjusted to 4 with 4 N hydrochloric acid. The methanol is removed. The residue is dissolved in ethyl acetate. The solution is washed with water, dried and evaporated.
yield: 1.05 g (92%)
LC-MS (Method 1s): RT=1.48 min
MS (ESI pos): m/z=284 (M−H)+

Example 20A

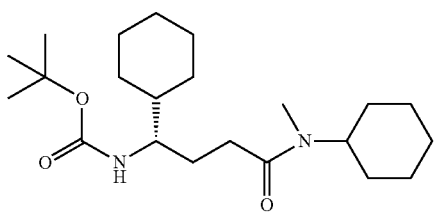 [SMILES: CN(C(=O)CC[C@H](NC(=O)OC(C)(C)C)C1CCCCC1)C1CCCCC1]

To a solution of 2.12 g (7.44 mmol) 19A in 50 ml THF are added 2.39 g (7.44 mmol) TBTU and 1.78 ml (10.4 mmol) DIPEA. The mixture is stirred for 10 min and 1.07 ml (8.18 mmol) N-methyl-cyclohexylamine is added. The mixture is stirred for 14 h and evaporated. The residue is dissolved in ethyl acetate, washed with sodium hydrogencarbonate solution and with 0.1 M hydrochloric acid and water, dried and evaporated. The residue is purified by Flash-chromatography (silica gel cyclohexane/ethyl acetate 70:30).
yield: 9.50 g (23%)
LC-MS (Method 1s): RT=1.91 min
MS (ESI pos): m/z=381 (M+H)$^+$

Example 21A

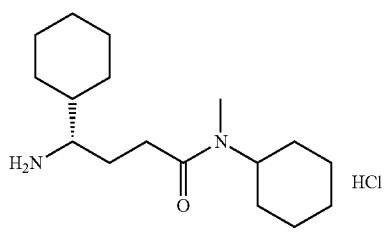 [SMILES: CN(C(=O)CC[C@H](N)C1CCCCC1)C1CCCCC1 ; Cl]

1.29 g (3.38 mmol) 20A dissolved in 7 ml 1,4-dioxane and 3.4 ml of a 4 M solution of hydrogen chloride in 1,4-dioxane is added. The mixture is stirred for 2 h. The solvent is evaporated to yield the product as a hydrochloric acid salt.
yield: 1.11 g (100%)
LC-MS (Method 1s): RT=1.28 min
MS (ESI pos): m/z=281 (M+H)$^+$

Example 22A

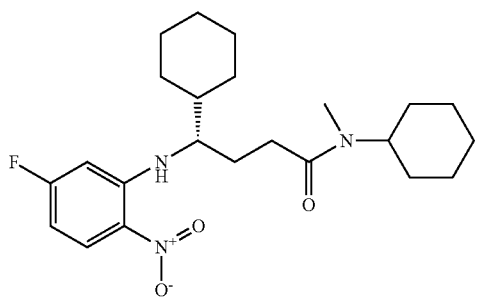 [SMILES: CN(C(=O)CC[C@H](Nc1cc(F)ccc1[N+](=O)[O-])C1CCCCC1)C1CCCCC1]

300 mg (0.95 mmol) 21A is dissolved in 15 ml 1,4-dioxane are stirred together with 181 mg (1.14 mmol) 2,4-difluoronitrobenzene and 0.33 ml triethylamine for 5 d at 40° C. The mixture is evaporated and the residue purified by Flash-chromatography (silica gel cyclohexane/ethyl acetate 78:22).
yield: 296 mg (75%)
LC-MS (Method 1s): RT=2.11 min
MS (ESI pos): m/z=420 (M+H)$^+$

Example 23A

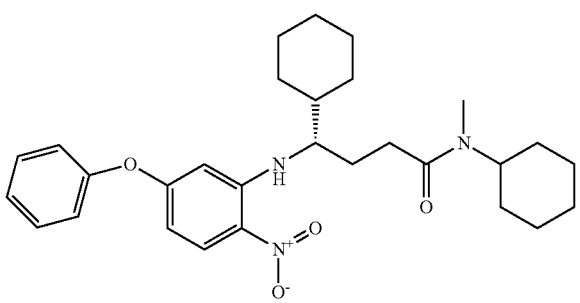 [SMILES: CN(C(=O)CC[C@H](Nc1cc(Oc2ccccc2)ccc1[N+](=O)[O-])C1CCCCC1)C1CCCCC1]

A mixture of 296 mg (0.71 mmol) 22A, 73 mg (0.78 mmol) phenol and 127 mg (0.92 mmol) potassium-carbonate in 5 ml DMF is stirred at 90° C. for 2 h. The mixture is evaporated and the residue is dissolved in ethyl acetate. The mixture is washed with sodium hydrogencarbonate solution and with water, the organic layer separated, dried and evaporated. The product is used as such in the next step.

yield: 375 mg (100%)
LC-MS (Method 1s): RT=2.24 min
MS (ESI pos): m/z=494 (M+H)⁺

Example 24A

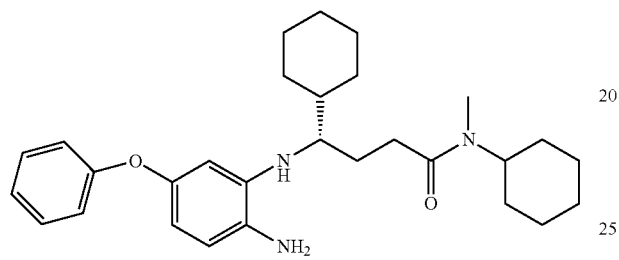

514 mg (1.04 mmol) 23A are hydrogenated in 20 ml methanol over 250 mg palladium on activated carbon (10%) at 3 bar. The mixture is filtered and the solvent evaporated. The product is used as such in the next step.

yield: 446 mg (92%)
LC-MS (Method 1s): RT=1.82 min
MS (ESI pos): m/z=464 (M+H)⁺

Example 25A

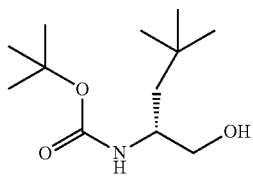 [SMILES: CC(C)(C)C[C@H](CO)NC(=O)OC(C)(C)C]

Under nitrogen 3.00 g (12.3 mmol) Boc-beta-tert.-butyl-D-alanine is dissolved in 15 ml dimethoxyethane and cooled to −22° C. 1.35 ml (12.3 mmol) N-methylmorpholine are added. To this a solution of 1.67 ml (12.8 mmol) isobutyl-chloroformat in 10 ml dimethoxyethane is added. The reaction mixture is allowed to warm to room temperature and then stirred for an additional 60 min. The precipitate is quickly filtered off and the solution cooled to −15° C. 786 mg (20.8 mmol) sodium-borohydride and a few drops of water are added. The mixture is allowed to warm to room temperature and is stirred for 14 h. 30 ml of water are added and the dimethoxyethane is removed. The mixture is extracted with ethyl acetate, dried and the solvent evaporated to yield the product as a clear oil.

yield: 2.70 g (95%)
LC-MS (Method 1s): RT=1.37 min
MS (ESI pos): m/z=232 (M+H)⁺

Example 26A

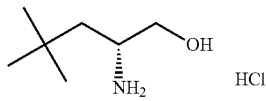

2.70 g (11.7 mmol) 25A is dissolved in 20 ml DCM and 5 ml of a 4 M solution of hydrogen chloride in 1,4-dioxane are added. The mixture is stirred for 14 h and the solvent removed. The product is used as such in the next step.

yield: 2.90 g (100%)
MS (ESI pos): m/z=132 (M+H)⁺

Example 27A

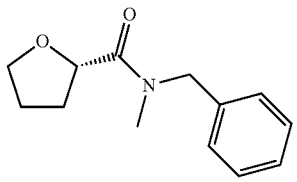 [SMILES: CN(Cc1ccccc1)C(=O)[C@@H]1CCCO1]

To a solution of 20 ml (209 mmol) (S)-tetrahydrofuran-2-carboxylic acid and 25.3 g (209 mmol) N-methyl-benzylamine in 200 ml THF is added 67.1 g (209 mmol) TBTU while cooling with an ice-water bath. The cooling is removed and the mixture is stirred for 14 h. The mixture is filtered, the filtrate made basic with sodium hydrogencarbonate solution and extracted with ethyl acetate. The combined organic layers are washed with water, dried and the solvent is evaporated to yield the product as a yellow oil.

yield: 24.8 g (54%)
tlc: Rf (silica gel, ethyl acetate)=0.62
MS (ESI pos): m/z=242 (M+Na)⁺

Example 28A

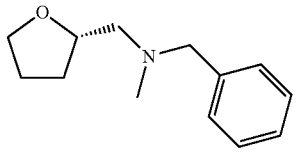

17.0 g (448 mmol) lithiumaluminium-hydride are suspended in 150 ml THF. To this a solution of 24.6 g (112 mmol) 27A in 90 ml THF is added. The mixture is heated to reflux for 3 h. The mixture is cooled to 10° C. and 10 ml water, 10 ml of 4 N sodiumhydroxide solution, and again 10 ml water are added carefully. The mixture is stirred for 20 min and then filtered over magnesium sulphate. The filter cake is washed with THF. The filtrate is concentrated under vacuum to yield the product as a light yellow oil.

yield: 21.7 g (95%)
tlc: Rf (silica gel, ethyl acetate/methanol 9:1)=0.2
MS (ESI pos): m/z=206 (M+H)⁺

Example 29A

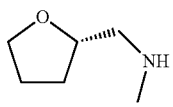

21.7 g (106 mmol) 28A are hydrogenated in 200 ml ethanol over 4 g palladium on activated carbon (10%) for 2 h. The mixture is filtered and the solvent evaporated. The product is used as such in the next step.

yield: 9.4 g (77%)

tlc: Rf (silica gel, ethyl acetate/methanol 9:1)=0.1

Example 30A

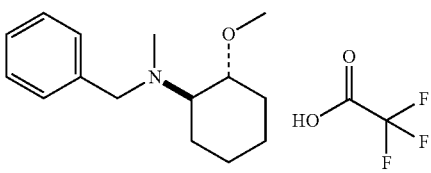

1.00 g (4.87 mmol) trans-2-benzylamino-1-cyclohexanol in 15 ml DMF are cooled to 0° C. and 470 mg (11.8 mmol) of sodium hydride (60% suspension in mineral oil) are added. The mixture is allowed to warm to room temperature and is stirred for 60 min. It is then cooled again to 0° C. and 735 µl (11.7 mmol) iodomethane are added. The mixture is stirred for 14 h at room temperature. The mixture is filtered, concentrated and water and ethyl acetate are added. The organic layer is separated, the aqueous layer is extracted with ethyl acetate and the organic layers are combined, dried and evaporated. The product is purified by preparative HPLC (method 1). Fractions containing the product are combined and lyophilized to yield the product as a TFA salt.

yield: 1.12 g (66%)

LC-MS (Method 1s): RT=1.05 min

MS (ESI pos): m/z=234 (M+H)$^+$

Example 31A

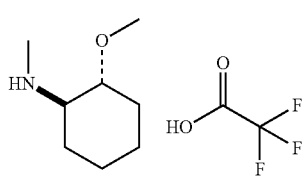

1.12 g (3.22 mmol) 30A are hydrogenated in 15 ml methanol over 200 mg palladium on activated carbon (10%) for 16 h at room temperature and a pressure of 50 psi. The mixture is filtered and the solvent evaporated. The product is used as such in the next step.

yield: 0.76 g (91%)

tlc: Rf (silica gel, DCM/methanol 95:5)=0.36

MS (ESI pos): m/z=144 (M+H)$^+$

Example 32A

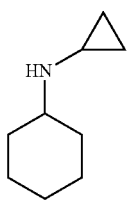

2.42 ml (23.1 mmol) Cyclohexanone and 1.49 ml (21.0 mmol) cyclopropylamine are dissolved in 10 ml anhydrous ethanol. After 18 h at room temperature, 0.20 g palladium on activated carbon (10%) is added and the suspension is hydrogenated for 10 h at room temperature and a pressure of 50 psi. The mixture is filtered and the solvent evaporated. The product is used as such in the next step.

yield: 2.9 g (100%)

LC-MS (Method 1s): RT=0.72 min

MS (ESI pos): m/z=140 (M+H)$^+$

Example 33A

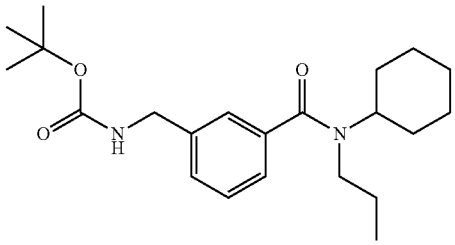 [SMILES: CCCN(C(=O)c1cccc(CNC(=O)OC(C)(C)C)c1)C1CCCCC1]

To a solution of 5.20 g (20.1 mmol) 3-(tert-butoxycarbonylamino-methyl)-benzoic acid in 10 ml DMF are added 6.45 g (20.1 mmol) TBTU and 6.9 ml (40.2 mmol) DIPEA. The mixture is stirred for 20 min and 2.84 g (20.1 mmol) N-propyl-cyclohexylamine (ChemBridge Corporation, 16981 Via Tazon, Suite G, San Diego, Calif. 92127, USA) is added. The mixture is stirred for 1 h and evaporated. The residue is dissolved in DCM, washed with saturated aqueous sodium hydrogencarbonate and water, dried and evaporated. The mixture is dissolved in acetonitrile/water/TFA (50:50:0.1) and then purified by preparative HPLC (method 1).

yield: 5.70 g (76%)

LC-MS (Method 1s): RT=1.80 min

MS (ESI pos): m/z=375 (M+H)$^+$

The following products are synthesized in analogy to the preparation of example 33A, using the corresponding acids as starting materials:

| | structure | acid | yield | RT (LC-MS; Method 1s): | MS (ESI pos, m/z) |
|---|---|---|---|---|---|
| 33B | ![structure] | 2-chloro-5-iodo-benzoic acid | 5.20 g (72%) | 2.04 | 406/408 (M + H)+ (Cl) |
| 33C | ![structure] | 3-cyano-2-fluoro-benzoic acid (Insight Chemical Solutions Ltd., MerseyBIO Crown Street, Liverpool Merseyside L69 7ZB, UNITED KINGDOM) | 2.50 g (72%) | 1.70 | 289 (M + H)+ |
| 33D | ![structure] | 3-cyano-5-fluoro-benzoic acid (Fluorochem Ltd., Wesley Street, Old Glossop, Derbyshire SK13 7RY, UNITED KINGDOM) | 6.46 g (74%) | 1.74 | 289 (M + H)+ |

Example 34A

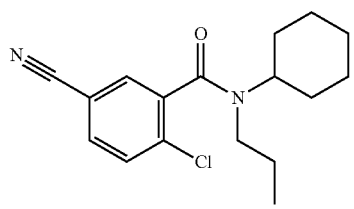 [SMILES: CCCN(C(=O)c1cc(C#N)ccc1Cl)C1CCCCC1]

Example 35A

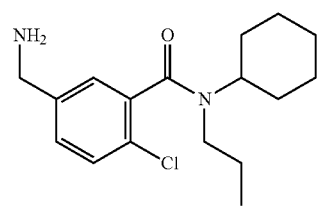 [SMILES: CCCN(C(=O)c1cc(CN)ccc1Cl)C1CCCCC1]

To a solution of 3.93 g (9.69 mmol) 33B in 40 ml N-Methylpyrrolidon are added 949 mg (19.4 mmol) sodium cyanide and 2.12 g (9.69 mmol) nickel(II)bromide. The mixture is heated in a sealed tube for 16 min to 200° C. using microwave irradiation. Water is added and the mixture is extracted with ethyl acetate. The organic layer is dried, filtered and evaporated under reduced pressure. The remaining material is dissolved in acetonitrile/water/TFA (50:50:0.1) and then purified by preparative HPLC (method 1).

yield: 1.17 g (40%)
LC-MS (Method 1s): RT=1.78 min
MS (ESI pos): m/z=305/307 (M+H)+ (Cl)

0.89 g (2.92 mmol) 34A are hydrogenated at 50 psi for 12 h with 75 ml of a saturated solution of ammonia in methanol over 200 mg Raney-Nickel. The mixture is filtered and the solvent evaporated under reduced pressure. The product is used for the next reaction without further purification.

yield: 0.90 g (100%)
LC-MS (Method 1s): RT=3.31 min
MS (ESI pos): m/z=309/311 (M+H)+ (Cl)

The following products are synthesized in analogy to the preparation of example 35A, using the corresponding nitriles as starting materials:

| | structure | nitrile | yield | RT (LC-MS; Method 1s): | MS (ESI pos, m/z) |
|---|---|---|---|---|---|
| 35B | (2-fluoro isomer) | 33C | 2.55 g (100%) | 1.20 | 293 (M + H)⁺ |
| 35C | (3-fluoro isomer) | 33D | 6.10 g (99%) | 1.24 | 293 (M + H)⁺ |

Example 36A

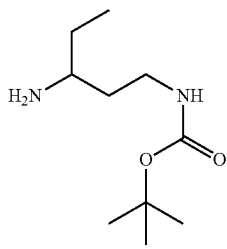

To a solution of 8.00 g (76.7 mmol) pentane-1,3-diamine in 150 ml anhydrous ethanol 29.0 ml (153 mmol) tert.-butyl-phenyl-carbonate are added. The mixture is heated to reflux for 4 h. After cooling to room temperature 500 ml water is added, the mixture is adjusted to pH 3 with 2M HCl and extracted two times with 500 ml DCM. The aqueous layer is separated, adjusted to pH 12 with 2M sodium hydroxide solution and extracted three times with 500 ml DCM. The organic phases are combined, dried and evaporated under reduced pressure to yield the product as an oil. The product is used for the next reaction without further purification.

yield: 15.5 g (100%)
LC-MS (Method 1s): RT=0.91 min
MS (ESI pos): m/z=203 (M+H)⁺

Example 37A 6.00 g (21.9 mmol) 42B are stirred together with 3.48 g (21.9 mmol) 2,4-difluoro-nitrobenzene and 6.04 g (43.7 mmol) potassium-carbonate in 15 ml DMF for 12 h at room temperature. The mixture is evaporated under reduced pressure. Dichloromethane and 2M hydrochloric acid are added. The organic layer is separated, dried, filtered and evaporated under reduced pressure. The product is used for the next reaction without further purification.

yield: 9.04 g (100%)
LC-MS (Method 1s): RT=1.92 min
MS (ESI pos): m/z=414 (M+H)⁺

The following product is synthesized in analogy to the preparation of example 37A, using the corresponding arylfluoride as starting material:

| | structure | arylfluoride | yield | RT (LC-MS; Method 1s): | MS (ESI pos, m/z) |
|---|---|---|---|---|---|
| 37B | 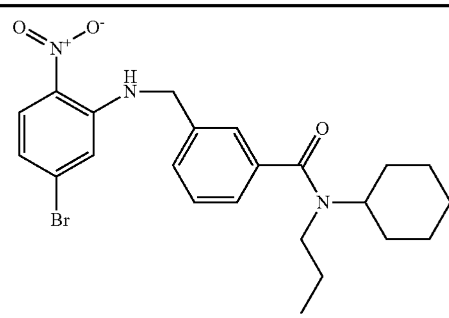 | 4-bromo-2-fluoro-1-nitro-benzene | 2.30 g (100%) | 2.04 | 474/476 (M+H)⁺ (Br) |

Example 38A

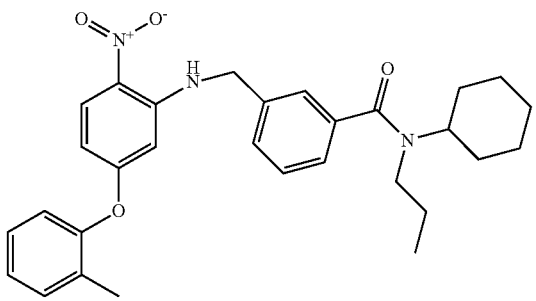 [SMILES: CCCN(C(=O)c1cccc(CNc2cc(Oc3ccccc3C)ccc2[N+](=O)[O-])c1)C1CCCCC1]

A mixture of 507 mg (1.23 mmol) 37A, 133 mg (1.23 mmol) 2-methyl-phenol and 508 mg (3.68 mmol) potassium-carbonate in 5 ml DMF is stirred at 100° C. for 14 h. The mixture is evaporated under reduced pressure and the residue is dissolved in DCM. The DCM-phase is washed with water, the organic layer separated, dried and evaporated. The mixture is dissolved in acetonitrile/water/TFA (50:50:0.1) and then purified by preparative HPLC (method 2).

yield: 160 mg (26%)

LC-MS (Method 1s): RT=2.10 min

MS (ESI pos): m/z=502 (M+H)$^+$

The following products are synthesized in analogy to the preparation of example 38A, using 37A and the corresponding phenols as starting materials:

| example | structure | phenol | yield | RT (LC-MS; Method 1s) | MS(ESI pos, m/z) |
|---|---|---|---|---|---|
| 38B | 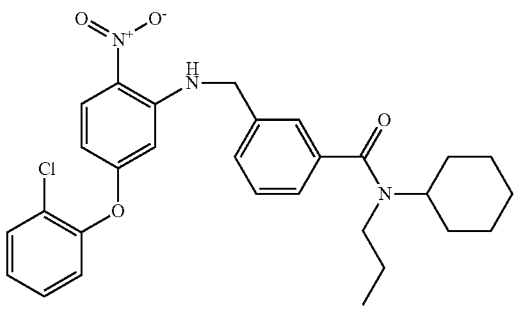 [SMILES: CCCN(C(=O)c1cccc(CNc2cc(Oc3ccccc3Cl)ccc2[N+](=O)[O-])c1)C1CCCCC1] | 2-chloro-phenol | 410 mg (36%) | 2.11 min | 522/524 (M + H)$^+$ (Cl) |
| 38C | 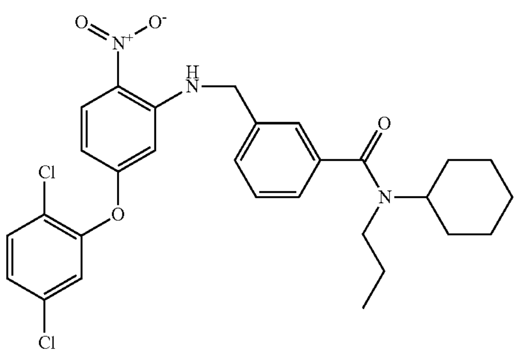 [SMILES: CCCN(C(=O)c1cccc(CNc2cc(Oc3cc(Cl)ccc3Cl)ccc2[N+](=O)[O-])c1)C1CCCCC1] | 2,5-dichloro-phenol | 200 mg (17%) | 2.20 | 556/558/560 (M + H)$^+$ (2Cl) |
| 38D | 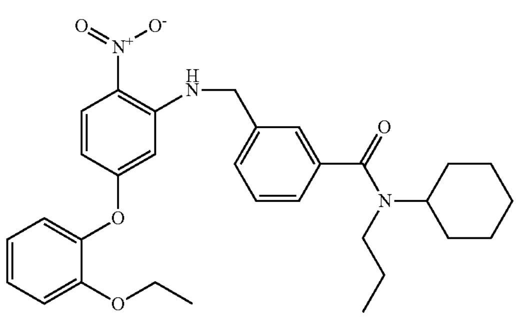 [SMILES: CCCN(C(=O)c1cccc(CNc2cc(Oc3ccccc3OCC)ccc2[N+](=O)[O-])c1)C1CCCCC1] | 2-ethoxy-phenol | 100 mg (15%) | 2.06 min | 532 (M + H)$^+$ |

| example | structure | phenol | yield | RT (LC-MS; Method 1s) | MS(ESI pos, m/z) |
|---|---|---|---|---|---|
| 38E | 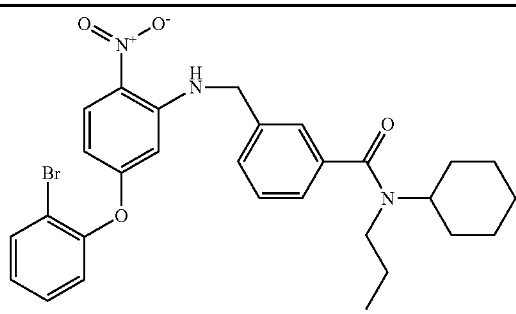 | 2-bromo-phenol | 250 mg (36%) | 2.17 | 566/568 (M + H)+ (Br) |
| 38F | 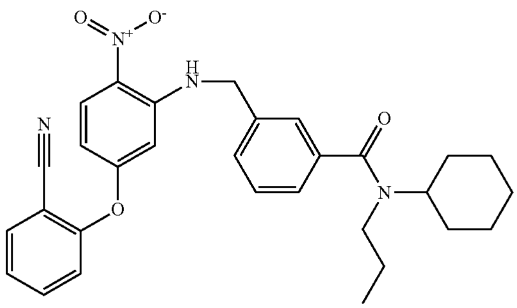 [SMILES: CCCN(C(=O)c1cccc(CNc2cc(Oc3ccccc3C#N)ccc2[N+](=O)[O-])c1)C1CCCCC1] | 2-hydroxy-benzo-nitrile | 250 mg (40%) | 1.99 | 513 (M + H)+ |

Example 39A

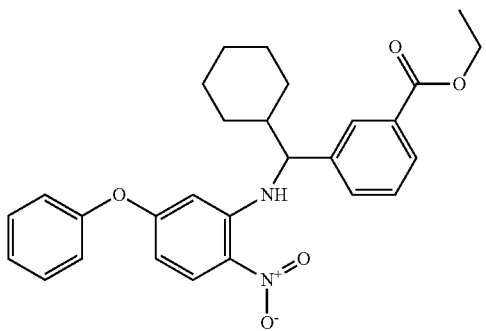 [SMILES: CCOC(=O)c1cccc(C(Nc2cc(Oc3ccccc3)ccc2[N+](=O)[O-])C2CCCCC2)c1]

4.65 g (12.4 mmol) 3C are dissolved in DCM and extracted with 5% aqueous potassium-carbonate solution. The organic layer is separated, dried, filtered and evaporated under reduced pressure to give the free base of 3C. This material is stirred together with 2.00 g (12.6 mmol) 2,4-difluoro-nitrobenzene and 3.50 g (25.3 mmol) potassium-carbonate in 15 ml DMF for 12 h at room temperature. 1.71 g (12.4 mmol) potassium-carbonate and 1.45 g (12.5 mmol) sodium phenolate is added and the mixture is stirred at 100° C. for 14 h. The mixture is evaporated and DCM is added. The DCM-phase is washed with water, the organic layer separated, dried and evaporated. The mixture is dissolved in acetonitrile/water/TFA (50:50:0.1) and then purified by preparative HPLC (method 1).

yield: 5.52 g (93%)

LC-MS (Method 1s): RT=2.30 min

MS (ESI pos): m/z=475 (M+H)+

The following product is synthesized in analogy to the preparation of example 39A, using the corresponding ammonium salt as starting material:

| | structure | ammonium salt | yield | RT (LC-MS; Method 1s): | MS (ESI pos, m/z) |
|---|---|---|---|---|---|
| 39B | 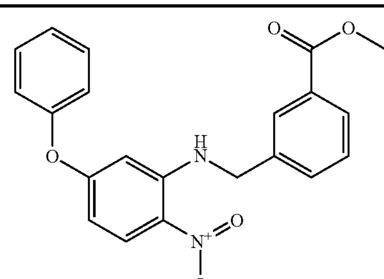 | 3-aminomethyl-benzoic acid methyl ester hydrochloride (Apollo Scientific Ltd., Whitefield Road, Bredbury, Stockport, Cheshire SK6 2QR, UNITED KINGDOM) | 7.50 g (72%) | 1.82 | 379 (M + H)+ |

Example 39C

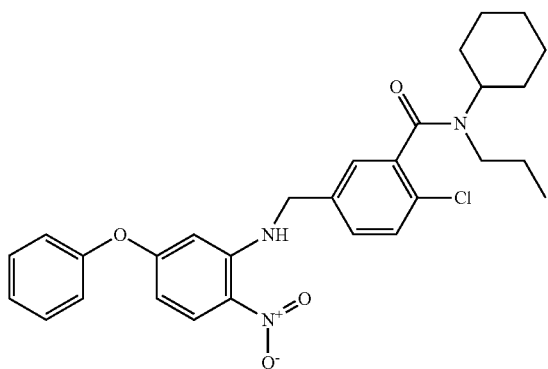 [SMILES: CCCN(C(=O)c1cc(CNc2cc(Oc3ccccc3)ccc2[N+](=O)[O-])ccc1Cl)C1CCCCC1]

1.18 g (3.82 mmol) 35A is stirred together with 0.62 g (3.90 mmol) 2,4-difluoro-nitrobenzene and 1.10 g (7.96 mmol) potassium-carbonate in 40 ml DMF for 12 h at room temperature. 0.53 g (3.82 mmol) potassium-carbonate and 0.44 g (3.82 mmol) sodium phenolate is added and the mixture is stirred at 100° C. for 14 h. The mixture is evaporated and DCM is added. The DCM-phase is washed with water, the organic layer separated, dried and evaporated. The mixture is dissolved in acetonitrile/water/TFA (50:50:0.1) and then purified by preparative HPLC (method 2).

yield: 0.48 g (24%)
LC-MS (Method 1s): RT=2.18 min
MS (ESI pos): m/z=522 (M+H)$^+$ The following products are synthesized in analogy to the preparation of example 39C, using the corresponding amines as starting materials:

| | structure | amine | yield | RT (LC-MS; Method 1s): | MS (ESI pos, m/z) |
|---|---|---|---|---|---|
| 39D | 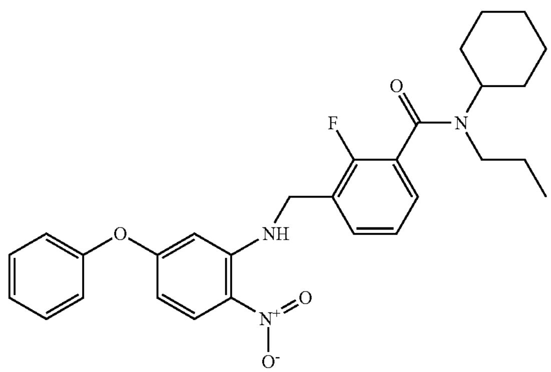 [SMILES: CCCN(C(=O)c1cccc(CNc2cc(Oc3ccccc3)ccc2[N+](=O)[O-])c1F)C1CCCCC1] | 35B | 200 mg (47%) | 2.13 | 506 (M + H)$^+$ |
| 39E | 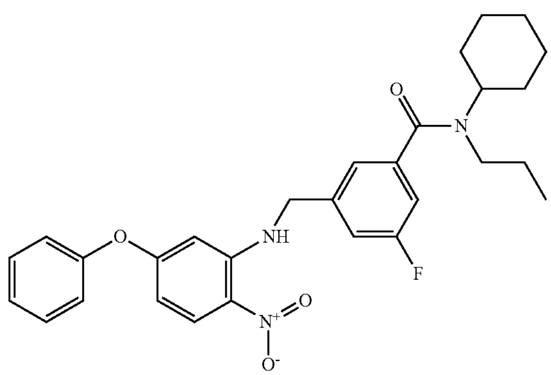 [SMILES: CCCN(C(=O)c1cc(F)cc(CNc2cc(Oc3ccccc3)ccc2[N+](=O)[O-])c1)C1CCCCC1] | 35C | 1.18 g (11%) | 2.11 | 506 (M + H)$^+$ |
| 39F | 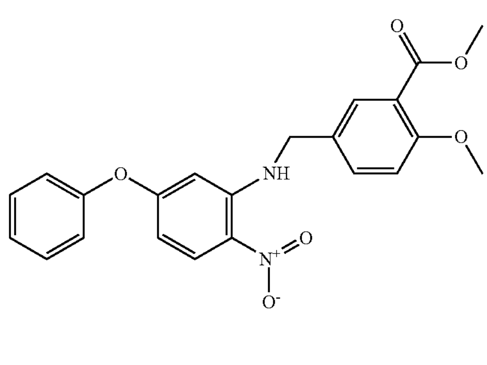 [SMILES: COC(=O)c1cc(CNc2cc(Oc3ccccc3)ccc2[N+](=O)[O-])ccc1OC] | 5-amino-methyl-2-methoxy-benzoic acid methyl ester* | 8.64 g (100%) | 1.83 | 409 (M + H)$^+$ |

| structure | amine | yield | RT (LC-MS; Method 1s): | MS (ESI pos, m/z) |
|---|---|---|---|---|
| 39G | 36A | 14.0 g (93%) | 2.00 | 416 (M + H)⁺ |

*Ryan Scientific, Inc., P O Box 703, Mt. Pleasant, SC, 29465, USA

Example 40A

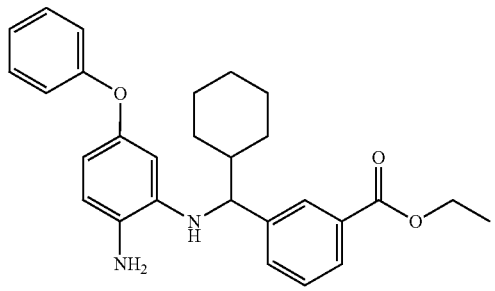 [SMILES: CCOC(=O)c1cccc(C(Nc2cc(Oc3ccccc3)ccc2N)C2CCCCC2)c1]

5.50 g (11.5 mmol) 39A are hydrogenated at 50 psi in 150 ml THF over 550 mg Raney-Nickel for 2 h. The mixture is filtered and the solvent evaporated. The product is used as such in the next step.

yield: 5.00 g (97%)

LC-MS (Method 1s): RT=1.76 min

MS (ESI pos): m/z=445 (M+H)⁺

The following products are synthesized in analogy to the preparation of example 40A, using the corresponding nitrobenzenes as starting materials:

| example | structure | nitro-benzene | yield | RT (LC-MS; Method 1s) | MS(ESI pos, m/z) |
|---|---|---|---|---|---|
| 40B | 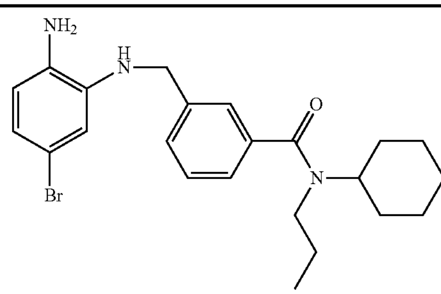 | 37B | 1.87 g (100%) | 1.61 min | 444/446 (M + H)⁺ (Br) |
| 40C | 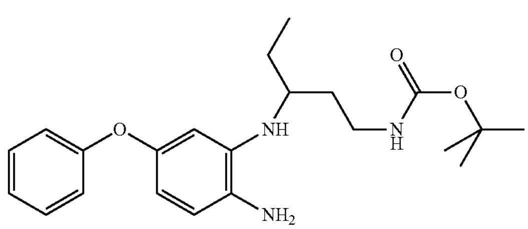 [SMILES: CCC(CCNC(=O)OC(C)(C)C)Nc1cc(Oc2ccccc2)ccc1N] | 39G | 7.42 g (100%) | 1.51 min | 386 (M + H)⁺ |
| 40D | 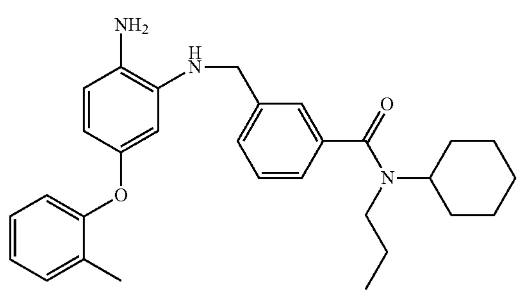 [SMILES: CCCN(C(=O)c1cccc(CNc2cc(Oc3ccccc3C)ccc2N)c1)C1CCCCC1] | 38A | 160 mg (100%) | 1.73 min | 472 (M + H)⁺ |

-continued

| example | structure | nitro-benzene | yield | RT (LC-MS; Method 1s) | MS(ESI pos, m/z) |
|---|---|---|---|---|---|
| 40E | 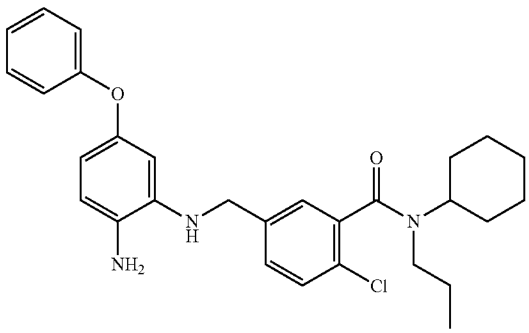 [SMILES: CCCN(C(=O)c1cc(CNc2cc(Oc3ccccc3)ccc2N)ccc1Cl)C1CCCCC1] | 39C | 380 mg (84%) | 1.76 min | 492/494 (M + H)+ (Cl) |
| 40F | 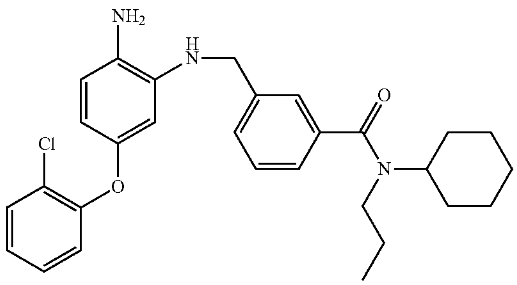 [SMILES: CCCN(C(=O)c1cccc(CNc2cc(Oc3ccccc3Cl)ccc2N)c1)C1CCCCC1] | 38B | 380 mg (100%) | 1.70 min | 492/494 (M + H)+ (Cl) |
| 40G | 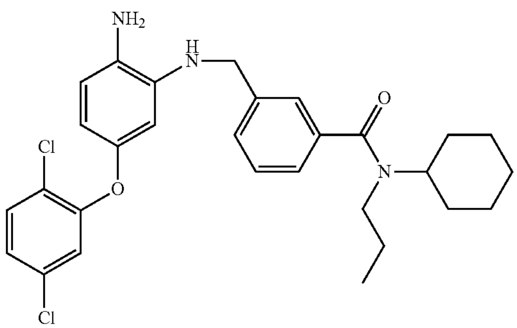 [SMILES: CCCN(C(=O)c1cccc(CNc2cc(Oc3cc(Cl)ccc3Cl)ccc2N)c1)C1CCCCC1] | 38C | 190 mg (100%) | 1.82 min | 526/528/530 (M + H)+ (2Cl) |
| 40H | 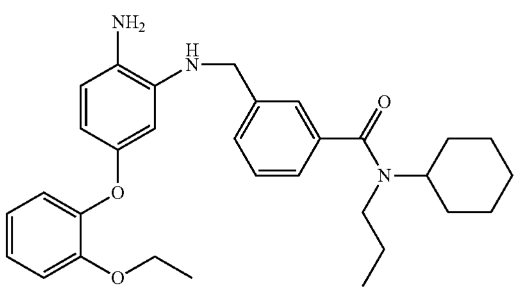 [SMILES: CCCN(C(=O)c1cccc(CNc2cc(Oc3ccccc3OCC)ccc2N)c1)C1CCCCC1] | 38D | 90 mg (95%) | 1.72 min | 502 (M + H)+ |
| 40I | 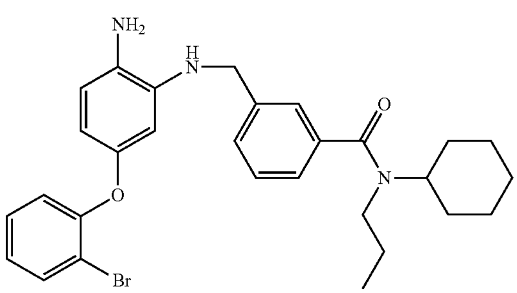 [SMILES: CCCN(C(=O)c1cccc(CNc2cc(Oc3ccccc3Br)ccc2N)c1)C1CCCCC1] | 38E | 240 mg (100%) | 1.75 min | 536/538 (M + H)+ (Br) |

| example | structure | nitro-benzene | yield | RT (LC-MS; Method 1s) | MS(ESI pos, m/z) |
|---|---|---|---|---|---|
| 40J | 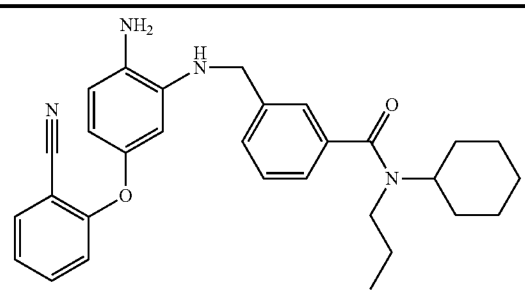 | 38F | 240 mg (100%) | 1.61 min | 483 (M + H)+ |
| 40K | 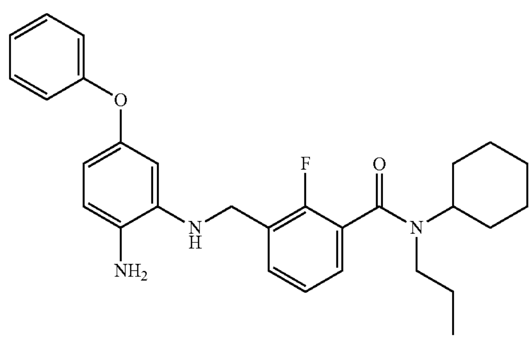 [SMILES: CCCN(C(=O)c1cccc(CNc2cc(Oc3ccccc3)ccc2N)c1F)C1CCCCC1] | 39D | 180 mg (96%) | 1.67 min | 476 (M + H)+ |
| 40L | 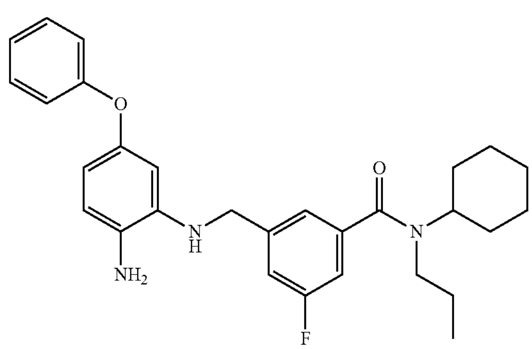 [SMILES: CCCN(C(=O)c1cc(F)cc(CNc2cc(Oc3ccccc3)ccc2N)c1)C1CCCCC1] | 39E | 1.10 g (99%) | 1.67 min | 476 (M + H)+ |
| 40M | 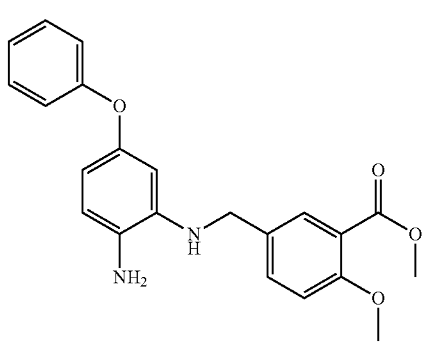 [SMILES: COC(=O)c1cc(CNc2cc(Oc3ccccc3)ccc2N)ccc1OC] | 39F | 6.10 g (94%) | 1.30 min | 379 (M + H)+ |
| 40N | 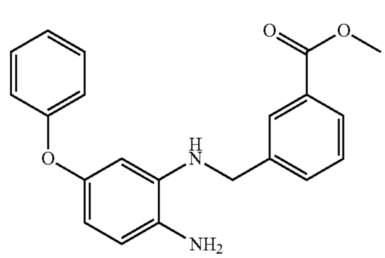 [SMILES: COC(=O)c1cccc(CNc2cc(Oc3ccccc3)ccc2N)c1] | 39B | 4.50 g (100%) | 1.40 min | 349 (M + H)+ |

Example 41A

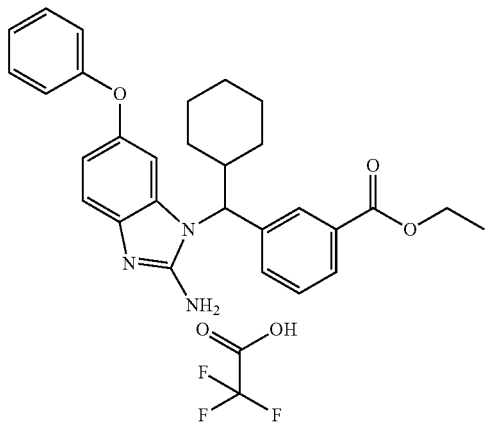

Bromocyane (1.19 g, 11.3 mmol) is added to a solution of 5.00 g (11.3 mmol) phenylene-diamine 40A in 80 ml ethanol/water (7:1) and stirred for 12 h at room temperature. The mixture is evaporated and the residue dissolved in acetonitrile/water/TFA (50:50:0.1) and purified by preparative HPLC (method 1). Fractions containing the product are combined and lyophilized to yield the product as a TFA salt.

yield: 5.16 g (97%)
LC-MS (Method 1s): RT=1.75 min
MS (ESI pos): m/z=470 (M+H)$^+$ The following examples are synthesized in analogy to the preparation of example 41A, using the corresponding phenylene-diamines as starting materials:

| example | structure | phenylene-diamine | yield | RT (LC-MS; Method 1s): | MS (ESI pos, m/z) |
|---|---|---|---|---|---|
| 41B | 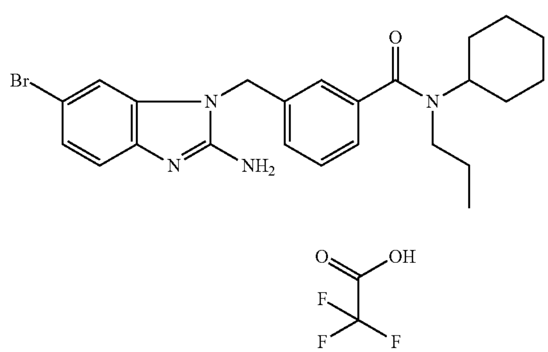 [SMILES: CCCN(C(=O)c1cccc(Cn2c(N)nc3ccc(Br)cc32)c1)C1CCCCC1 ; O=C(O)C(F)(F)F] | 40B | 1.30 g (50%) | 1.57 | 469/471 (M + H)$^+$ (Br) |
| 41C | 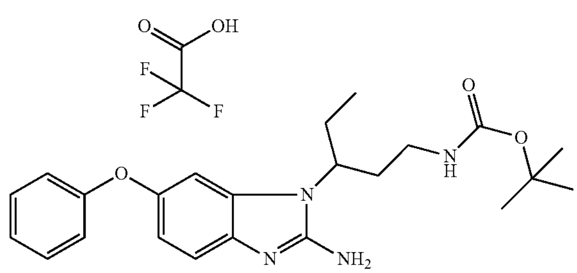 [SMILES: CCC(CCNC(=O)OC(C)(C)C)n1c(N)nc2ccc(Oc3ccccc3)cc21 ; O=C(O)C(F)(F)F] | 40C | 10.2 g (100%) | 1.53 | 411 (M + H)$^+$ |
| 41D | 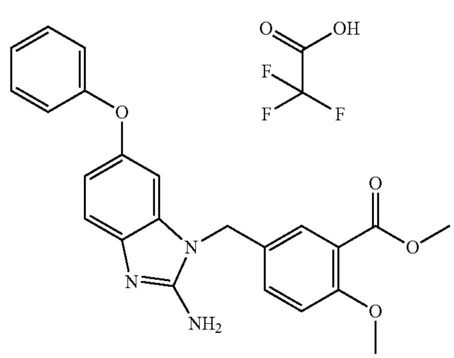 [SMILES: COC(=O)c1cc(Cn2c(N)nc3ccc(Oc4ccccc4)cc32)ccc1OC ; O=C(O)C(F)(F)F] | 40M | 6.3 g (97%) | 1.34 | 404 (M + H)$^+$ |

| example | structure | phenylene-diamine | yield | RT (LC-MS; Method 1s): | MS (ESI pos, m/z) |
|---|---|---|---|---|---|
| 41E | 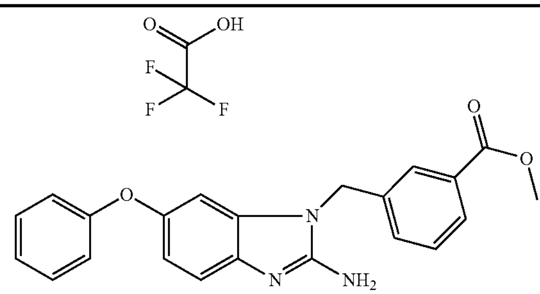 | 40N | 6.0 g (100%) | 1.43 | 374 (M + H)+ |

Example 42A

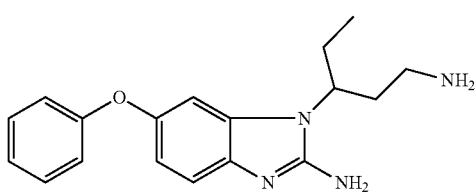

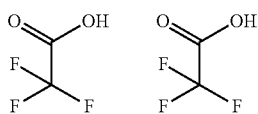

To a solution of 7.90 g, (19.2 mmol) 41C in 100 ml DCM is added 50 ml of trifluoroacetic acid. After 1 h at room temperature, the solvents are removed under reduced pressure. The residue is dissolved in acetonitrile/water/TFA (50:50:0.1) and purified by preparative HPLC (method 1). Fractions containing the product are combined and lyophilized to yield the product as a TFA salt.

yield: 6.40 g (62%)

LC-MS (Method 1s): RT=1.14 min

MS (ESI pos): m/z=311 (M+H)+

Example 42B

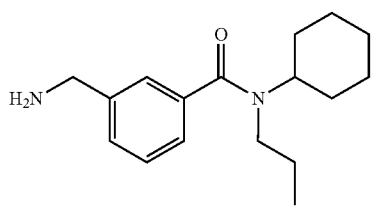 [SMILES: CCCN(C(=O)c1cccc(CN)c1)C1CCCCC1]

To a solution of 14.0 g, (37.4 mmol) 33A in 70 ml DCM is added 36 ml of trifluoroacetic acid. After 1 h at room temperature, the solvents are removed under reduced pressure. The residue is dissolved in DCM, washed with aqueous ammonia (15%), dried and evaporated. The product is used for the next reaction without further purification.

yield: 7.92 g (77%)

LC-MS (Method 1s): RT=1.24 min

MS (ESI pos): m/z=275 (M+H)+

Example 43A

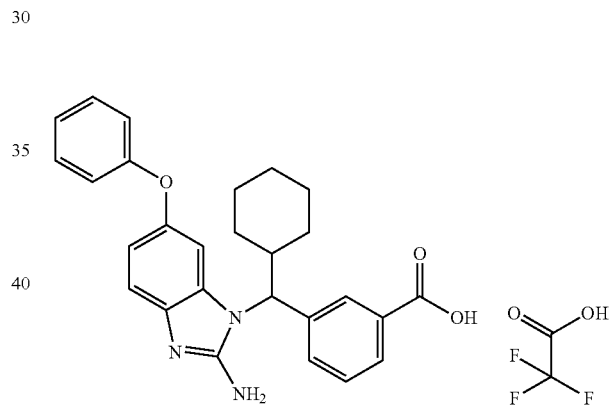

5.00 g (10.7 mmol) 41A are suspended in 10 ml of a 4 N sodium hydroxide solution and stirred for 12 h. The pH is adjusted to 4 with 4 N hydrochloric acid. The solvents are removed under reduced pressure. The residue is dissolved in acetonitrile/water/TFA (50:50:0.1) and purified by preparative HPLC (method 1). Fractions containing the product are combined and lyophilized to yield the product as a TFA salt.

yield: 2.77 g (47%)

LC-MS (Method 1s): RT=1.53 min

MS (ESI pos): m/z=442 (M−H)+

The following examples are synthesized in analogy to the preparation of example 43A, using the corresponding esters as starting materials:

| example | structure | ester | yield | RT (LC-MS; Method 1s): | MS(ESI pos, m/z) |
|---|---|---|---|---|---|
| 43B | 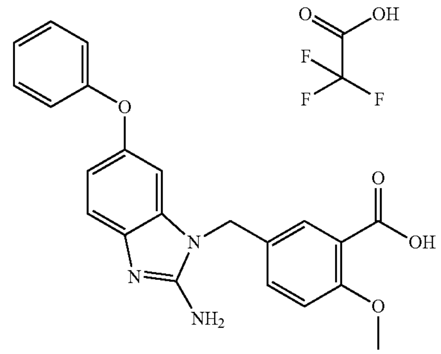 [SMILES: COc1ccc(Cn2c(N)nc3ccc(Oc4ccccc4)cc32)cc1C(=O)O ; O=C(O)C(F)(F)F] | 41D | 0.61 g (54%) | 1.25 | 390 (M + H)⁺ |
| 43C | 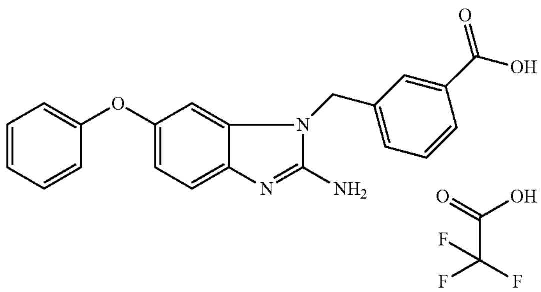 | 41E | 3.30 g (69%) | 1.30 | 360 (M + H)⁺ |

Example 44A

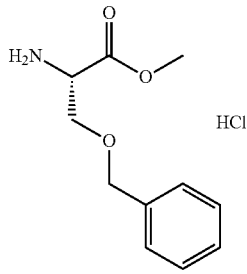

To a solution of 300 mg (1.02 mmol) (S)-3-benzyloxy-2-tert-butoxycarbonylamino-propionic acid in 10 ml DCM is added 1.5 ml (20.5 mmol) thionylchloride at 0° C. After stirring for 14 h the mixture is concentrated and evaporated several times after the addition of methanol to yield the hydrochloride of the product as a solid.

yield: 270 mg (100%)
LC-MS (Method 1s): RT=0.92 min
MS (ESI pos): m/z=210 (M+H)⁺

Example 45A

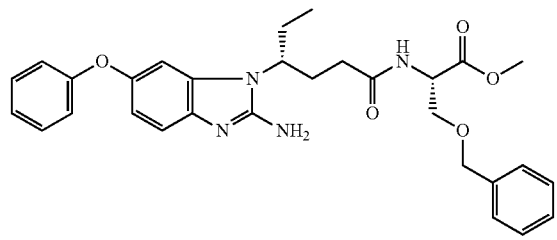

-continued

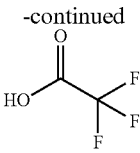

45A is synthesized in analogy to the preparation of example 20 from 12C, using 44A as amine.
yield: 60.3 mg (70%)
LC-MS (Method 1s): RT=1.46 min
MS (ESI pos): m/z=532 (M+H)⁺

Example 1

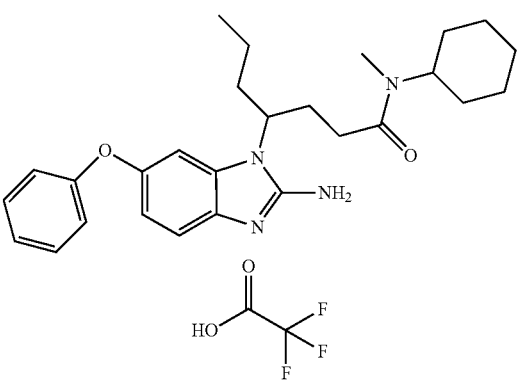

A 1 M solution of bromocyane in ethanol containing 102 mg (0.97 mmol) of bromocyane is added to a solution of 410 mg 0.97 mmol 6A in 5 ml ethanol. The mixture is stirred for 14 h at room temperature. The mixture is evaporated and the residue dissolved in acetonitrile/water/TFA (50:50:0.1) and purified by preparative HPLC (method 2). Fractions containing the product are combined and lyophilized to yield the product as a TFA salt.

yield: 297 mg (55%)
LC-MS (Method 1s): RT=1.63 min
MS (ESI pos): m/z=449 (M+H)⁺

Example 2

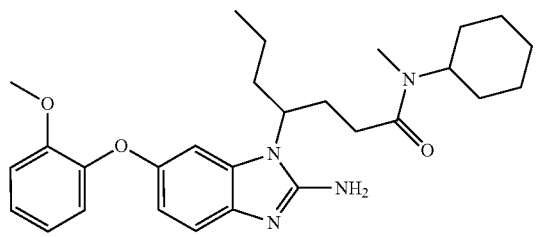

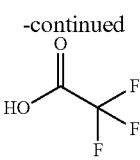

A 1 M solution of bromocyane in ethanol containing 38.5 mg (0.36 mmol) of bromocyane is added to a solution of 165 mg (0.36 mmol) 6B in 5 ml ethanol. The mixture is stirred for 14 h at room temperature. The mixture is evaporated and the residue dissolved in acetonitrile/water/TFA (50:50:0.1) and purified by preparative HPLC (method 2). Fractions containing the product are combined and lyophilized to yield the product as a TFA salt.

yield: 108 mg (50%)
LC-MS (Method 1s): RT=1.49 min
MS (ESI pos): m/z=479 (M+H)⁺

The following examples are synthesized in analogy to the preparation of example 1, using the corresponding phenylene-diamines as starting materials:

| example | structure | phenylene-diamine | yield | RT (LC-MS; Method 1s): | MS(ESI pos, m/z) |
|---|---|---|---|---|---|
| 3 | | 6C | 8.9 mg (6%) | 1.54 min | 467 (M + H)⁺ |
| 4 | 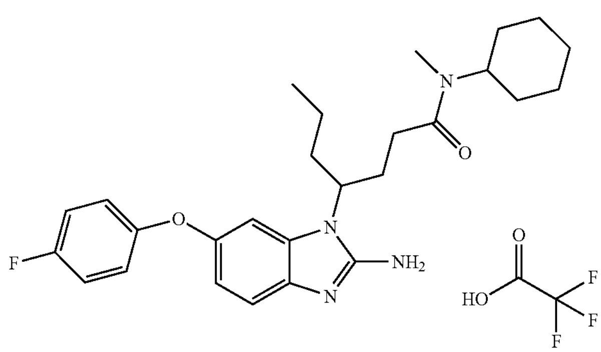 [SMILES: CCCC(CCC(=O)N(C)C1CCCCC1)n1c(N)nc2ccc(Oc3ccc(F)cc3)cc21 ; O=C(O)C(F)(F)F] | 6D | 16 mg (10%) | 1.66 min | 467 (M + H)⁺ |

-continued

| example | structure | phenylene-diamine | yield | RT (LC-MS; Method 1s): | MS(ESI pos, m/z) |
|---|---|---|---|---|---|
| 5 | 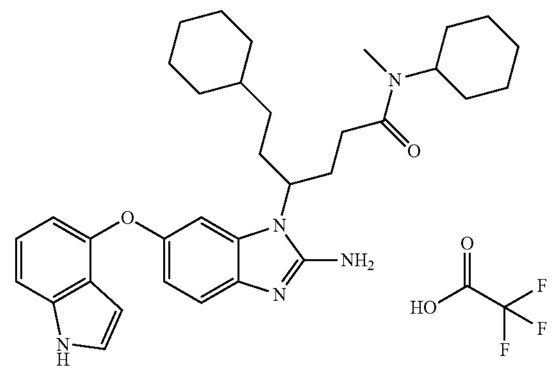 [SMILES: CN(C(=O)CCC(CCC1CCCCC1)n1c(N)nc2ccc(Oc3cccc4[nH]ccc34)cc21)C1CCCCC1 ; O=C(O)C(F)(F)F] | 6E | 11 mg (8%) | 1.55 min | 528 (M + H)+ |
| 6 | 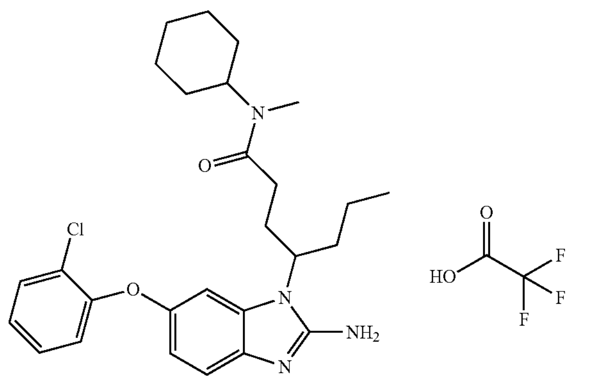 [SMILES: CCCC(CCC(=O)N(C)C1CCCCC1)n1c(N)nc2ccc(Oc3ccccc3Cl)cc21 ; O=C(O)C(F)(F)F] | 6F | 18 mg (12%) | 1.61 | 483/485 (M + H)+ (Cl) |

Example 7

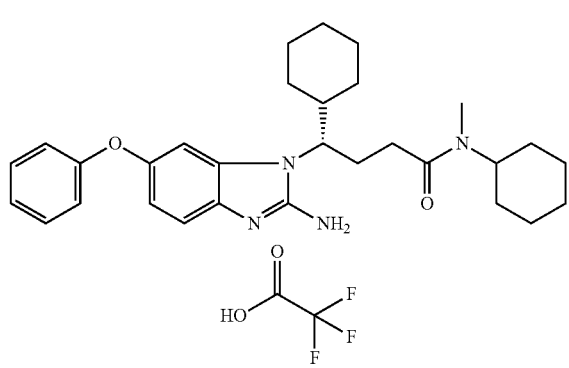

To a solution of 444 mg (0.96 mmol) 24A in 10 ml ethanol 106 mg (1.00 mmol) bromocyane and 200 μl Water is added. The mixture is stirred for 14 h at room temperature. The mixture is evaporated and the residue dissolved in acetonitrile/water/TFA (50:50:0.1) and purified by preparative HPLC (method 2). Fractions containing the product are combined and lyophilized to yield the product as a TFA salt.

yield: 390 mg (83%)

LC-MS (Method 1s): RT=1.70 min

MS (ESI pos): m/z=489 (M+H)+

Example 8

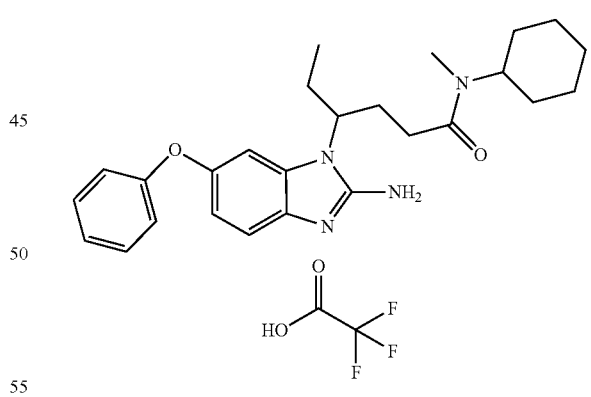

To a mixture of 50 mg (0.11 mmol) 12A and 100 μl (0.76 mmol) N-methyl-cyclohexylamine in 100 μl DMF 50 mg (0.16 mmol) TBTU and 85 μl DIPEA is added. The mixture is stirred for 3 h at room temperature. Acetonitrile/water/TFA (50:50:0.1) is added and the mixture purified by preparative HPLC (method 2). Fractions containing the product are combined and lyophilized to yield the product as a TFA salt.

yield: 32.9 mg (54%)

LC-MS (Method 1s): RT=1.50 min

MS (ESI pos): m/z=435 (M+H)+

Example 9

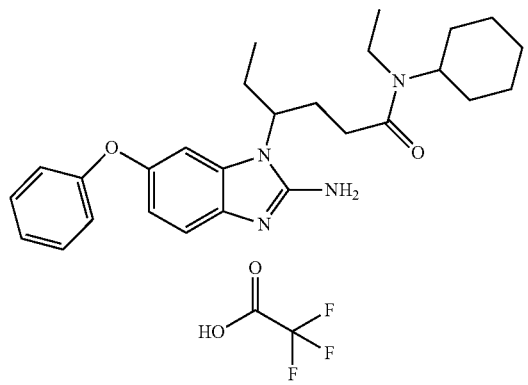

This example is synthesized in analogy to the preparation of example 8. Instead of N-methyl-cyclohexylamine N-ethyl-cyclohexylamine is used.

yield: 19.2 mg (31%)
LC-MS (Method 1s): RT=1.56 min
MS (ESI pos): m/z=449 (M+H)$^+$

Example 10

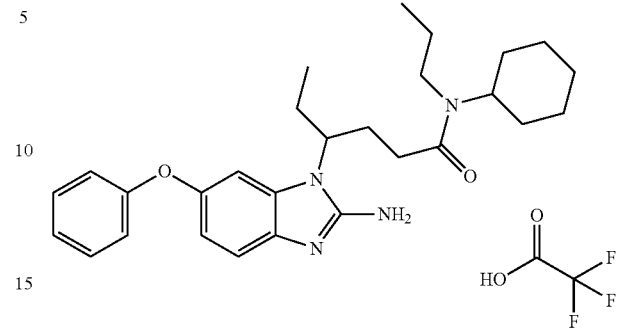

This example is synthesized in analogy to the preparation of example 8. Instead of N-methyl-cyclohexylamine N-propyl-cyclohexylamine (ChemBridge Corporation, 16981 Via Tazon, Suite G, San Diego, Calif. 92127, USA) is used.

yield: 14.1 mg (22%)
LC-MS (Method 1s): RT=1.62 min
MS (ESI pos): m/z=463 (M+H)$^+$ The following examples are synthesized in analogy to the preparation of example 8, using 12A and the corresponding amine as starting materials:

| Example | structure | amine | yield | RT (LC-MS; Method 1s): | MS(ESI pos, m/z) |
|---|---|---|---|---|---|
| 11 | 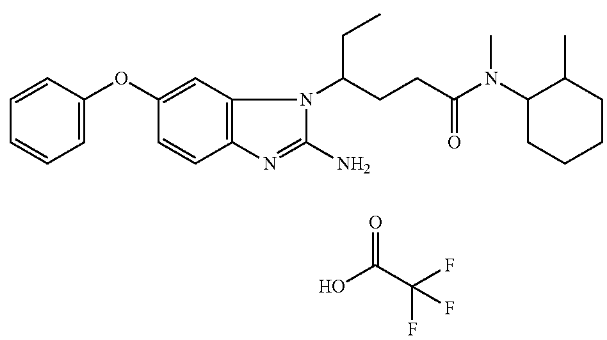 [SMILES: CCC(CCC(=O)N(C)C1CCCCC1C)n1c(N)nc2ccc(Oc3ccccc3)cc21 ; O=C(O)C(F)(F)F] | 14A | 5.8 mg (8%) | 1.56 min | 449 (M + H)$^+$ |
| 12 | 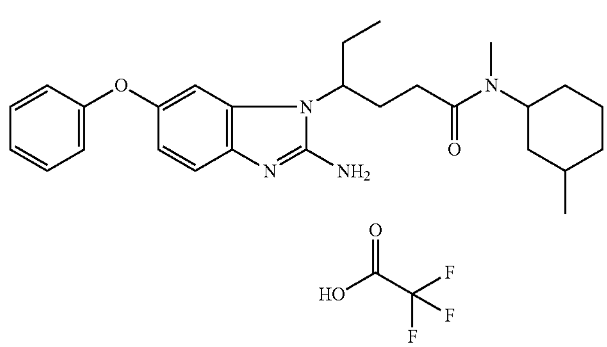 [SMILES: CCC(CCC(=O)N(C)C1CCCC(C)C1)n1c(N)nc2ccc(Oc3ccccc3)cc21 ; O=C(O)C(F)(F)F] | 14B | 20.8 mg (28%) | 1.56 min | 449 (M + H)$^+$ |

| Example | structure | amine | yield | RT (LC-MS; Method 1s): | MS(ESI pos, m/z) |
|---|---|---|---|---|---|
| 13 | 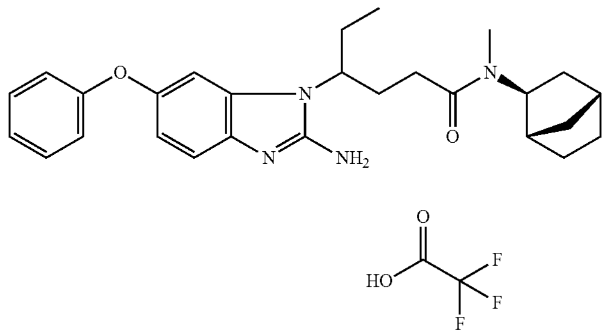 [SMILES: CCC(CCC(=O)N(C)[C@H]1C[C@@H]2CC[C@H]1C2)n1c(N)nc2ccc(Oc3ccccc3)cc21 ; O=C(O)C(F)(F)F] | 14C | 15.6 mg (21%) | 1.51 min | 447 (M + H)+ |
| 14 | 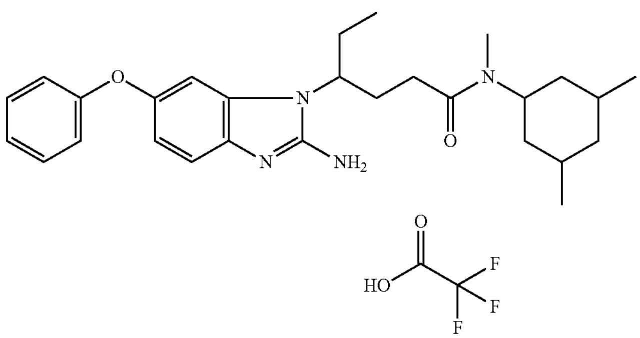 [SMILES: CCC(CCC(=O)N(C)C1CC(C)CC(C)C1)n1c(N)nc2ccc(Oc3ccccc3)cc21 ; O=C(O)C(F)(F)F] | 15A | 11.4 mg (15%) | 1.75 min | 463 (M + H)+ |

The following examples are synthesized in analogy to the preparation of example 8, using 12B and the corresponding amines as starting materials:

| Example | structure | amine | yield | RT (LC-MS; Method 1s): | MS(ESI pos, m/z) |
|---|---|---|---|---|---|
| 15 | 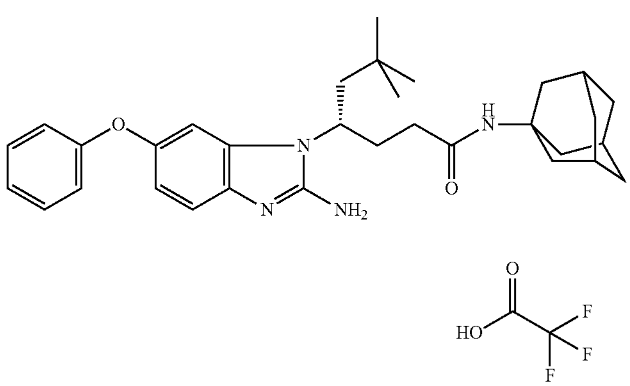 [SMILES: CC(C)(C)C[C@H](CCC(=O)NC12CC3CC(CC(C3)C1)C2)n1c(N)nc2ccc(Oc3ccccc3)cc21 ; O=C(O)C(F)(F)F] | 1-amino-adamantyl-hydro-chloride | 13 mg (14%) | 1.78 min | 515 (M + H)+ |

-continued

| Example | structure | amine | yield | RT (LC-MS; Method 1s): | MS(ESI pos, m/z) |
|---|---|---|---|---|---|
| 16 | 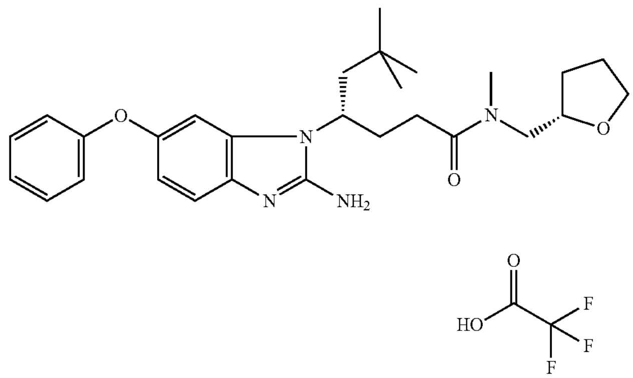 [SMILES: CN(C[C@@H]1CCCO1)C(=O)CC[C@@H](CC(C)(C)C)n1c(N)nc2ccc(Oc3ccccc3)cc21 ; O=C(O)C(F)(F)F] | 29A | 15 mg (17%) | 1.57 min | 479 (M + H)+ |
| 17 | 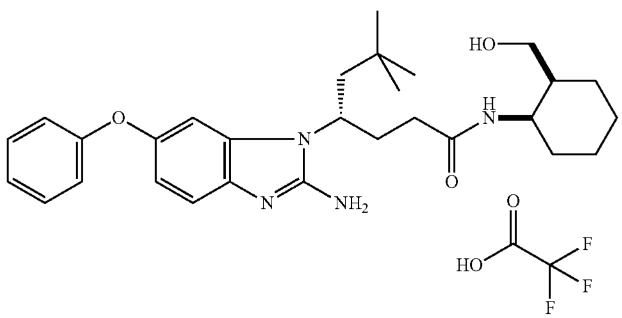 | cis-2-hydroxy-methyl-1-cyclohexyl-amine | 34 mg (37%) | 1.53 min | 473 (M + H)+ |
| 18 | 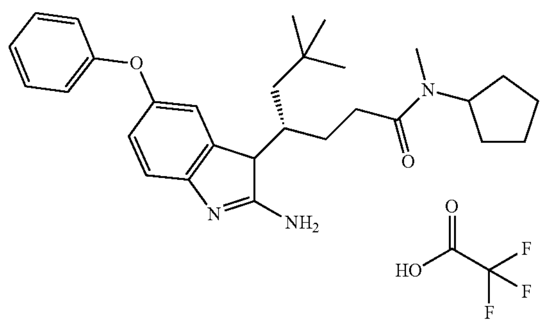 [SMILES: CN(C(=O)CC[C@@H](CC(C)(C)C)C1C(N)=Nc2ccc(Oc3ccccc3)cc21)C1CCCC1 ; O=C(O)C(F)(F)F] | N-methyl-cyclopentyl amine | 21 mg (24%) | 1.64 min | 463 (M + H)+ |

The following examples are synthesized in analogy to the preparation of example 8, using 12B and the corresponding amines as starting materials. The products are purified by preparative HPLC (method 3). Fractions containing the product are combined and lyophilized to yield the product as the free base.

| example | structure | amine | yield | RT (LC-MS; Method 1s): | MS(ESI pos, m/z) |
|---|---|---|---|---|---|
| 19 | 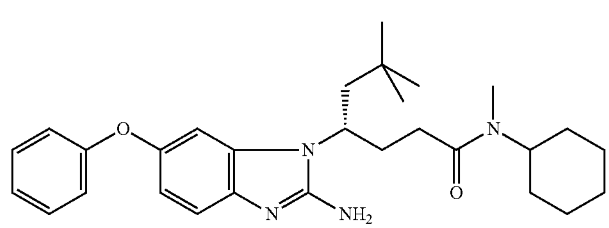 [SMILES: CN(C(=O)CC[C@@H](CC(C)(C)C)n1c(N)nc2ccc(Oc3ccccc3)cc21)C1CCCCC1] | N-methyl-cyclohex-ylamine | 6 mg (9%) | 1.77 min | 477 (M + H)+ |

The following examples are synthesized in analogy to the preparation of example 8, using 12C and the corresponding amines as starting materials:

| example | structure | amine | yield | RT (LC-MS; Method 1s): | MS(ESI pos, m/z) |
|---|---|---|---|---|---|
| 20 | 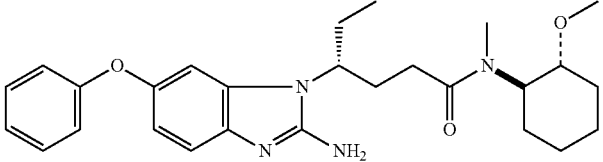 | 31A | 17 mg (27%) | 1.57 min | 465 (M + H)+ |
| 21 | 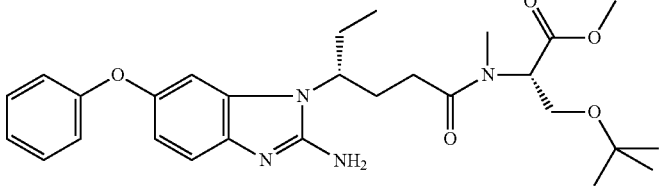 | 3-tert-Butoxy-2-methylamino-propionic acid methyl ester (Senn Chemicals (11189 Sorrento Valley Road, # 4 San Diego, CA 92121 USA) | 36 mg (16%) | 1.49 min | 511 (M + H)+ |

| example | structure | amine | yield | RT (LC-MS; Method 1s): | MS(ESI pos, m/z) |
|---|---|---|---|---|---|
| 22 | 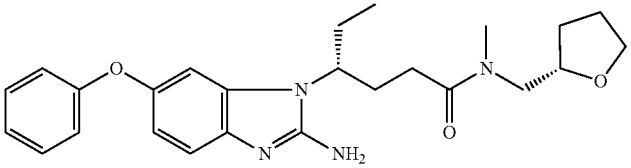 | 29A | 48 mg (65%) | 1.38 min | 437 (M + H)+ |
| 23 | 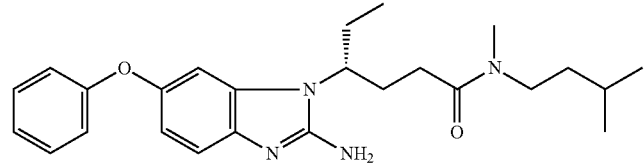 | Isopentyl-methyl-amine | 38 mg (66%) | 1.45 min | 423 (M + H)+ |

The following example is synthesized in analogy to the preparation of example 8, using 12C and the corresponding amine as starting material. After lypholization the product is dissolved in 4 N hydrogen chloride in 1,4-dioxane and evaporated to obtain the HCl salt.

| example | structure | amine | yield | RT (LC-MS; Method 1s): | MS(ESI pos, m/z) |
|---|---|---|---|---|---|
| 24 | 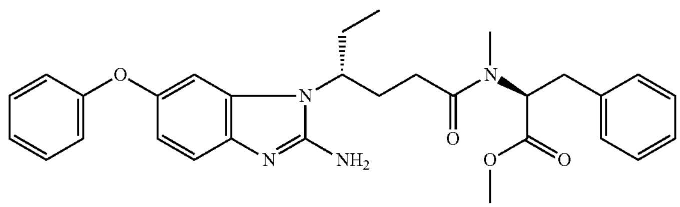 | N-methyl-L-phenyl-alanine-methylester hydrochloride (Senn Chemicals (11189 Sorrento ValleyRoad, # 4 San Diego, CA 92121 USA) | 53 mg (36%) | 1.57 | 515 (M + H)+ |

The following examples are synthesized in analogy to the preparation of example 8, using the corresponding acids and amine as starting materials:

| example | structure | acid | amine | yield | RT (LC-MS; Method 1s): | MS(ESI pos, m/z) |
|---|---|---|---|---|---|---|
| 25 | 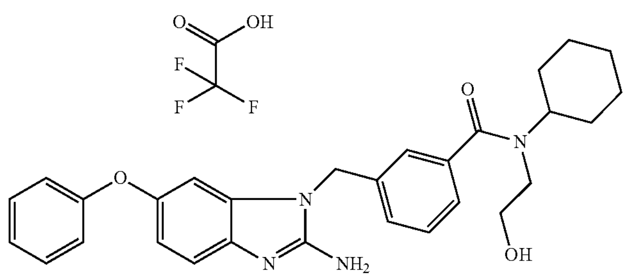 [SMILES: Nc1nc2ccc(Oc3ccccc3)cc2n1Cc1cccc(C(=O)N(CCO)C2CCCCC2)c1 ; O=C(O)C(F)(F)F] | 43C | 2-cyclohexyl-amino-ethanol | 33 mg (18%) | 1.44 | 485 (M + H)+ |
| 26 | 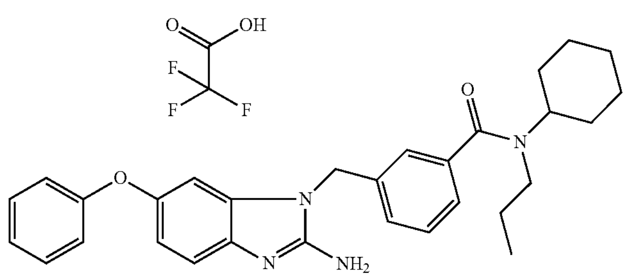 [SMILES: CCCN(C(=O)c1cccc(Cn2c(N)nc3ccc(Oc4ccccc4)cc32)c1)C1CCCCC1 ; O=C(O)C(F)(F)F] | 43C | cyclohexyl-propyl-amine | 46 mg (25%) | 1.71 | 483 (M + H)+ |
| 27 | 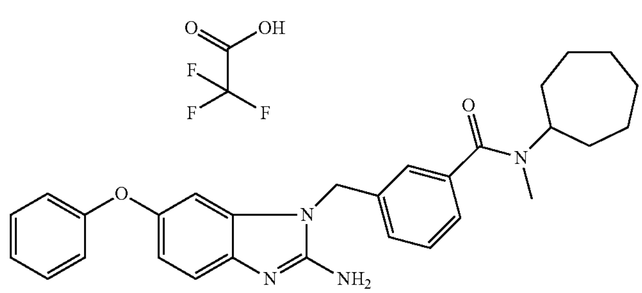 [SMILES: CN(C(=O)c1cccc(Cn2c(N)nc3ccc(Oc4ccccc4)cc32)c1)C1CCCCCC1 ; O=C(O)C(F)(F)F] | 43C | cycloheptyl-methyl-amine (Enamin, 23 A. Motrosova Street, Kiev 01103, UKRAINE) | 22 mg (15%) | 1.60 | 469 (M + H)+ |

-continued
| example | structure | acid | amine | yield | RT (LC-MS; Method 1s): | MS(ESI pos, m/z) |
|---|---|---|---|---|---|---|
| 28 | 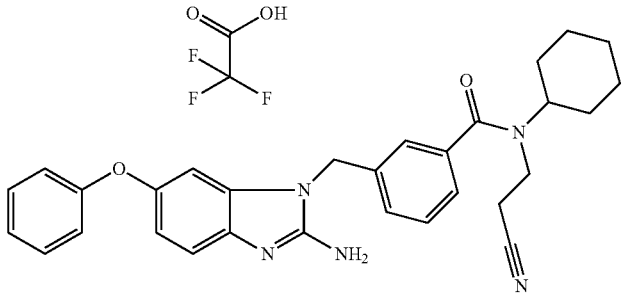 [SMILES: N#CCCN(C(=O)c1cccc(Cn2c(N)nc3ccc(Oc4ccccc4)cc32)c1)C1CCCCC1 ; O=C(O)C(F)(F)F] | 43C | 3-cyclohexyl-amino-propionitrile | 28 mg (18%) | 1.52 | 494 (M + H)+ |
| 29 | 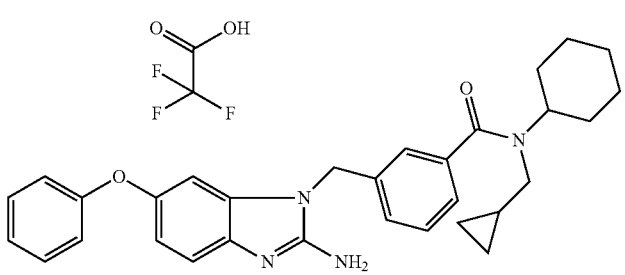 [SMILES: Nc1nc2ccc(Oc3ccccc3)cc2n1Cc1cccc(C(=O)N(CC2CC2)C2CCCCC2)c1 ; O=C(O)C(F)(F)F] | 43C | cyclohexyl-cyclopropyl methyl-amine | 30 mg (24%) | 1.64 | 495 (M + H)+ |
| 30 | 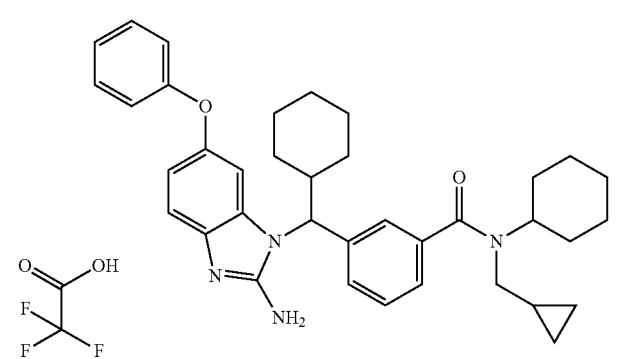 [SMILES: O=C(O)C(F)(F)F ; Nc1nc2ccc(Oc3ccccc3)cc2n1C(c1cccc(C(=O)N(CC2CC2)C2CCCCC2)c1)C1CCCCC1] | 43A | cyclohexyl-cyclopropyl methyl-amine | 73 mg (59%) | 1.91 | 577 (M + H)+ |
| 31 | 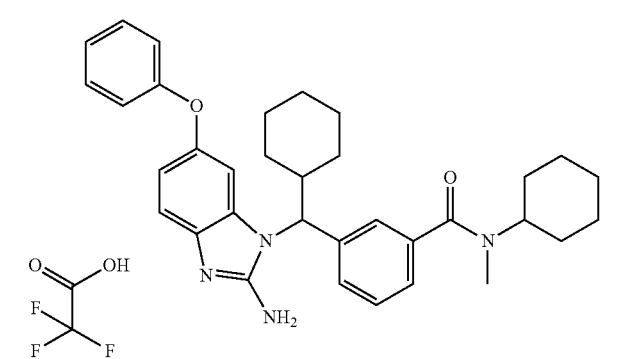 [SMILES: O=C(O)C(F)(F)F ; CN(C(=O)c1cccc(C(C2CCCCC2)n2c(N)nc3ccc(Oc4ccccc4)cc32)c1)C1CCCCC1] | 43A | cyclohexyl-methyl-amine | 43 mg (37%) | 1.78 | 537 (M + H)+ |

-continued

| example | structure | acid | amine | yield | RT (LC-MS; Method 1s): | MS(ESI pos, m/z) |
|---|---|---|---|---|---|---|
| 32 | 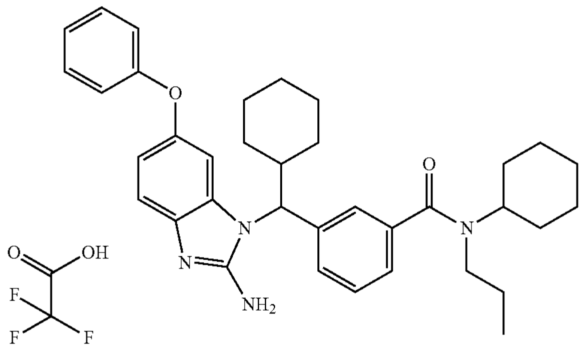 [SMILES: O=C(O)C(F)(F)F ; CCCN(C(=O)c1cccc(C(C2CCCCC2)n2c(N)nc3ccc(Oc4ccccc4)cc32)c1)C1CCCCC1] | 43A | cyclohexyl-propyl-amine (vendor: see example 23) | 33 mg (27%) | 1.90 | 565 (M + H)+ |
| 33 | 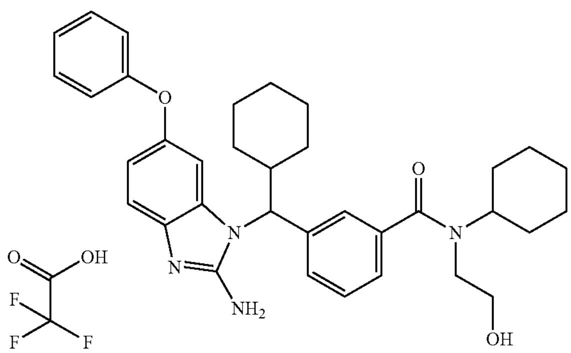 [SMILES: O=C(O)C(F)(F)F ; Nc1nc2ccc(Oc3ccccc3)cc2n1C(c1cccc(C(=O)N(CCO)C2CCCCC2)c1)C1CCCCC1] | 43A | 2-cyclohexyl amino-ethanol | 38 mg (31%) | 1.65 | 567 (M + H)+ |
| 34 | 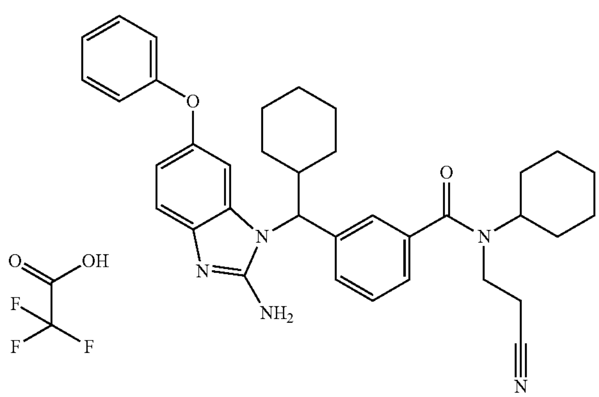 [SMILES: O=C(O)C(F)(F)F ; N#CCCN(C(=O)c1cccc(C(C2CCCCC2)n2c(N)nc3ccc(Oc4ccccc4)cc32)c1)C1CCCCC1] | 43A | 3-cyclohexyl-amino-propionitrile | 28 mg (23%) | 1.74 | 576 (M + H)+ |
| 35 | 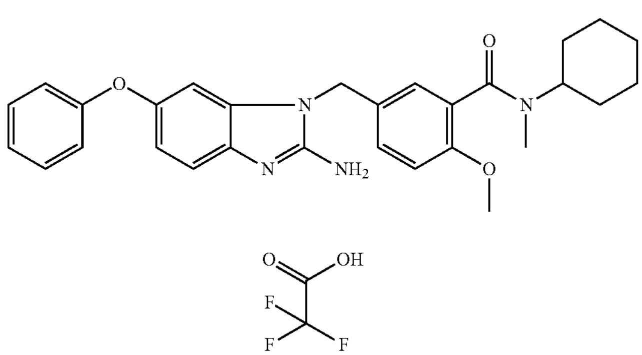 [SMILES: COc1ccc(Cn2c(N)nc3ccc(Oc4ccccc4)cc32)cc1C(=O)N(C)C1CCCCC1 ; O=C(O)C(F)(F)F] | 43B | cyclohexyl-methyl-amine | 63 mg (30%) | 1.49 | 485 (M + H)+ |

-continued

| example | structure | acid | amine | yield | RT (LC-MS; Method 1s): | MS(ESI pos, m/z) |
|---|---|---|---|---|---|---|
| 36 | 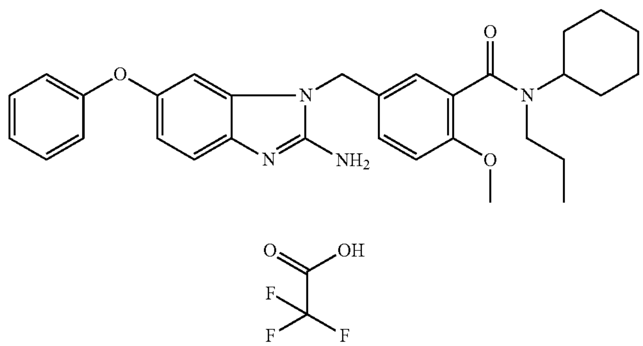 [SMILES: CCCN(C(=O)c1cc(Cn2c(N)nc3ccc(Oc4ccccc4)cc32)ccc1OC)C1CCCCC1 ; O=C(O)C(F)(F)F] | 43B | cyclohexyl-propyl-amine (vendor: see example 23) | 63 mg (29%) | 1.68 | 513 (M + H)+ |
| 37 | 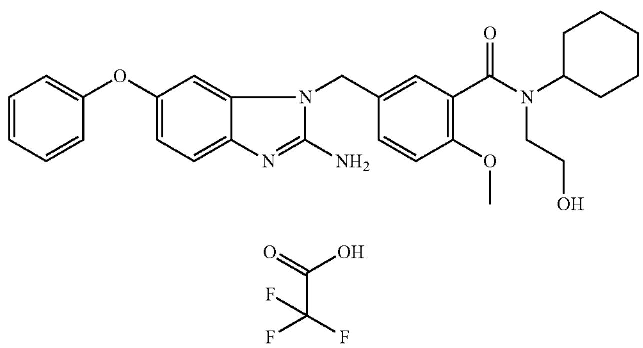 [SMILES: COc1ccc(Cn2c(N)nc3ccc(Oc4ccccc4)cc32)cc1C(=O)N(CCO)C1CCCCC1 ; O=C(O)C(F)(F)F] | 43B | 2-cyclohexyl amino-ethanol | 56 mg (25%) | 1.41 | 515 (M + H)+ |
| 38 | 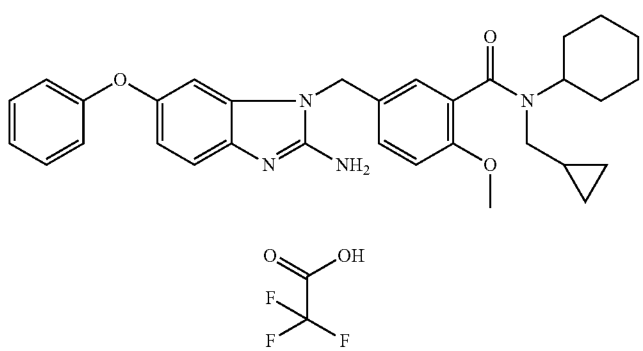 [SMILES: COc1ccc(Cn2c(N)nc3ccc(Oc4ccccc4)cc32)cc1C(=O)N(CC1CC1)C1CCCCC1 ; O=C(O)C(F)(F)F] | 43B | cyclohexyl-cyclopropyl methyl-amine | 39 mg (17%) | 1.67 | 525 (M + H)+ |
| 39 | 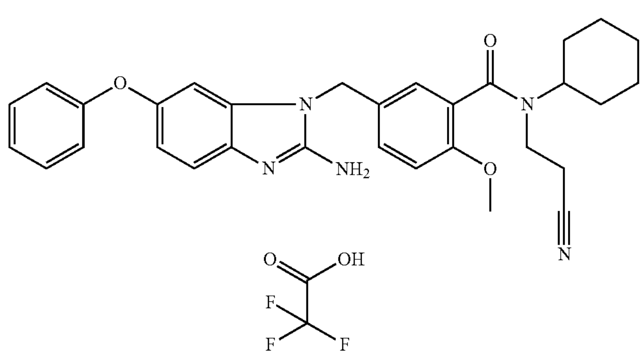 [SMILES: COc1ccc(Cn2c(N)nc3ccc(Oc4ccccc4)cc32)cc1C(=O)N(CCC#N)C1CCCCC1 ; O=C(O)C(F)(F)F] | 43B | 3-cyclohexyl amino-propionitrile | 23 mg (10%) | 1.50 | 524 (M + H)+ |

| example | structure | acid | amine | yield | RT (LC-MS; Method 1s): | MS(ESI pos, m/z) |
|---|---|---|---|---|---|---|
| 40 | 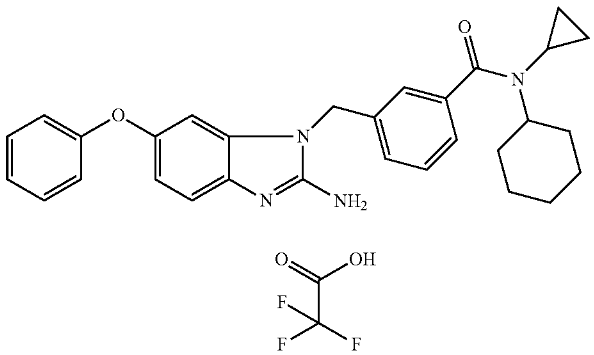 [SMILES: Nc1nc2ccc(Oc3ccccc3)cc2n1Cc1cccc(C(=O)N(C2CCCCC2)C2CC2)c1 ; O=C(O)C(F)(F)F] | 43C | 32A | 10 mg (5%) | 1.69 | 481 (M + H)+ |

Example 41

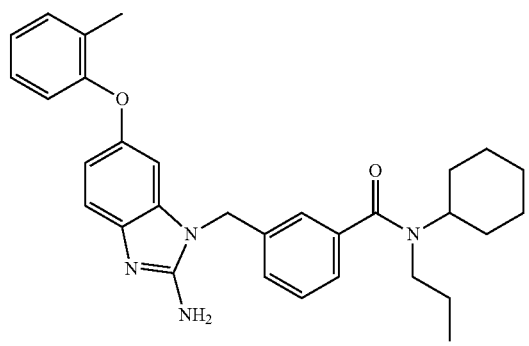

Bromocyane (36 mg, 0.34 mmol) is added to a solution of 160 mg (0.34 mmol) phenylene-diamine 40D in 11 ml ethanol/water (10:1) and stirred for 12 h at room temperature. The mixture is evaporated and the residue dissolved in acetonitrile/water/TFA (50:50:0.1) and purified by preparative HPLC (method 2). Fractions containing the product are combined and lyophilized to yield the product as a TFA salt.

yield: 115 mg (56%)
LC-MS (Method 1s): RT=1.73 min
MS (ESI pos): m/z=497 (M+H)+

The following examples are synthesized in analogy to the preparation of example 41, using the corresponding phenylene-diamines as starting materials:

| example | structure | phenylene-diamine | yield | RT (LC-MS; Method 1s): | MS(ESI pos, m/z) |
|---|---|---|---|---|---|
| 42 | 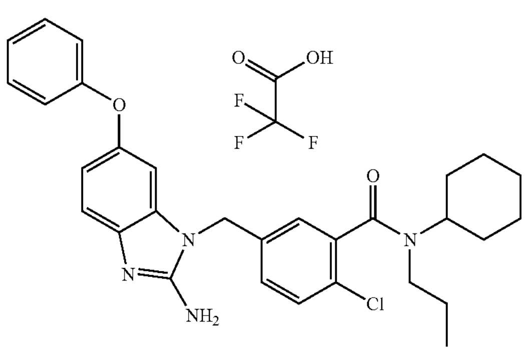 [SMILES: CCCN(C(=O)c1cc(Cn2c(N)nc3ccc(Oc4ccccc4)cc32)ccc1Cl)C1CCCCC1 ; O=C(O)C(F)(F)F] | 40E | 278 mg (57%) | 1.78 | 517/519 (M + H)+ (Cl) |

-continued

| example | structure | phenylene-diamine | yield | RT (LC-MS; Method 1s): | MS(ESI pos, m/z) |
|---|---|---|---|---|---|
| 43 | 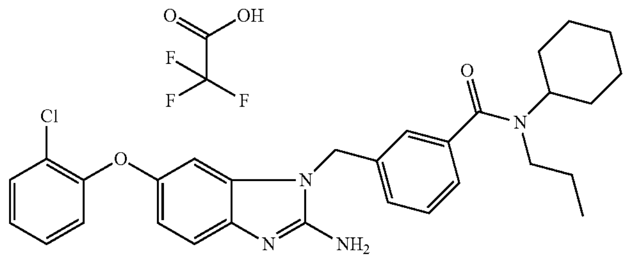 [SMILES: CCCN(C(=O)c1cccc(Cn2c(N)nc3ccc(Oc4ccccc4Cl)cc32)c1)C1CCCCC1 ; O=C(O)C(F)(F)F] | 40F | 360 mg (74%) | 1.75 | 517/519 (M + H)+ (Cl) |
| 44 | 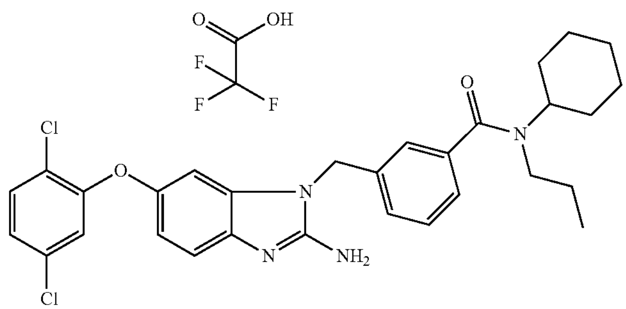 [SMILES: CCCN(C(=O)c1cccc(Cn2c(N)nc3ccc(Oc4cc(Cl)ccc4Cl)cc32)c1)C1CCCCC1 ; O=C(O)C(F)(F)F] | 40G | 170 mg (50%) | 1.84 | 551/553/555 (M + H)+(Cl) |
| 45 | 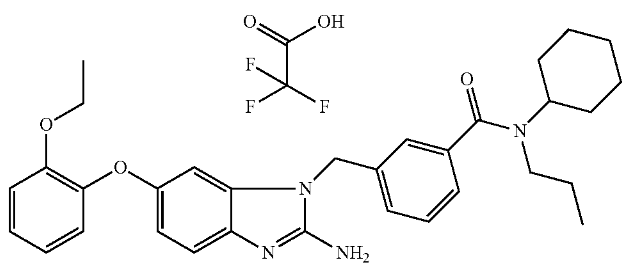 | 40H | 73 mg (60%) | 1.73 | 527 (M + H)+ |
| 46 | 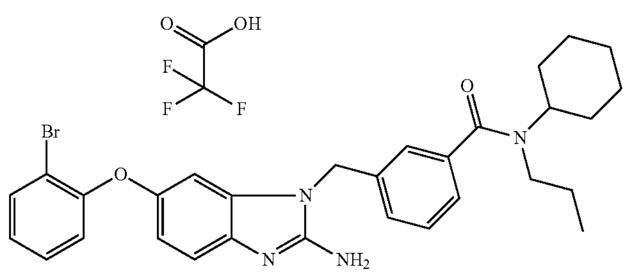 [SMILES: CCCN(C(=O)c1cccc(Cn2c(N)nc3ccc(Oc4ccccc4Br)cc32)c1)C1CCCCC1 ; O=C(O)C(F)(F)F] | 40I | 100 mg (33%) | 1.78 | 561/563 (M + H)+ (Br) |
| 47 | 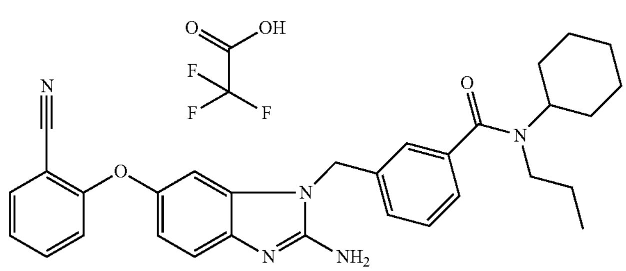 | 40J | 80 mg (26%) | 1.59 | 508 (M + H)+ |

-continued

| example | structure | phenylene-diamine | yield | RT (LC-MS; Method 1s): | MS(ESI pos, m/z) |
|---|---|---|---|---|---|
| 48 | 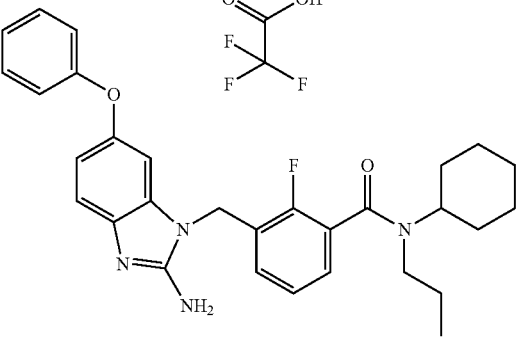 | 40K | 104 mg (45%) | 1.66 | 501 (M + H)+ |
| 49 | 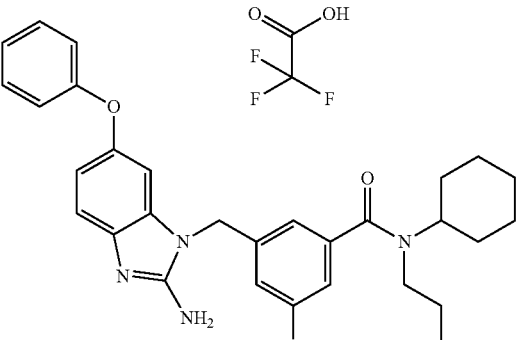 | 40L | 824 mg (58%) | 1.70 | 501 (M + H)+ |

Example 50

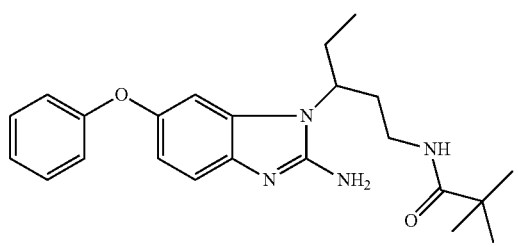 [SMILES: CCC(CCNC(=O)C(C)(C)C)n1c(N)nc2ccc(Oc3ccccc3)cc21]

40

The diamine bis-trifluoroacetate 42A (150 mg, 0.28 mmol) and 143 μl (0.84 mmol) DIPEA are dissolved in 5.0 ml of DCM. A solution of 34 mg (0.28 mmol) pivaloyl chloride in 1 ml DCM is added. Water (5 ml) is added after 1 h at room temperature.

The organic layer is separated and the solvent evaporated under reduced pressure. The remaining material is triturated with diethylether. The product is obtained after filtration as white crystals.

yield: 75 mg (68%)

LC-MS (Method 1s): RT=1.47 min

MS (ESI pos): m/z=395 (M+H)+

Example 51

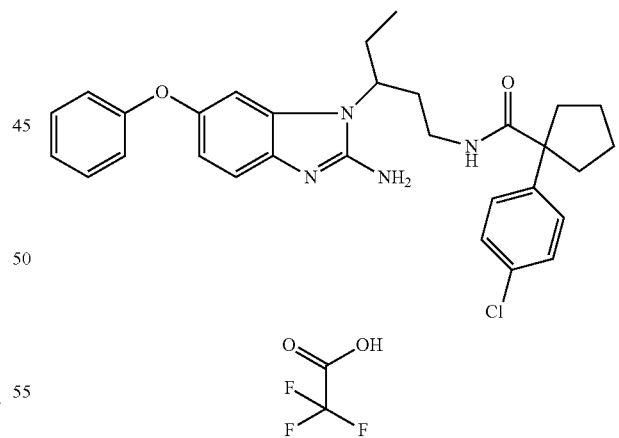

This example is synthesized in analogy to the preparation of example 50. Instead of pivaloyl chloride 1-(4-chloro-phenyl)-cyclopentanecarbonyl chloride is used. The obtained material is dissolved in acetonitrile/water/TFA (50:50:0.1) and purified by preparative HPLC (method 2). Fractions containing the product are combined and lyophilized to yield the product as a TFA salt.

yield: 120 mg (68%)

LC-MS (Method 1s): RT=1.79 min

MS (ESI pos): m/z=517/519 (M+H)+ (Cl)

Example 52

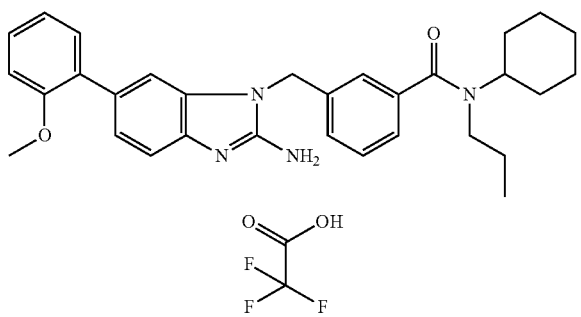 [SMILES: CCCN(C(=O)c1cccc(Cn2c(N)nc3ccc(-c4ccccc4OC)cc32)c1)C1CCCCC1 ; O=C(O)C(F)(F)F]

The amine trifluoroacetate 41B (150 mg, 0.26 mmol) and 51 mg (0.33 mmol) 2-methoxyphenylboronic acid are suspended in 4.0 ml toluene. A solution of 169 mg (0.77 mmol) potassium phosphate in 0.50 ml water is added and argon is bubbled through the suspension for 3 min. 19 mg (0.02 mmol) of tris(dibenzylideneacetone)-dipalladium(0) and 10 mg (0.03 mmol) of N-phenyl-2-(di-tert-butylphosphino)pyrrole are added and the mixture is heated under argon to 100° C. for 12 h. The mixture is filtered through a pad of celite and the filtrate is evaporated under reduced pressure. The obtained material is dissolved in acetonitrile/water/TFA (50:50:0.1) and purified by preparative HPLC (method 2). Fractions containing the product are combined and lyophilized to yield the product as a TFA salt.

yield: 25 mg (16%)

LC-MS (Method 1s): RT=1.69 min

MS (ESI pos): m/z=497 (M+H)$^+$

Example 53

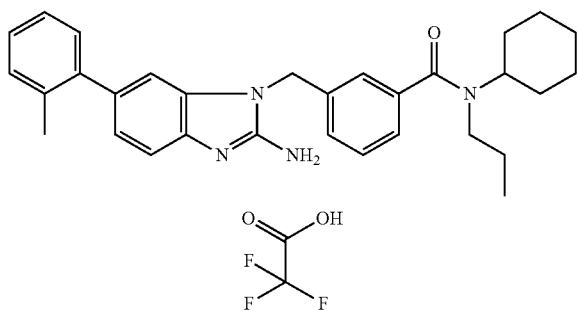

This example is synthesized in analogy to the preparation of example 52. Instead of 2-methoxyphenylboronic acid 2-methylphenylboronic acid is used. The obtained material is dissolved in acetonitrile/water/TFA (50:50:0.1) and purified by preparative HPLC (method 2). Fractions containing the product are combined and lyophilized to yield the product as a TFA salt.

yield: 39 mg (26%)

LC-MS (Method 1s): RT=1.72 min

MS (ESI pos): m/z=481 (M+H)$^+$

Example 54

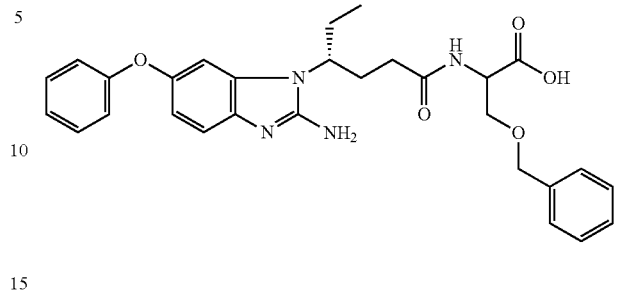

To 20 mg (0.031 mmol) 45A dissolved in 0.5 ml methanol 0.5 ml 2 N sodium hydroxide solution is added. The mixture is stirred for 14 h, neutralized with 1 N hydrochloric acid. The methanol is evaporated and the residue extracted with DCM. It is dried, filtered and the solvent evaporated to give a solid.

yield: 4.2 mg (26%)

LC-MS (Method 1s): RT=1.49 min

MS (ESI pos): m/z=517 (M+H)$^+$

Example 55

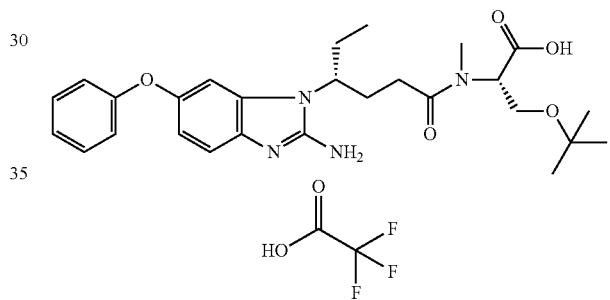

To 15 mg (0.024 mmol) 21 dissolved in 0.5 ml methanol 0.5 ml 2 N sodium hydroxide solution is added. The mixture is stirred for 14 h, the methanol is evaporated and the residue extracted with DCM. It is dried, filtered and the solvent evaporated. The crude material is purified by HPLC (method 2). Fractions containing the product are combined and lyophilized to yield the product as a TFA salt.

yield: 3.3 mg (23%)

LC-MS (Method 1s): RT=1.49 min

MS (ESI pos): m/z=517 (M+H)$^+$

Biological Examples

The compounds according to the invention inhibit the proteolysis of the APP protein between the amino acids Met595 and Asp596 (the numbering relates to the APP695 isoform) or the proteolysis of other APP isoforms such as APP751 and APP770 or mutated APP at the corresponding site, which is also referred to as the β-secretase cleavage site. The inhibition of the β-secretase should therefore lead to a reduced production of the β-amyloid peptide (Aβ).

The activity of the β-secretase may be investigated in assays based on different detection techniques. In the test set-up a catalytically active form of β-secretase is incubated with a potential substrate in a suitable buffer. The reduction in the substrate concentration or the increase in the product concentration may be monitored using various technologies as a function of the substrate used: HPLS-MS analysis, fluorescence assays, fluorescence-quenching assays, luminescence assays are a non-representative selection of the various possibilities. Assay systems in which the effectiveness of a compound can be demonstrated are described e.g. in U.S. Pat. Nos. 5,942,400 and 5,744,346 and hereinafter. An alternative assay format comprises displacing a known β-secretase ligand with a test substance (US 2003/0125257).

As the substrate, either the APP protein or parts thereof or any amino acid sequence which can be hydrolysed by β-secretase may be used. A selection of such sequences can be found for example in Tomasselli et al. 2003 in J. Neurochem 84: 1006. A peptide sequence of this kind may be coupled to suitable dyes which make it possible to detect proteolysis indirectly.

The enzyme source used may be the total β-secretase enzyme or mutants with a catalytic activity or just parts of the β-secretase which still contain the catalytically active domain. Various forms of β-secretase are known and available and may be used as the enzyme source in a corresponding test set-up. This includes the native enzyme as well as the recombinant or synthetic enzyme. Human β-secretase is known by the name Beta Site APP Cleaving Enzyme (BACE), Asp2 and memapsin 2 and is described e.g. in U.S. Pat. No. 5,744,346 and in Patent Applications WO 98/22597, WO 00/03819, WO 01/23533, and WO 00/17369, as well as in the scientific literature (Hussain et. al., 1999, Mol. Cell. Neurosci. 14: 419-427; Vassar et. al., 1999, Science 286:735-741; Yan et. al., 1999, Nature 402: 533-537; Sinha et. al., 1999, Nature 40: 537-540; and Lin et. al., 2000, PNAS USA 97:1456-1460). Synthetic forms of the enzyme have also been described (WO 98/22597 and WO 00/17369). β-secretase may be extracted and purified for example from human brain tissue or produced recombinantly in mammalian cell cultures, insect cell cultures, yeasts or bacteria.

To calculate the IC50 value of a substance different amounts of substance are incubated with the β-secretase in an assay. The IC50 value of a compound is defined as the concentration of substance at which a 50% reduction in the detected signal is measured, compared with the mixture without the test compound. Substances are evaluated as inhibiting β-secretase if under these conditions their IC50 value is less than 50 µM, preferably less than 10 µM and particularly preferably less than 1 µM.

In detail, an assay for detecting β-secretase activity may be as follows:

The ectodomain of BACE (amino acids 1-454) fused to the recognition sequence for an anti-Myc antibody and a polyhistidine is secreted overnight by HEK293/APP/BACE$_{ect}$ cells in OptiMEM® (Invitrogen). A 10 µl aliquot of this cell culture supernatant is used as the enzyme source. The enzyme is stable over more than 3 months' storage at 4° C. or −20° C. in OptiMEM®. The substrate used is a peptide with the amino acid sequence SEVNLDAEFK, to which the Cy3 fluorophore (Amersham) is coupled N-terminally and the Cy5Q fluorophore (Amersham) is coupled C-terminally. The substrate is dissolved in DMSO in a concentration of 1 mg/ml and used in the experiment in a concentration of 1 µM. The test mixture also contains 20 mM NaOAc, pH 4.4 and a maximum of 1% DMSO. The test is carried out in a 96-well plate in a total volume of 200 µl for 30 minutes at 30° C. The cleaving of the substrate is recorded kinetically in a fluorimeter (ex: 530 nm, em: 590 nm). The assay is started by adding the substrate.

Mixtures without enzyme or without inhibitor are included in each plate as controls. The IC50 value for the test compound is calculated using standard software (e.g. GraphPad Prism®) from the percentage inhibition of the substance at different test concentrations. The relative inhibition is calculated from the reduction in signal intensity in the presence of the substance, compared with the signal intensity without the substance.

The compounds listed in table 9 have IC50 values of less than 10 µM, measured using the test described hereinbefore.

The activity of the β-secretase may also be investigated in cellular systems. As APP is a substrate for β-secretase and Aβ is secreted by the cells after processing of APP by β-secretase has taken place, cellular test systems for detecting β-secretase activity are based on the detection of the amount of Aβ formed over a defined period.

A selection of suitable cells includes, but is not restricted to, human embryonic kidney fibroblasts 293 (HEK293), Chinese Hamster Ovary cells (CHO), human H4 neuroglioma cells, human U373 MG astrocytoma glioblastoma cells, murine neuroblastoma N2a cells, which stably or transiently express APP or mutated forms of APP, such as e.g. the Swedish or London or Indiana mutation. The transfection of the cells is carried out e.g. by cloning the cDNA from human APP into an expression vector such as e.g. pcDNA3 (Invitrogen) and adding it to the cells with a transfection reagent such as e.g. lipofectamine (Invitrogen) in accordance with the manufacturer's instructions.

The secretion of Aβ may also be measured from cells without genetic modification with a suitably sensitive Aβ detection assay such as e.g. ELISA or HTRF. Cells which may be used for this may be for example human IMR32 neuroblastoma cells, besides various other cells.

The secretion of Aβ may also be investigated in cells obtained from the brains of embryos or the young of APP transgenic mice, e.g. in those of Hsiao et al 1996 Science 274: 99-102, or from other organisms such as e.g. guinea pigs or rats. Substances are evaluated as inhibiting β-secretase if under these conditions their $IC_{50}$ value is less than 50 µM, preferably less than 10 µM, particularly preferably less than 1 µM.

An example of the method used to carry out a cell assay is described below: U373-MG cells which stably express APP (isoform 751) are cultivated in a culture medium such as DMEM+glucose, sodium pyruvate, glutamine and 10% FCS at 37° C. in a steam-saturated atmosphere with 5% $CO_2$. In order to investigate the β-secretase inhibiting activity of substances the cells are incubated with different concentrations of the compound between 50 µM and 50 pM for 12-24 h. The substance is dissolved in DMSO and diluted for the assay in culture medium such that the DMSO concentration does not exceed 0.5%. The production of Aβ during this period is determined using an ELISA which uses the antibodies 6E10 (Senentek) and SGY3160 (C. Eckman, Mayo Clinic, Jacksonville, Fla., USA) as capturing antibodies which are bound to the microtitre plate and Aβ40 and Aβ42-specific antibodies (Nanotools, Germany), coupled to alkaline phosphatase as detection antibodies. Non-specific binding of proteins to the microtitre plate is prevented by blocking with Block Ace (Serotec) before the addition of the Aβ-containing culture supernatant. The amounts of Aβ contained in the cell supernatant are quantified by adding the substrate for alkaline phosphatase CSPD/Sapphire II (Applied Biosystems) in accordance with the manufacturer's instructions. Possible non-specific effects of the test compound on the vitality of the cell are ruled out by determining this by AlamarBlue (Resazurin) reduction over a period of 60 minutes.

The potency of non-toxic substances is determined by calculating the concentration which results in a 50% reduction in the amount of Aβ secreted by comparison with untreated cells.

In addition, various animal models may be used to investigate the β-secretase activity and/or the APP processing and the release of Aβ. Thus, for example, transgenic animals which express APP and/or β-secretase are used to test the inhibitory activity of compounds of this invention. Corresponding transgenic animals are described e.g. in U.S. Pat. Nos. 5,877,399, 5,612,486, 5,387,742, 5,720,936, 5,850,003, 5,877,015 and 5,811,633, and in Games et. al., 1995, Nature 373: 523. It is preferable to use animal models which exhibit some of the characteristics of AD pathology. The addition of β-secretase inhibitors according to this invention and subsequent investigation of the pathology of the animals is another alternative for demonstrating the β-secretase inhibition by the compounds. The compounds are administered in such a way that they are able to reach their site of activity in a pharmaceutically effective form and amount.

The Examples that follow are intended to illustrate the invention, without restricting it thereto.

Method of Treatment

The present invention is directed to compounds of general formula 1, which are here shown to be useful in the prevention and/or treatment of a disease and/or condition wherein the inhibition of the cleavage of APP (Amyloid Precursor Protein) mediated by β-secretase is of therapeutic benefit, including but not limited to AD.

Accordingly, the present invention relates to a compound of general formula 1 as a medicament.

Furthermore, the present invention relates to the use of a compound of general formula 1 for the preparation of a medicament for treatment or prevention of a disease and/or condition wherein the inhibition of the cleavage of APP (Amyloid Precursor Protein) mediated by β-secretase is of therapeutic benefit.

Furthermore, the present invention relates to the use of a compound of general formula 1 for the preparation of a medicament for treatment or prevention of Alzheimer's disease, MCI ("mild cognitive impairment"), trisomy 21 (Down's syndrome), cerebral amyloid angiopathy, degenerative dementias, hereditary cerebral haemorrhage with amyloidosis, Dutch type (HCHWA-D), Alzheimer's dementia with Lewy bodies, trauma, stroke, pancreatitis, Inclusion Body Myositis (IBM), and other peripheral amyloidoses, diabetes and arteriosclerosis.

Furthermore, the present invention preferably relates to the use of a compound of general formula 1 for the preparation of a medicament for treatment or prevention of Alzheimer's disease.

In a further aspect of the present invention the present invention relates to methods for the treatment or prevention of above mentioned diseases and conditions, which method comprises the administration of an effective amount of a compound of general formula 1 to a subject.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom inhibition of the cleavage of APP (Amyloid Precursor Protein) mediated by β-secretase is desired.

The dose range of the compounds of general formula 1 applicable per day is usually from 0.1 to 1000 mg, preferably from 2 to 500 mg, more preferably from 5 to 250 mg, most preferably from 10 to 100 mg. A dosage unit (e.g. a tablet) preferably contains between 2 and 250 mg, particularly preferably between 10 and 100 mg of the compounds according to the invention.

Preferably, the pharmaceutical formulations are administered 1, 2, 3 or 4 times, particularly preferably 1-2 times, most preferably once a day.

The actual pharmaceutically effective amount or therapeutic dosage will of course depend on factors known by those skilled in the art such as age and weight of the patient, route of administration and severity of disease.

In another aspect the present invention is directed to the use of the compounds of general formula 1 in the preparation and execution of screening assays for compounds that modulate the activity of β-secretase. Furthermore, the compounds of this invention are useful in establishing or determining the binding site of other compounds to β-secretase, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commercial kit, for example, for use in pharmaceutical research involving the aforementioned diseases. The compounds of the instant invention are also useful for the evaluation of putative specific inhibitors of β-secretase.

Combinations

The compounds of general formula 1 may be used on their own or combined with other active substances of formula 1 according to the invention. The compounds of general formula 1 may optionally also be combined with other pharmacologically active substances. These include, for example beta-secretase inhibitors; gamma-secretase inhibitors; amyloid aggregation inhibitors such as e.g. alzhemed; directly or indirectly acting neuroprotective substances; anti-oxidants, such as e.g. vitamin E or ginkolide; anti-inflammatory substances, such as e.g. Cox inhibitors, NSAIDs additionally or exclusively having Aβ lowering properties; HMG-CoA reductase inhibitors (statins); acetylcholinesterase inhibitors, such as donepezil, rivastigmine, tacrine, galantamine; NMDA receptor antagonists such as e.g. memantine; AMPA agonists; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE-IV and PDE-IX inhibitors, $GABA_A$ inverse agonists, nicotinic agonists, histamine H3 antagonists, 5 HAT-4 agonists or partial agonists, 5HT-6 antagonists, a2-adrenoreceptor antagonists, muscarinic M1 agonists, muscarinic M2 antagonists, metabotropic glutamate-receptor 5 positive modulators, and other substances that modulate receptors or enzymes in a manner such that the efficacy and/or safety of the compounds according to the invention is increased and/or unwanted side effects are reduced.

This invention further relates to pharmaceutical compositions containing one or more, preferably one active substance, which is selected from the compounds according to the invention and/or the corresponding salts, as well as one or more, preferably one active substance selected from among alzhemed, vitamin E, ginkolide, donepezil, rivastigmine, tacrine, galantamine, memantine, ibutamoren mesylate, capromorelin, minocyclin and/or rifampicin, optionally together with one or more inert carriers and/or diluents.

The compounds according to the invention may also be used in combination with immunotherapies such as e.g. active immunisation with Abeta or parts thereof or passive immunisation with humanised anti-Abeta antibodies for the treatment of the above-mentioned diseases and conditions.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e the compounds of the present invention are provided in one dosage form and one or more of the above mentioned combination partners is provided in another dosage form. These two dosage forms may be equal dosage forms, for example a co-administration of two tablets, one containing a therapeutically effective amount of the compound of the present invention and one containing a therapeutically effective amount of the above mentioned combination partner. It is also possible to combine different administration forms, if desired. Any type of suitable administration forms may be provided.

The compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners is expediently 1/5 of the normally recommended lowest dose up to 1/1 of the normally recommended dose.

The dosage forms are administered to the patient 1, 2, 3, or 4 times daily. It is preferred that the compounds of the invention be administered either three or fewer times, more preferably once or twice daily.

Therefore, in another aspect the invention relates to the use of a combination of compounds of general formula 1, or a pharmaceutically acceptable salt thereof, and of one or more, preferably one active ingredient described above as combination partners, for the manufacture of a medicament for the treatment and/or prevention of diseases and/or conditions which can be influenced by the inhibition of β-secretase.

In another aspect, the invention relates to the use of a compound of general formula 1, or a pharmaceutically acceptable salt thereof, for the manufacture of a medicament for the treatment and/or prevention of diseases or conditions which can be influenced by the inhibition of β-secretase, in combination with one or more, preferably one active ingredient described above as combination partners.

PHARMACEUTICAL FORMS

The compounds of formula 1 are administered to a mammal in a therapeutically effective amount. By "therapeutically effective amount" it is meant an amount of a compound of formula 1 that, when administered alone or in combination with an additional therapeutic agent to a mammal, is effective to prevent or ameliorate diseases, wherein the activity of a β-secretase is involved, or the progression of this disease.

The compounds according to the invention may be administered by oral, parenteral (intravenous, intramuscular etc.), intranasal, sublingual, inhalative, intrathecal, topical or rectal route. Suitable preparations for administering the compounds of formula 1 include for example patches, tablets, capsules, pills, pellets, dragees, powders, troches, suppositories, liquid preparations such as solutions, suspensions, emulsions, drops, syrups, elixirs, or gaseous preparations such as aerosols, sprays and the like. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatin and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

The dosage of the compounds according to the invention is naturally highly dependent on the method of administration and the complaint which is being treated. When administered by inhalation the compounds of formula 1 are characterised by a high potency even at doses in the μg range. The compounds of formula 1 may also be used effectively above the μg range. The dosage may then be in the gram range, for example.

In another aspect the present invention relates to the above-mentioned pharmaceutical formulations as such which are characterised in that they contain a compound of formula 1.

The following examples of formulations illustrate the present invention without restricting its scope:

EXAMPLES OF PHARMACEUTICAL FORMULATIONS

Some examples of formulations will now be described, wherein the term "active substance" denotes one or more compounds according to the invention including the salts thereof. In the case of one of the aforementioned combinations with one or more other active substances the term "active substance" also includes the additional active substances.

Example A

Tablets Containing 100 mg of Active Substance
Composition:
1 Tablet Contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| | |
|---|---|
| Weight of tablet: | 220 mg |
| Diameter: | 10 mm, biplanar, facetted on both sides and notched on one side. |

Example B

Tablets Containing 150 mg of Active Substance
Composition:
1 Tablet Contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| | |
|---|---|
| Weight of tablet: | 300 mg |
| diameter: | 10 mm, flat |

Example C

Hard Gelatine Capsules Containing 150 mg of Active Substance

1 Capsule Contains:

| | | |
|---|---|---|
| active substance | | 150.0 mg |
| corn starch (dried) | approx. | 80.0 mg |
| lactose (powdered) | approx. | 87.0 mg |
| magnesium stearate | | 3.0 mg |
| | approx. | 320.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

Example D

Suppositories Containing 150 mg of Active Substance
1 Suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:
After the suppository mass has been melted the active substance is homogeneously distributed therein and the melt is poured into chilled moulds.

Example E

Ampoules Containing 10 mg Active Substance
Composition:

| | |
|---|---|
| active substance | 10.0 mg |
| 0.01 N hydrochloric acid q.s. | |
| double-distilled water ad | 2.0 ml |

Preparation:
The active substance is dissolved in the necessary amount of 0.01 N HCl, made isotonic with common salt, filtered sterile and transferred into 2 ml ampoules.

Example F

Ampoules Containing 50 mg of Active Substance
Composition:

| | |
|---|---|
| active substance | 50.0 mg |
| 0.01 N hydrochloric acid q.s. | |
| double-distilled water ad | 10.0 ml |

Preparation:
The active substance is dissolved in the necessary amount of 0.01 N HCl, made isotonic with common salt, filtered sterile and transferred into 10 ml ampoules.

The invention claimed is:
1. A compound of formula 1

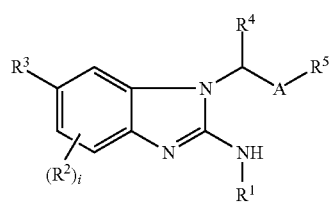

wherein
A is selected from the group GA.1 consisting of
a $C_1$-$C_3$-alkylene bridge, aryl-, heteroaryl- and heterocyclyl-,
wherein the above-mentioned members of the group GA.1 may optionally be substituted independently of one another by one or more substituents selected from the group consisting of
fluorine, chlorine, bromine, HO—, NC—, $O_2N$—, $F_3C$—, $HF_2C$—, $FH_2C$—, $F_3C$—$CH_2$—, $R^{14}$—O—$C_{1-6}$-alkyl-, $C_{1-6}$-alkyl-, $C_{1-6}$-alkyl-O—, $F_3C$—O—, $HF_2C$—O—, $FH_2C$—O—, $(R^{13})_2N$—, $(R^{13})_2N$—$C_{1-3}$-alkyl-, and $(R^{13})_2N$—CO—,
i is 0,
$R^1$ is selected from the group GR1.1 consisting of
H—, HO—, methyl-, ethyl-, $F_3C$—, $F_3C$—$CH_2$—, $H_3C$—O—, $H_3C$—$CH_2$—O—, $H_3C$—C(O)—, and HC(O)—,
$R^2$ is selected from the group GR2.1 consisting of
fluorine, chlorine, bromine, HO—, NC—, $O_2N$—, $F_3C$—, $HF_2C$—, $FH_2C$—, $F_3C$—$CH_2$—, $F_3C$—O—, $HF_2C$—O—, $FH_2C$—O—, $C_{1-6}$-alkyl-, $C_{1-6}$-alkyl-S—, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{14}$—O—, $R^{14}$—O—$C_{1-3}$-alkyl-, $(R^{13})_2N$—, $(R^{13})_2N$—CO—, $R^{13}$—CO—$(R^{13})N$—, $(R^{13})_2N$—CO—$(R^{13})N$—, $R^{13}$—$SO_2$—$(R^{13})N$—, $(R^{13})_2N$—$SO_2$— and $R^{13}$—$SO_2$—,
wherein the above-mentioned members of the group GR2.1 may optionally be substituted independently of one another by one or more substituents selected from the group consisting of
fluorine, chlorine, bromine, HO—, NC—, $O_2N$—, $F_3C$—, $HF_2C$—, $FH_2C$—, HO—$C_{1-6}$-alkyl-, $CH_3$—O—$C_{1-6}$-alkyl-, $C_{1-6}$-alkyl-, $C_{1-6}$-alkyl-O—, $(R^{13})_2N$—, $(R^{13})_2N$—$C_{1-3}$-alkyl-, and $(R^{13})_2N$—CO—,
$R^3$ is selected from the group GR3.1 consisting of
fluorine, chlorine, bromine, NC—, $F_3C$—, $HF_2C$—, $FH_2C$—, $F_3C$—$CH_2$—, $C_{1-6}$-alkyl-, $C_{1-6}$—alkyl-S—, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{12}$—O—, $R^{12}$—O—$C_{1-3}$-alkyl-, and $R^{12}$—CO—,
wherein the above-mentioned members of the group GR3.1 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, H—O—$C_{1-6}$-alkyl-, $CH_3$—O$C_{1-6}$alkyl, $C_{1-6}$-alkyl-, $C_{1-6}$alkyl-O— and $(R^{13})_2N$—CO—,
$R^4$ is selected from the group GR4.1 consisting of
H—, fluorine, NC—, $F_3C$—, $HF_2C$—, $FH_2C$—, $F_3C$—$CH_2$—, $C_{1-6}$-alkyl-, $C_2$-$C_6$-alkenyl, $C_{1-6}$-alkyl-S—, $C_{1-6}$-alkyl-S—$C_{1-3}$-alkyl- , $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, $R^{14}$—O—, and $R^{14}$—O—$C_{1-3}$-alkyl-,
wherein the above-mentioned members of the group GR4.1 may optionally be substituted independently of one another by one or more substituents selected from the group consisting of
fluorine, chlorine, bromine, HO—, NC—, $O_2N$—, $F_3C$—, $HF_2C$—, $FH_2C$—, $F_3C$—$CH_2$—, HO—$C_{1-6}$-alkyl-, $CH_3$—O—$C_{1-6}$-alkyl-, $C_{1-6}$-alkyl-, $C_{1-6}$-alkyl-O—, $(R^{13})_2N$—, $(R^{13})_2N$—$C_{1-3}$-alkyl-, and $(R^{13})_2N$—CO—, $R^5$ is selected from the group GR5.1 consisting of
  $R^6R^7N$—CO—, $R^8$—CO—$(R^9)N$—, and $R^{10}R^{11}N$—CO—$(R^9)N$—,
$R^6$, $R^7$, $R^8$, $R^9$, $R^{10}$, and $R^{11}$ are selected from the group GR6/11.1 consisting of
  H—, $F_3C$—, $HF_2C$—, $FH_2C$—, $F_3C$—$CH_2$—, $C_{1-8}$-alkyl-, $C_{1-6}$-alkyl-S—$C_{1-3}$-alkyl-, $C_{3-7}$-cycloalkyl-, $C_{3-7}$-cycloalkyl-$C_{1-6}$-alkyl-, $C_{6-12}$-polycycloalkyl-, aryl-, aryl-$C_{1-6}$-alkyl-, heterocyclyl-, heterocyclyl-$C_{1-6}$-alkyl-, heteroaryl-, heteroaryl-$C_{1-6}$-alkyl-, and $R^{14}$—O—$C_{1-3}$-alkyl-,
  wherein, if $R^6$ and $R^7$ or $R^{10}$ and $R^{11}$ are $C_{1-6}$-alkyl groups, those two $C_{1-6}$-alkyl groups bound to the same nitrogen atom of $R^5$ may be joined together forming, together with the nitrogen atom to which they are bound, a 3 to 7 membered heterocyclic ring, and
  wherein the above-mentioned members of the group GR6/11.1 including the the heterocyclic ring formed by the $R^6$ and $R^7$ or $R^{10}$ and $R^{11}$ $C_{1-6}$-alkyl groups and the nitrogen atom of $R^5$ may optionally be substituted independently of one another by one or more substituents selected from group GR6/11.S1 consisting of fluorine, chlorine, bromine, HO—, NC—, $F_3C$—, $HF_2C$—, $FH_2C$—, $F_3C$—$CH_2$—, HO—$C_{1-6}$-alkyl-, $C_{1-6}$-alkyl-, $C_{1-6}$-alkyl-O—, $C_{1-6}$-alkyl-O—$C_{1-6}$-alkyl-, and aryl-,
  wherein the above-mentioned aryl of group GR6/11.S1 may optionally be substituted independently of one another by one or more substituents selected from group consisting of
  fluorine, chlorine, bromine, NC—, $F_3C$—, $HF_2C$—, $FH_2C$—, HO—$C_{1-3}$-alkyl-, $C_{1-3}$-alkyl-, and $C_{1-3}$-alkyl-O—,
$R^{12}$ is selected from the group GR12.1 consisting of
  $F_3C$—, $HF_2C$—, $FH_2C$—, $F_3C$—$CH_2$—, $C_{1-6}$-alkyl-, $C_{3-6}$-alkenyl-, $C_{1-6}$-alkyl-S—$C_{1-3}$-alkyl-, $C_{1-6}$-alkyl-O—$C_{1-3}$-alkyl-, $C_{3-7}$cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, and heteroaryl-$C_{1-6}$-alkyl-,
  wherein the above-mentioned members of the group GR12.1 may optionally be substituted independently of one another by one or more substituents selected from the group consisting of
  fluorine, chlorine, bromine, $R^{14}$—O—, NC—, $O_2N$—, $F_3C$—, $HF_2C$—, $FH_2C$—, $F_3C$—$CH_2$—, $R^{14}$—O—$C_{1-6}$-alkyl-, $C_{1-6}$-alkyl-, $(R^{13})_2N$—, $(R^{13})_2N$—$C_{1-3}$-alkyl-, and $(R^{13})_2N$—CO—,
$R^{13}$ is selected from the group GR13.1 consisting of
  H—, $F_3C$—$CH_2$—, $C_{1-6}$-alkyl-, $C_{2-6}$-alkenyl-, $C_{1-6}$-alkyl-S—$C_{1-3}$-alkyl-, $C_{1-6}$-alkyl-O—$C_{1-3}$-alkyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl-, and heteroaryl-$C_{1-3}$-alkyl-,
  wherein two $C_{1-6}$-alkyl groups bound to the same nitrogen atom may be joined together forming, together with the nitrogen atom to which they are bound, a 3 to 7 membered heterocyclic ring, and wherein one of the —$CH_2$—groups of the heterocyclic ring formed may be replaced by —O—, —S—, N—H, —N($C_{3-6}$-cycloalkyl)-, —N($C_{3-6}$-cycloalkyl-$C_{1-4}$-alkyl)- or —N($C_{1-4}$-alkyl)- and
  wherein the above-mentioned members of the group GR13.1 including the heterocyclic ring formed may optionally be substituted independently of one another by one or more substituents selected from the group consisting of fluorine, chlorine, bromine, HO—, NC—, $O_2N$—, $F_3C$—, $HF_2C$—, $FH_2C$—, $F_3C$—$CH_2$—, HO—$C_{1-6}$-alkyl-, $CH_3$—O—$C_{1-6}$-alkyl-, $C_{1-6}$-alkyl-, $C_{1-6}$-alkyl-O— and $(C_{1-6}$-alkyl-$)_2N$—CO—,
$R^{14}$ is selected from the group GR14.1 consisting of
  H—, $F_3C$—, $HF_2C$—, $FH_2C$—, $F_3C$—$CH_2$—, $C_{1-6}$-alkyl-, $C_{2-6}$-alkenyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl- and heteroaryl-$C_{1-3}$-alkyl-,
  wherein the above-mentioned members of the group GR14.1 may optionally be substituted independently of one another by one or more substituents selected from the group consisting of
  fluorine, chlorine, bromine, HO—, NC—, $O_2N$—, $F_3C$—, $HF_2C$—, $FH_2C$—, $F_3C$—$CH_2$—, HO—$C_{1-6}$-alkyl-, $CH_3$—O—$C_{1-6}$-alkyl-, $C_{1-6}$-alkyl-, and $C_{1-6}$-alkyl-O— and $(R^{13})_2N$—CO—, and pharmaceutically acceptable salts thereof.

2. A compound according to claim 1, wherein
A is selected from the group GA.2 consisting of
  —$CH_2$—, —$CH_2$—$CH_2$—, —$CH_2$—$CH_2$—$CH_2$—, aryl-, and heteroaryl-,
  wherein the above-mentioned members of the group GA.2 may optionally be substituted independently of one another by one or more substituents selected from the group consisting of
  fluorine, chlorine, bromine, NC—, $F_3C$—, $HF_2C$—, $FH_2C$—, $F_3C$—$CH_2$—, $F_3C$—O—, $HF_2C$—O—, $FH_2C$—O—, HO—$C_{1-6}$-alkyl-, $C_{1-6}$-alkyl-O—$C_{1-6}$-alkyl-, $C_{1-6}$-alkyl-, and $C_{1-6}$-alkyl-O—.

3. A compound according to claim 1, wherein
A is selected from the group GA.3 consisting of
  —$CH_2$—$CH_2$—, —$CH_2$—$CH_2$—$CH_2$—, phenyl-, and pyridyl-,
  wherein the above-mentioned members of the group GA.3 may optionally be substituted independently of one another by one or more substituents selected from the group consisting of
  fluorine, chlorine, bromine, NC—, $F_3C$—, $HF_2C$—, $FH_2C$—, $F_3C$—$CH_2$—, $F_3C$—O—, $HF_2C$—O—, $FH_2C$—O—, $H_3C$—, and $C_{1-6}$-alkyl-O—.

4. A compound according to claim 1, wherein
$R^1$ is H—.

5. A compound according to claim 1 wherein
$R^2$ is selected from the group GR2.2 consisting of
  fluorine, chlorine, bromine, NC—, $F_3C$—, $HF_2C$—, $FH_2C$—, $F_3C$—$CH_2$—, $C_{1-6}$-alkyl-, $C_{1-6}$-alkyl-S—, $C_{3-7}$-cycloalkyl-, $C_{3-7}$-cycloalkyl-$C_{1-6}$-alkyl-, and $R^{14}$—O—.

6. A compound according to claim 1 wherein
$R^4$ is selected from the group GR4.2 consisting of
  H—, $F_3C$—, $HF_2C$—, $FH_2C$—, $F_3C$—$CH_2$—, $C_{1-6}$-alkyl-, $C_{1-6}$-alkyl-S—$C_{1-3}$-alkyl-, $C_{3-7}$-cycloalkyl-, $C_{3-7}$-cycloalkyl-$C_{1-3}$-alkyl-, aryl-, aryl-$C_{1-6}$-alkyl-, heterocyclyl-, heterocyclyl-$C_{1-3}$-alkyl-, heteroaryl-, heteroaryl-$C_{1-3}$-alkyl-, and $R^{14}$—O—$C_{1-3}$-alkyl-,
  wherein the above-mentioned members of the group GR4.2 may optionally be substituted independently of one another by one or more substituents selected from the group consisting of
  fluorine, chlorine, bromine, HO—, NC—, $F_3C$—, $HF_2C$—, $FH_2C$—, $F_3C$—$CH_2$—, HO—$C_{1-6}$-alkyl-, $CH_3$-O—$C_{1-6}$-alkyl-, $C_{1-6}$-alkyl-, and $C_{1-6}$-alkyl-O—.

7. A compound according to claim 1 wherein
$R^6$ and $R^7$ are selected from the group GR6/7.3 consisting of
H, $C_{1-8}$-alkyl-, $C_{3-6}$-cycloalkyl-, $C_{3-6}$-cycloalkyl-$C_{1-3}$-alkyl-, heterocyclyl-$C_{1-6}$-alkyl-, and $C_{6-12}$-polycycloalkyl-,
wherein the above-mentioned members of the group GR6/7.3 may optionally be substituted independently of one another by one or more substituents selected from the group GR6/7S3 consisting of
fluorine, HO—, NC—, $C_{1-3}$-alkyl-, HO—$C_{1-6}$-alkyl-, $C_{1-4}$-alkyl-O—$C_{1-3}$-alkyl-, and $C_{1-3}$-alkyl-O—.

8. A compound according to claim 1 wherein
$R^6$ are selected from the group GR6.4 consisting of
$C_{1-6}$-alkyl-, $C_{5-6}$-cycloalkyl-, heterocyclyl-$C_{1-6}$-alkyl-, and $C_{6-12}$-polycycloalkyl-,
wherein the above-mentioned members of the group GR6.4 may optionally be substituted independently of one another by one or more substituents selected from the group consisting of
fluorine, hydroxymethyl, methoxy-, methoxymethyl- and $H_3C$—.

9. A compound according to claim 1 wherein
$R^7$ is selected from the group GR7.4 consisting of
$C_{1-4}$-alkyl-, cyclopropyl-, and cyclopropyl-$C_{1-3}$-alkyl-
wherein the above-mentioned members of the group GR7.4 may optionally be substituted independently of one another by one or more substituents selected from the group consisting of
fluorine, CN—, HO—, and $H_3C$—O—.

10. A compound according to claim 1 wherein
$R^8$ is selected from the group GR8.3 consisting of
$C_{1-6}$-alkyl-, $C_{3-6}$-cycloalkyl-, and $C_{3-6}$-cycloalkyl-$C_{1-3}$-alkyl-,
wherein the above-mentioned members of the group GR8.3 may optionally be substituted independently of one another by one or more substituents selected from the group consisting of fluorine, HO—, NC—, phenyl- and $H_3C$—,
wherein the above-mentioned phenyl group may optionally be substituted with one or more chlorines.

11. A compound according to claim 1 wherein
$R^9$ is selected from the group GR9.3 consisting of
H—, $F_3C$—$CH_2$—, and $C_{1-6}$-alkyl-,
wherein the above-mentioned members of the group GR9.3 may optionally be substituted independently of one another by one or more flourines.

12. A compound according to claim 1 wherein
$R^{12}$ is selected from the group GR12.2 consisting of
$F_3C$—, $HF_2C$—, $FH_2C$—, $C_{1-6}$-alkyl-, $C_{1-6}$-alkyl-S—$C_{1-3}$-alkyl-, $C_{3-7}$-cycloalkyl-, $C_{3-7}$-cycloalkyl-$C_{1-6}$-alkyl-, aryl-, aryl-$C_{1-6}$-alkyl-, heterocyclyl-, heterocyclyl-$C_{1-6}$-alkyl-, heteroaryl-, and heteroaryl-$C_{1-6}$-alkyl-,
wherein the above-mentioned members of the group GR12.2 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$—, HO—$C_{1-3}$-alkyl-, $C_{1-4}$-alkyl-O—$C_{1-3}$-alkyl-,$C_{1-3}$-alkyl-, and $C_{1-3}$-alkyl-O—.

13. A compound according to claim 1 wherein
$R^{13}$ is selected from the group GR13.2 consisting of
H—, $F_3C$—$CH_2$—, $C_{1-6}$-alkyl-, $C_{3-7}$-cycloalkyl-, $C_{3-7}$-cycloalkyl-$C_{1-3}$-alkyl-, aryl-, aryl-$C_{1-3}$-alkyl-, heterocyclyl-, heterocyclyl-$C_{1-3}$-alkyl-, heteroaryl-, and heteroaryl-$C_{1-3}$-alkyl-,
wherein two $C_{1-6}$-alkyl groups bound to the same nitrogen atom may be joined together forming, together with the nitrogen atom to which they are bound, a 3 to 7 membered heterocyclic ring, and
wherein the above-mentioned members of the group GR13.2 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$-, HO—$C_{1-6}$-alkyl-, $C_{1-4}$-alkyl-O—$C_{1-3}$-alkyl-,$C_{1-6}$-alkyl-, and $C_{1-6}$-alkyl-O—.

14. A compound according to claim 1 wherein
$R^{14}$ is selected from the group GR14.2 consisting of
H—, $F_3C$—, $HF_2C$—, $FH_2C$—, $F_3C$—$CH_2$—, $C_{1-6}$-alkyl-, $C_{3-7}$-cycloalkyl-, $C_{3-7}$-cycloalkyl-$C_{1-3}$-alkyl-, , aryl-, aryl-$C_{1-3}$-alkyl-, heterocyclyl-, heterocyclyl-$C_{1-3}$-alkyl-, heteroaryl- and heteroaryl-$C_{1-3}$-alkyl-,
wherein the above-mentioned members of the group GR14.2 may optionally be substituted independently of one another by one or more substituents selected from the group consisting of
fluorine, chlorine, bromine, HO—, NC—, $F_3C$—, $HF_2C$—, $FH_2C$—, $F_3C$—$CH_2$-, $C_{1-3}$-alkyl-, and $C_{1-6}$-alkyl-O—.

15. A pharmaceutical composition comprising a compound of formula I according to claim 1 and a pharmaceutically acceptable carrier.

16. A pharmaceutical composition comprising a compound of formula 1, according to claim 1, combined with one, two or three pharmaceutically active compounds selected from the group consisting of beta-secretase inhibitors, gamma-secretase inhibitors, amyloid aggregation inhibitors, directly or indirectly acting neuroprotective substances; antioxidants, Cox inhibitors, NSAIDs additionally or exclusively having Aβ lowering properties, HMG-CoA reductase inhibitors, acetylcholinesterase inhibitors, NMDA receptor antagonists, AMPA agonists; substances modulating the concentration or release of neurotransmitters; substances inducing the secretion of growth hormone, CB-1 receptor antagonists or inverse agonists, antibiotics, PDE-IV inhibitors, PDE-IX inhibitors, $GABA_A$ inverse agonists, nicotinic agonists, histamine H3 antagonists, 5 HAT-4 agonists or partial agonists, 5HT-6 antagonists, a2-adrenoreceptor antagonists, muscarinic M1 agonists, muscarinic M2 antagonists and metabotropic glutamate-receptor 5 positive modulators.

* * * * *

UNITED STATES PATENT AND TRADEMARK OFFICE
CERTIFICATE OF CORRECTION

| | | |
|---|---|---|
| PATENT NO. | : 8,426,607 B2 | Page 1 of 1 |
| APPLICATION NO. | : 12/812476 | |
| DATED | : April 23, 2013 | |
| INVENTOR(S) | : Fuchs et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 105 days.

Signed and Sealed this
Third Day of December, 2013

Margaret A. Focarino
*Commissioner for Patents of the United States Patent and Trademark Office*